United States Patent
Boyd

(10) Patent No.: US 9,820,969 B2
(45) Date of Patent: *Nov. 21, 2017

(54) METHODS FOR TREATING AND DIAGNOSING BLINDING EYE DISEASES

(71) Applicant: Translatum Medicus Inc., Toronto (CA)

(72) Inventor: Shelley Romayne Boyd, Toronto (CA)

(73) Assignee: TRANSLATUM MEDICUS INC., Toronto, Ontario ( * ) Notice: Subject to any disclaimer, the term of this patent is extended or adjusted under 35 U.S.C. 154(b) by 0 days.

This patent is subject to a terminal disclaimer.

(21) Appl. No.: 15/236,861

(22) Filed: Aug. 15, 2016

(65) Prior Publication Data

US 2016/0346250 A1  Dec. 1, 2016

Related U.S. Application Data

(63) Continuation of application No. 14/636,639, filed on Mar. 3, 2015, now Pat. No. 9,662,407, which is a continuation of application No. 13/838,473, filed on Mar. 15, 2013, now Pat. No. 8,999,292.

(60) Provisional application No. 61/693,226, filed on Aug. 24, 2012, provisional application No. 61/641,393, filed on May 2, 2012, provisional application No. 61/640,854, filed on May 1, 2012.

(51) Int. Cl.
| | | |
|---|---|---|
| *A61K 31/416* | (2006.01) | |
| *A61K 49/00* | (2006.01) | |
| *A61K 31/415* | (2006.01) | |
| *A61K 9/00* | (2006.01) | |
| *A61K 45/06* | (2006.01) | |

(52) U.S. Cl.
CPC .......... *A61K 31/416* (2013.01); *A61K 9/0019* (2013.01); *A61K 9/0048* (2013.01); *A61K 31/415* (2013.01); *A61K 45/06* (2013.01); *A61K 49/0008* (2013.01)

(58) Field of Classification Search
CPC ...... A61K 9/00; A61K 9/0019; A61K 9/0048; A61K 31/416
See application file for complete search history.

(56) References Cited

U.S. PATENT DOCUMENTS

| | | | |
|---|---|---|---|
| 4,451,477 A | 5/1984 | Silvestrini et al. | |
| 4,999,367 A | 3/1991 | Baiocchi et al. | |
| 5,112,986 A | 5/1992 | Baiocchi et al. | |
| 5,278,183 A | 1/1994 | Silvestrini | |
| 6,020,356 A | 2/2000 | Guglielmotti et al. | |
| 6,093,743 A | 7/2000 | Lai et al. | |
| 6,274,627 B1 | 8/2001 | Lai et al. | |
| 6,316,502 B1 | 11/2001 | Lai et al. | |
| 6,319,517 B1 | 11/2001 | Cavallo et al. | |
| 6,337,087 B1 | 1/2002 | Cavallo et al. | |
| 6,534,534 B1 | 3/2003 | Guglielmotti et al. | |
| 6,589,991 B1 | 7/2003 | Lai et al. | |
| 6,596,770 B2 | 7/2003 | Lai et al. | |
| 6,649,591 B2 | 11/2003 | Lai | |
| 6,673,908 B1 | 1/2004 | Stanton, Jr. | |
| 7,553,496 B2 | 6/2009 | Ambati | |
| 7,732,162 B2 | 6/2010 | Hoffman et al. | |
| 7,816,497 B2 | 10/2010 | Ambati | |
| 7,928,284 B2 | 4/2011 | Ambati | |
| 8,008,092 B2 | 8/2011 | Ambati | |
| 8,067,031 B2 | 11/2011 | Daniloff et al. | |
| 8,158,152 B2 | 4/2012 | Palepu | |
| 8,198,310 B2 | 6/2012 | Guglielmotti et al. | |
| 8,232,265 B2 | 7/2012 | Rogers et al. | |
| 8,835,481 B2 * | 9/2014 | Guglielmotti ........ | C07D 231/56 514/406 |
| 2003/0207309 A1 | 11/2003 | Hageman et al. | |
| 2004/0177387 A1 | 9/2004 | Jayakrishna | |
| 2006/0067935 A1 | 3/2006 | Ambati | |
| 2006/0135423 A1 | 6/2006 | Ambati | |
| 2006/0263409 A1 | 11/2006 | Peyman | |
| 2007/0190055 A1 | 8/2007 | Ambati | |
| 2007/0191273 A1 | 8/2007 | Ambati | |
| 2008/0299130 A1 | 12/2008 | Ambati | |
| 2009/0123375 A1 | 5/2009 | Ambati | |
| 2009/0186376 A1 | 7/2009 | Ambati et al. | |
| 2009/0260091 A1 | 10/2009 | Ambati | |

(Continued)

FOREIGN PATENT DOCUMENTS

| | | |
|---|---|---|
| EP | 0131317 | 1/1985 |
| WO | WO 9716185 | 5/1997 |

(Continued)

OTHER PUBLICATIONS

International Search Report and Written Opinion for International Application No. PCT/CA2013/050335, dated Aug. 23, 2013, 12 pages.
Arnold, J. J. et al., "Reticular Pseudodrusen. A Risk Factor in Age-Related Maculopathy," Retina 15:183-191 (1995).
Beckmann, N. et al., "In vivo visualization of macrophage infiltration and activity in inflammation using magnetic resonance imaging," WIREs Nanomed. Nanobiotechnol. 1:272-298 (2009).
Bindewald, A. et al., "Classification of abnormal fundus autofluorescence patterns in the junctional zone of geographic atrophy in patients with age related macular degeneration," Br. J. Ophthalmol. 89:874-878 (2005).
Bindewald, A. et al., "Classification of Fundus Autofluorescence Patterns in Early Age-Related Macular Disease," Invest. Ophthalmol. Vis. Sci. 46:3309-3314 (2005).

(Continued)

*Primary Examiner* — Michael G Hartley
*Assistant Examiner* — Jagadishwar Samala
(74) *Attorney, Agent, or Firm* — Morgan, Lewis & Bockius LLP

(57) ABSTRACT

This invention relates to, in part, methods and compositions that are useful for the diagnosis, treatment, or prevention of a blinding eye disease, including in the discovery of drugs that are efficacious against these diseases. Diseases include, for example, age related macular degeneration and reticular pseudodrusen disease, and the methods described herein include, for example, the method named delayed near infrared analysis (DNIRA).

13 Claims, 39 Drawing Sheets

(56) References Cited

U.S. PATENT DOCUMENTS

| | | |
|---|---|---|
| 2011/0097390 A1 | 4/2011 | Ambati |
| 2011/0182908 A1 | 7/2011 | Hageman et al. |
| 2011/0268723 A1 | 11/2011 | Ambati |
| 2012/0064010 A1 | 3/2012 | Ambati et al. |

FOREIGN PATENT DOCUMENTS

| | | |
|---|---|---|
| WO | WO 9836735 | 8/1998 |
| WO | WO 9836736 | 8/1998 |
| WO | WO 2004041160 | 5/2004 |
| WO | WO 2005108431 | 11/2005 |
| WO | WO 2007098113 | 8/2007 |
| WO | WO 2007133800 | 11/2007 |
| WO | WO 2008061671 | 5/2008 |
| WO | WO 2009105260 | 8/2009 |
| WO | WO 2010138591 | 12/2010 |
| WO | WO 2011036047 | 3/2011 |
| WO | WO 2011153234 | 12/2011 |
| WO | WO 2013163758 | 11/2013 |

OTHER PUBLICATIONS

Boretsky, A. et al., "Quantitative Evaluation of Retinal Response to Laser Photocoagulation Using Dual-Wavelength Fundus Autofluorescence Imaging in a Small Animal Model," Invest. Ophthalmol. Vis. Sci. 52:6300-6307 (2011).
Boyd, S. R. et al., "Reticular Fundus Autofluorescence (FAF) in the Evolution of Geographic Atrophy (GA) in a Rat Model of RPE Toxicity," 2012 ARVO Annual Meeting, Abstract of Program#/Poster# 6504/A430, 2 pages (May 10, 2012).
Buono, C. et al., "Fluorescent pegylated nanoparticles demonstrate fluid-phase pinocytosis by macrophages in mouse atherosclerotic lesions," J. Clin. Invest. 119(5):1373-1381 (2009).
Cone, R. E. et al., "Regulation of Experimental Autoimmune Uveitis (EAU) Induction in Mice by the Phosphodiesterase Inhibitor Dipyrimidol and of Active EAU by Bindarit, an Inhibitor of Monocyte Chemotactic Proteins," 2011 ARVO Annual Meeting, Abstract of Program#/Poster# 22601A426, 5 pages (May 2, 2011).
Duker, J. S., "The complete trial for dry AMD: Results," Review of Ophthalmology, Sep. 6, 2012, 3 pages.
Enzmann, V. et al., "Behavioral and anatomical abnormalities in a sodium iodate-induced model of retinal pigment epithelium degeneration," Exp. Eye Res. 82:441-448 (2006).
Eter, N. et al., "In Vivo Visualization of Dendritic Cells, Macrophages, and Microglial Cells Responding to Laser-Induced Damage in the Fundus of the Eye," Invest. Ophthalmol. Vis. Sci. 49(8):3649-3658 (2008).
Fleckenstein, M. et al., "Fundus Autofluorescence and Spectral-Domain Optical Coherence Tomography Characteristics in a Rapidly Progressing Form of Geographic Atrophy," Invest. Ophthalmol. Vis. Sci. 52(6):3761-3766 (2011).

Franco, L. M. et al., "Decreased Visual Function after Patchy Loss of Retinal Pigment Epithelium Induced by Low-Dose Sodium Iodate," Invest. Ophthalmol. Vis. Sci. 50(8):4004-4010 (2009).
Kiuchi, K. et al., "Morphologic characteristics of retinal degeneration induced by sodium iodate in mice," Curr. Eye Res. 25(6):373-379 (2002).
Ladewig, M. S. et al., "Prostaglandin E1 infusion therapy in dry age-related macular degeneration," Prostaglandins, Leukotrienes and Essential Fatty Acids, 72:251-256 (2005).
Lois N. et al., "Fundus Autofluorescence in Patients With Age-related Macular Degeneration and High Risk of Visual Loss," Am. J. Ophthalmol. 133:341-349 (2002)).
Luhmann, U. F. O. et al., "The Drusenlike Phenotype in Aging Ccl2-Knockout Mice Is Caused by an Accelerated Accumulation of Swollen Autofluorescent Subretinal Macrophages," Invest. Ophthalmol. Vis. Sci. 50:5934-5943 (2009).
Mendes-Jorge, L. et al., "Scavenger Function of Resident Autofluorescent Perivascular Macrophages and Their Contribution to the Maintenance of the Blood-Retinal Barrier," Invest. Opthalmol. Vis. Sci. 50(12):5997-6005 (2009).
Mizota, A. et al., "Functional Recovery of Retina After Sodium Iodate Injection in Mice," Vision Res. 37(14):1859-1865 (1997).
Obata, R. et al., "Retinal degeneration is delayed by tissue factor pathway inhibitor-2 in RCS rats and a sodium-iodate-induced model in rabbits," Eye 19:464-468 (2005).
Ohtaka, K. et al., "Protective Effect of Hepatocyte Growth Factor Against Degeneration of the Retinal Pigment Epithelium and Photoreceptor in Sodium Iodate-Injected Rats," Curr. Eye Res. 31:347-355 (2006).
Ross, R. J. et al., "Immunological protein expression profile in Ccl2/Cx3cr1 deficient mice with lesions similar to age-related macular degeneration," Exp. Eye Res. 86(4):675-683 (2008).
Sarks, J. et al., "Evolution of reticular pseudodrusen," Br. J. Ophthalmol. 95:979-985 (2011).
Spencer, D. B. et al., "In vivo imaging of the immune response in the eye," Semin. Immunopathol. 30:179-190 (2008).
Tanaka, M. et al., "Third-Order Neuronal Responses Contribute to Shaping the Negative Electroretinogram in Sodium Iodate-Treated Rats," Curr. Eye Res. 30:443-453 (2005).
Zeng X-X et al., "Labelling of retinal microglial cells following an intravenous injection of a fluorescent dye into rats of different ages," J. Anat. 196:173-179 (2000).
Zhao, X. et al., "Patches of RPE Loss Can Be Detected In Vivo in the Rat Eye Using Confocal Scanning Laser Ophthalmoscopy," 2011 ARVO Annual Meeting, Abstract of Program#/Poster# 969/A161, 2 pages (May 1, 2011).
Zweifel, S. A. et al., "Prevalence and Significance of Subretinal Drusenoid Deposits (Reticular Pseudodrusen) in Age-Related Macular Degeneration," Ophthalmology 117(9):1775-1781 (2010).
Zweifel, S. A. et al., "Reticular Pseudodrusen Are Subretinal Drusenoid Deposits," Ophthalmology 117(2):303-312 (2010).

* cited by examiner

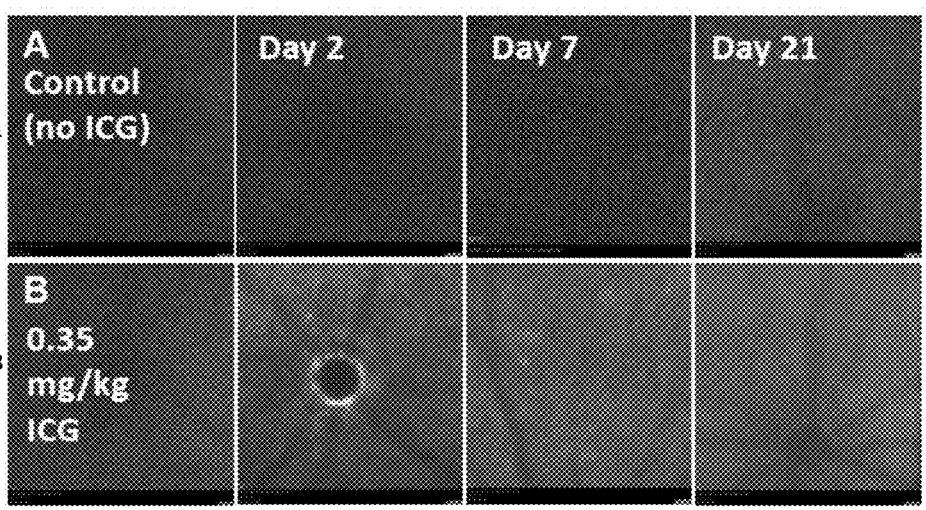

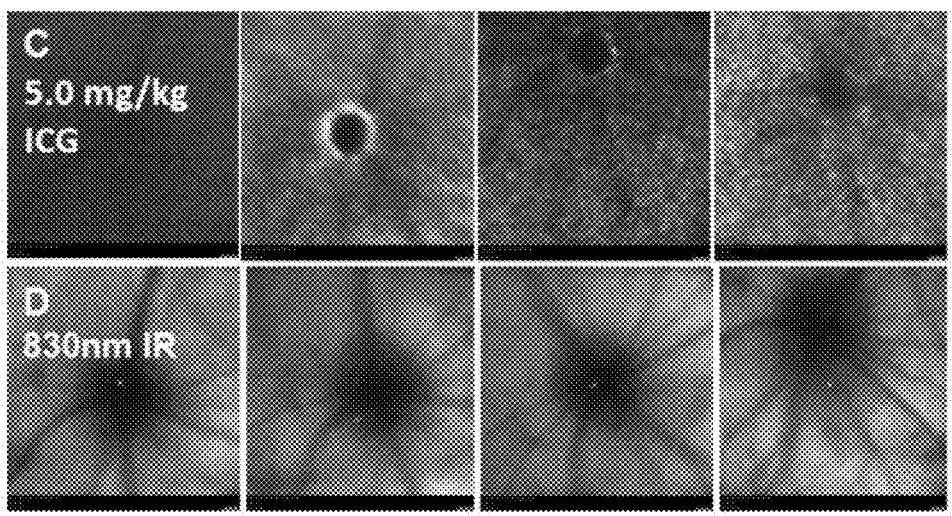

FIG. 10A
FIG. 10B
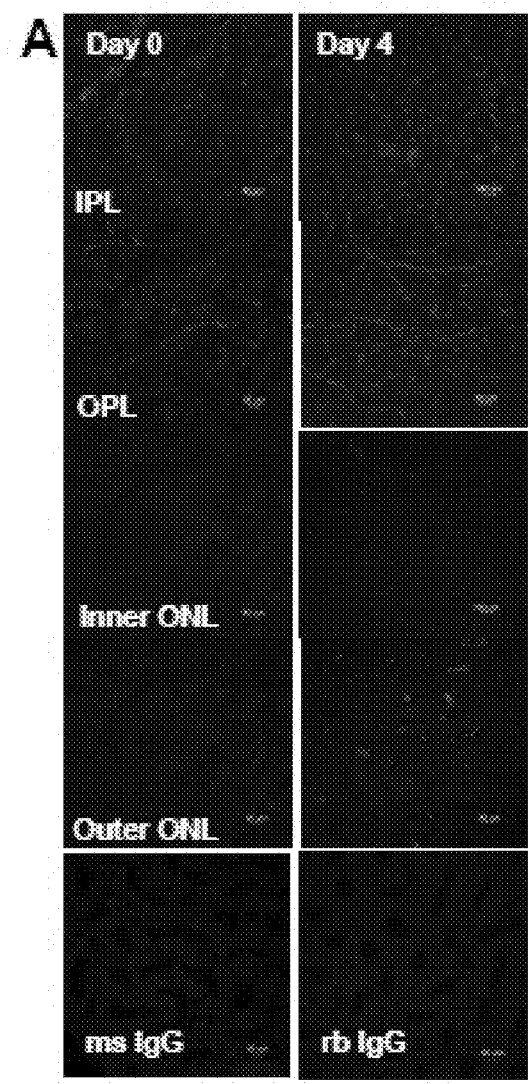
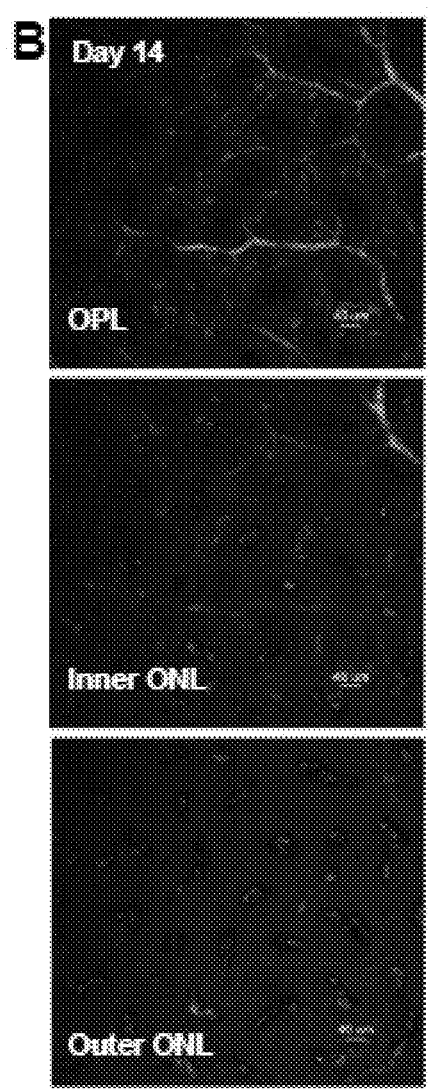

METHODS FOR TREATING AND DIAGNOSING BLINDING EYE DISEASES

PRIORITY

This application is a continuation of U.S. patent application Ser. No. 13/838,473, filed Mar. 15, 2013, which claims priority to and the benefit of U.S. Provisional Patent Application No. 61/693,226, filed Aug. 24, 2012, U.S. Provisional Patent Application No. 61/641,393, filed May 2, 2012, and U.S. Provisional Patent Application No. 61/640,854, filed May 1, 2012, each of which is incorporated herein in their entireties by reference.

FIELD OF THE INVENTION

This invention relates to methods and compositions that are useful for the diagnosis, treatment, or prevention of a blinding eye disease, including the discovery of drugs that are efficacious against these diseases.

BACKGROUND

Blinding eye diseases include a number of disorders that effect vision. Age-related macular degeneration (AMD) is the leading cause of ocular dysfunction, including blindness. One form of AMD, non-exudative AMD, also known as "dry" AMD, is typically characterized by drusen accumulation within or external to the retinal pigment epithelium (RPE). Late in dry AMD, atrophy of the RPE and the overlying rod and cone photoreceptors occurs. A second form of AMD, exudative or "wet" or "neovascular" AMD, is characterized by choroidal neovascularization. Early stage disease is frequently dry AMD while later stage disease is frequently either wet (neovascular) AMD or dry (atrophic) AMD.

Drusen are whitish spots or deposits that occur within the RPE or external to it. Drusen are the defining or pathognomic feature of AMD. By contrast, the terms "pseudodrusen" or "drusenoid deposits" or "subretinal drusenoid deposits" have been used to describe discrete deposits or a yellowish curvilinear or reticular pattern that are suggested to lie anterior to the RPE, relative to the path of light entering the eye, in the sub-retinal space.

Because of differences in imaging techniques, there is controversy around the prevalence of reticular pseudodrusen (RPD), with many hypothesizing that it is under-estimated. Like AMD, RPD is associated with aging. RPD is also strongly associated with vision loss, typically due to geographic atrophy or choroidal neovascularization. Unlike classic AMD, it is however characterized by an interlacing, curvilinear or reticular pattern that can be visualized in multiple wavelengths of light including but not limited to white, blue, blue autofluorescence, red-free, near infra-red or infra-red. The defining or pathognomic feature of RPD is not drusen but rather "pseudodrusen", "drusenoid deposits" or "subretinal drusenoid deposits" that appear as base-down domes, triangles or spike-like deposits that lie anterior to (above) the RPE in the subretinal space, when evaluating the outer retina and RPE in the transverse plane, as can occur optically using for example, optical coherence tomography (OCT) or in post-enucleation samples using for example, histology with or without immunohistochemistry. Unlike classic AMD, RPD may be associated with increased cardiovascular death. At present, without wishing to be bound by theory, RPD may be considered a distinct form of age-related macular disease rather than a subtype of AMD. RPD may also be considered to be a "diffuse-trickling" subtype of dry AMD.

There is presently a paucity of drugs for effective treatment of blinding eye diseases, such as AMD or RPD. Therefore, there remains a need for therapies that are useful for treating these diseases and other blinding eye diseases. Further, there is a need for effective diagnosis of these diseases.

SUMMARY OF THE INVENTION

Accordingly, in one aspect, the invention provides a method for identifying whether a candidate compound is useful for the treatment of a blinding eye disease, comprising (a) administering an effective amount of a test compound to an animal whose eye comprises (i) a fluorescent compound in an amount effective to indicate the presence of a blinding eye disease in the animal and (ii) a toxin in an amount effective to induce atrophy of ocular tissue; (b) exposing the eye to light having a wavelength and intensity effective to cause the fluorescent compound to fluoresce; (c) comparing the eye's fluorescence pattern to a fluorescence pattern of an animal's eye that comprises the fluorescent compound and the toxin but not the test compound; and (d) selecting the test compound as a candidate compound if the result of the comparison of step (c) indicates that the test compound is useful for the treatment of a blinding eye disease.

In another aspect, the invention provides a method for treating or preventing dry AMD, comprising administering to a subject in need thereof an effective amount of a compound of Formula I:

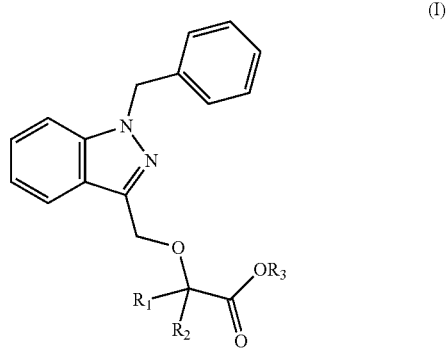

(I)

or a pharmaceutically acceptable salt thereof, wherein each of $R_1$ and $R_2$ is independently H or a $C_1$-$C_6$ alkyl and $R_3$ is H or a $C_1$-$C_6$ alkyl.

In a further aspect, the invention provides a method for treating or preventing dry AMD, comprising administering to a subject in need thereof an effective amount of methotrexate or a pharmaceutically acceptable salt thereof.

In another aspect, the invention provides a method of treating RPD disease, comprising administering to a subject in need thereof an effective amount of a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl.

In still another aspect, the invention provides a method of treating RPD disease, comprising administering to a subject in need thereof an effective amount of methotrexate or a pharmaceutically acceptable salt thereof.

In yet another aspect, the invention provides a method for identifying a subject who has a blinding eye disease and is likely to respond to treatment with an agent comprising determining whether the subject's eye has, or previously had, an increase (including a transient increase) in permeability across the epithelial barrier between a choroid and a retina of the eye relative to an undiseased state; wherein the increase in permeability indicates that the subject is more likely than not to respond to treatment with the agent; and wherein the agent is selected from methotrexate or a pharmaceutically acceptable salt thereof, or and a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl.

In still another aspect, the present invention provides a method for identifying a blinding eye disease subject who is more likely than not to respond to treatment with an agent comprising determining whether the subject's eye has an presence (e.g. an influx) of phagocytic immune cells across a RPE relative to an undiseased state, wherein the presence of phagocytic immune cells indicates that the subject is more likely than not to respond to treatment with the agent; and wherein the agent is selected from methotrexate or a pharmaceutically acceptable salt thereof, or and a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl.

In another aspect, the invention provides a method for determining whether a blinding eye disease in a subject is responsive to treatment with an agent that inhibits the function of a subject's immune cells, comprising detecting a presence, detecting an absence, or measuring an amount of immune cells in the subject's eye, wherein the subject's eye fluoresces in response to light having a wavelength of about 600 nm to about 900 nm.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE FIGURES

FIG. 1A shows a time course of early FAF change around the optic nerve head. A hyperfluorescent line or border formed 2-3 days after NaIO$_3$ injection. The border may or may not completely surround the optic nerve head, and is not contiguous with it. A lacy or reticular pattern of fluorescence appeared between days 3 and 7, and lied peripheral to this line. By day 7 this pattern was distinct.

FIG. 1B shows composite images that include the optic nerve head and mid-peripheral retina and illustrate that the hyperfluorescent borders defined areas of future lacy or reticular hyperfluorescence. In this example, the borders seen at Day 3 post-NaIO$_3$ defined an island in the inferior retina. By day 7 the border was no longer visible, and instead, profound reticular patterns emerged. Note that the image showing two distinct islands at Days 3 and 7 are from different animals and demonstrate how consistently the patterns is observed. Small islands such as these were seen in about 7% of eyes.

FIG. 1C shows that the pattern of FAF is distinctly different from the retinal and choroidal vasculature patterns seen on fluorescein (left and middle image of the inner and mid-retina, respectively) or ICG angiography (right image) of the choroid FIG. 1D shows a transient increase in trans-epithelial permeability that occurred around Day 2 before pattern progression and is evident by a significant flush during ICG angiography (790 nm, approximately 6 minutes after dye injection). This ICG flush was not detected on Day 1 following toxin injection, appeared briefly, and is rarely seen by the next time point routinely tested, at Day 3 or 4.

FIG. 2A shows large composite FAF images encompassing much of the posterior pole and identified a 360° ring of damage defined by both a peri-papillary and peripheral retinal border. FAF images taken 7 days after NaIO$_3$ identified multiple discrete and contiguous areas of curvilinear hyperfluorescence that form oval, round, scalloped, rosette, or paw-print patterns. These typically emerged between days 7 and 14. Detail is provided in the upper enlargement. These complex FAF patterns arise within the earlier hyperfluorescent borders, and coalesce over time.

FIG. 2B shows that by day 14 most animals show a near contiguous pattern of reticular hyperfluorescence throughout the entire 360° ring. Detail is provided in the middle box.

FIG. 2C shows that by 28 days after NaIO$_3$ exposure, the pattern took on a more granular appearance. Small areas where the pattern is less apparent are seen as darker, grey areas.

FIG. 2D shows a clinical image of the "diffuse trickling" pattern of FAF for comparison. The present invention, inter alia, recapitulates many of the features including reticular, lobular or scalloped ovals of grey hypofluorescence associated with peripheral hyperfluorescence.

FIG. 3A shows that this pattern corresponds with the distribution of autofluorescent cells. Low power (1×, left column; 5×, right column) white light images of excised retinal whole mounts taken prior to NaIO$_3$ injection (baseline), and at days 4 and 7 post-injection are shown. A subtle curvilinear pattern is noted 3-4 days after compared to baseline, and is apparent at day 7.

FIG. 3B shows that by day 14 post-NaIO$_3$, this reticular pattern is pronounced and corresponds with gross deformation of the outer retina. This appeared as notches, or folds, in cross-sections seen at the site of relaxing incisions (enlarged in box).

FIG. 3C shows that epifluorescent microscopy in the 488 nm channel, with no cellular staining, showed the presence of autofluorescent cells that lie within the reticular grooves. This was evident both using broad light emission (left column) as well as narrow excitation and emission (right column) and corresponds to the wavelength used during FAF imaging. Folds in the retina were associated with the presence of small fluorescent dots by Day 7. Further enlargement clearly showed the distribution of small fluorescent cells, with voids for their nuclei. Positive control tissue following systemic fluorescein-dextran injection (as for angiography) confirmed the ability to detect 488 nm fluorescence in excised retina or eyecup (similar in wavelength to that used for FAF in HRAII imaging) without tissue processing or staining. Negative control at baseline shows absence of autofluorescent cells.

FIG. 4A shows clinical images from a patient with early AMD and shows reticular pseudodrusen and so-called "target" lesions in the NIR channel (top) Immediately below are two schematic overlays that emphasize the hypofluorescent spots (those typically defined as drusenoid deposits) first in black for emphasis, and then with a bright background to emphasis the intervening bright signal. The bottom two images highlight multiple small target lesions of RPD (within the circles), while the bottom-most schematic, illustrates the presence of a potential halo and target lesion formed by concentric folds of tissue.

FIG. 4B shows schematic renderings which indicate a direct relationship between three-dimensional whole mount ONL histology and two-dimensional en face clinical FAF images. By day 14 after NaIO$_3$ exposure, the outer retina shows complex folds of the mid-ONL (shown at relative low magnification [original 40×] and digitally enlarged). Digital magnification shows concentric rings of tissue folds. This same area illustrated in black and white shows how this might appear on FAF to be a circular or oval region with a central void. Reversed black and white rendering (a "negative" image), shows that this arrangement of ONL distortion would appear to have a central bright target.

FIG. 4C shows OCT imaging of the rat retina 14 days after NaIO$_3$ injection clearly shows bright "spikes" through the outer retina. These are described clinically. Similar histological sections through the outer retina demonstrate ONL folds with underlying inflammatory cells in the enlarged subretinal space that form narrow columns of cells. For comparison with in vivo images, these are rendered in black and white. In reversed black and white (a pseudo-negative image to match OCT images), it is seen that the ONL disappears while the subretinal densities appear bright.

FIG. 5A-F show representative normal confocal scanning laser ophthalmoscopy (cSLO) and angiographic images of wild-type SD rats obtained using:

FIG. 5A: red free.
FIG. 5B: infrared reflectance (830 nm).
FIG. 5C: 488/500 nm autofluorescence (FAF).
FIG. 5D: 795/810 nm NIR fluorescence.

FIGS. 5E-F illustrate normal retinal and choroidal vasculature using fluorescein dextran and ICG dye, respectively. These and similar images served as normal control for all experiments. Such imaging is used to properly align the depth of focus within and between the retina and RPE layers.

FIG. 5G shows a time course of delayed near infrared analysis (DNIRA) in a representative animal that received a single injection of 5 mg/kg ICG dye at t=0. No detectable signal is seen prior to dye injection (note homogenously dark image, upper row). During angiography (second row) the retinal blood vessels were visualized, and background was not detectable noting that the gain (sensitivity) of the cSLO is reduced to prevent saturation during the transit phase. In the days after angiography, (rows 3-5) there is an increased speckled or punctate background fluorescence compared to baseline. The delayed NIR fluorescence is blocked by overlying blood vessels and is absent at the optic nerve head, but unlike FAF (FIG. 5H) forms a bright arc or ring around the nerve head. The signal remains strong and distributed throughout the fundus out to 28 days after injection at the concentration used (5 mg/kg). The slightly darker segment of the bottom row likely reflects the presence of a choroidal vortex vein.

FIG. 5H shows, in contrast to the DNIRA time course, the 488/500 nm autofluorescence signal reverts to pre-injection intensity (top row) when viewed at 3, 8 and 28 days after fluorescein angiography (lower rows). The slightly darker segment of the bottom row likely reflects the presence of a choroidal vortex vein.

FIGS. 6A-D show that the intensity of NIR fluorescent signal correlates with ICG dosage using DNIRA.

FIG. 6A shows control cSLO images illustrate an absence of 795/810 nm fluorescent signal when no ICG dye injection has been given. Control animals that did not receive ICG maintained the same level of background fluorescence with negligible signal over the 21 day period evaluated.

FIG. 6B show that using the same gain, delayed NIR fluorescence was readily detectable 48 hours after ICG injection when given at the low dose of 0.35 mg/kg. However, with time, DNIRA shows gradual fading from 48 hours to 21 days post-injection.

FIG. 6C show that using the same gain, 5 mg/kg ICG angiography resulted in brighter (higher intensity) delayed NIR fluorescence at 48 hours than does the lower dose (FIG. 6B). This fluorescence persisted largely unchanged out to 21 days.

FIG. 6D shows that by contrast, the 830 nm NIR reflectance channel does not show similar change.

FIG. 7A shows DNIRA performed 3 days after ICG and NaIO$_3$ injection. Loss of speckled fluorescence in clearly-defined patches or areas of the posterior pole was seen. These areas appeared dark, or hypofluorescent, with clearly defined borders.

FIG. 7B shows that within these areas, if the gain (sensitivity) of the cSLO is increased, the choroidal blood vessels were readily evident. The box (enlarged) identifies some of the prominent choroidal vessels that travel in directions that are distinct from the retinal vasculature that run radially from the optic nerve (arrows). The speckled DNIRA fluorescence obscures the view to the choroid in the upper right of the image.

FIG. 8A shows that despite significant outer retinal loss by month 3 after NaIO$_3$ administration, the ONL was preserved in the area immediately adjacent to the optic nerve head (ONH). Higher magnification (bottom), confirmed that the photoreceptor nuclei are preserved, and that the outer retina is not thrown into folds. FAF imaging of a representative eye from a Day 7 post-NaIO3 injection animal, confirmed that the reticular pattern is not seen. Fine dotted line (inner circle) represents the location of the ONH, while the coarse dotted line (outer circle) delineates approximate extent of normal, non-reticular FAF.

FIG. 8B shows H&E staining which demonstrated clear deformation of the outer retina following NaIO₃ administration. Prior to NaIO₃ administration (BL), the ONL appeared as a dark linear band that extended from the ONH to the retinal periphery. By 7 days, the outer retina was thrown into folds but the ONL remained grossly intact. This is seen in the enlarged figure in the right column. However, by day 14 post-NaIO3, the ONL showed areas of frank loss, with the inner retina lying directly against Bruch's Membrane (BM), the specialized basement membrane of the RPE. This is seen in the enlarged figure (black arrow).

FIG. 8C shows confocal microscopy through the ONL imaged with the nuclear stain TO-PRO-3 (a carbocyanine monomer nucleic acid stain with far-red fluorescence only, Invitrogen). At baseline, this layer was flat, with no distinguishing features. With increasing time after NaIO₃ administration, the ONL became progressively more deranged. Linear grooves, curvilinear shapes, concentric rings, and isolated small ovals or circles were identified at days 3, 6 and 14.

FIG. 9A shows lower (top row) and higher (bottom row) magnification of both in vivo and ex vivo imaging which displays the comparison between the reticular pattern seen on FAF and IHC early and late in disease progression. The pattern of FAF identified in vivo is recapitulated by fluorescent immunohistochemistry using anti-Iba antibodies. Compared against whole mount retina, excised immediately after HRAII imaging on Day 7, the same reticular pattern was seen using antibodies against Iba-1, a marker of microglia and macrophages (top). Nuclear staining using TO-PRO-3 showed densely packed cells of the outer nuclear layer (the photoreceptor layer) that appear, in two dimensions, to form curvilinear, oval or lobular patterns. Merging of the two confirmed that the Iba-1⁺ staining is found interlaced between the nuclear staining. Enlargement of late stage reticular pattern confirmed that Iba-1⁺ cells remained in the grooves between the folded photoreceptor nuclei (bottom).

FIG. 9B shows that FAF signal can be detected even in the absence of RPE. Left: posterior eye cup, stained with RPE65 (green) shows loss of this monolayer in the central and mid retina (a ring of peripheral RPE remains. The remaining images utilized two different RPE labels (MiTF; microphthalmic transcription factor) and the characteristic double nuclear stain, and confirms loss of the RPE layer in the mid and central eyecup, in areas seen to have a complex pattern of fundus autofluorescence. By contrast, normal or near-normal RPE remains in the eyecup periphery.

FIG. 9C shows nuclear staining indicating the disappearance of RPE cells in the central part of a whole mount retina as evident by the absence of double nuclei which denote RPE cells. RPE was still visible in peripheral retinal tissue. This is in contrast to baseline control, where RPE cells were present in both central and peripheral retinal tissue.

FIGS. 10A-C show serial confocal microscopy through the outer retina, which displays a complex 3-dimensional deformation with corresponding interlacing distribution of Iba-1⁺ and CD68⁺ phagocytic cells.

FIG. 10A shows morphological changes of the outer retina optically sectioned into four layers extending from the inner plexiform layer (IPL) to the subretinal space. The ONL is divided into inner and outer layers. Red=Iba-1, Green=CD68, Blue=nuclei. An increase in the number of phagocytic cells was seen in the retinal layers at Day 4 after NaIO₃ administration compared to baseline, at which time Iba-1 cells are found primarily in the inner retina. This was absent in antibody negative controls for both cell markers.

FIG. 10B shows that by day 14 after NaIO₃ administration, circular and oval patterns were evident in the ONL and as far internally as the OPL (identified by the presence of blood vessels). The pattern was curvilinear in the inner ONL, and more so in the outer ONL where the tightly folded layer of nuclei are much more dense, with smaller areas of curvilinear voids. In the outer ONL, there was significant bridging between folds. These nuclear voids contained Iba-1⁺ and CD68⁺ cells.

FIG. 10C shows an enlarged image in the outermost ONL or expanded subretinal space (which is normally a hypothetical space) shows a reticular pattern of Iba-1⁺ and CD68⁺ cells interlaced between photoreceptor nuclei.

FIG. 11A shows confocal Z-series through the outer retina were used to generate a three dimensional reconstruction of the ONL and Iba1⁺ cells. Nuclear staining (red) of the photoreceptor nuclei layer showed that it is thrown into folds. Merged with Iba-1⁺ staining (green), it was evident that inflammatory cells lie between or within folds defined by retina deformation. Reconstruction of Iba-1 positive cells alone demonstrated the reticular pattern.

FIG. 11B shows Z-series reconstruction of segments of the total image stack of the outer retina 28 days after NaIO₃ administration illustrates the complexity of the folds, that are more narrow at their peaks (inner), and broader and more interlacing at their bases (middle, outer). For comparison with cross-sectional imaging, and to better represent the 3D nature of these findings, an oblique perspective is also shown (middle panels). The position of the asterisk on the en face images (left) corresponded with the location of the asterisk in the oblique images. Digital enlargements (right) showed a groove between the photoreceptor layer (red) that is curvilinear and contiguous in the outer retina, but broken into at least three smaller ovals in the inner-ONL. Iba1⁺ cells (green) were largely located within, i.e. external to, the photoreceptor layer. Control reconstruction of the outer retina showed neither Iba-1 positive cells nor deformation of the ONL (bottom row). Bitplane software (Imaris) was used to generate these images.

FIG. 12A shows in vivo OCT and illustrates early changes that occurred in the inferior retina, but not the superior retina, were observed in the first three days following NaIO₃ administration. Baseline image indicated the retinal layers visible on OCT. En face image of the retina at day 3 illustrated the position of the two optical sections, with superior and inferior portions shown. The superior portion was unchanged compared to baseline. By contrast the inferior showed small undulations of the photoreceptor inner and outer segments, along with loss of the thin RPE layer.

FIG. 12B shows that by Day 14 after NaIO₃ administration, the outer retina showed marked changes including the formation of multiple curved folds, base-down triangles and occasional spikes of bright signal that lie external (inferior) to the dark outer nuclear layer.

FIG. 12C shows a well-formed base-down triangle is indicated in a day 14 image of the rodent retina.

FIG. 12D shows OCT image of a patient with reticular pseudodrusen showing a similar base-down triangle as that seen in the rodent model.

FIG. 13A shows adjacent, consecutive OCT images which confirm that subretinal changes contribute to complex 3D structures in the Y-axis. Small subretinal domes or pyramidal shapes are plentiful, and as shown centrally, also formed a shape similar to an upside down "Y" or "wishbone". Compared against the volumetric reconstruction of serial images this image coincides with optical sections through a structure that appears circular when viewed en face. Images showing the position of serial OCT sections through the circular structure correspond to those in the adjacent optical cross-sections. The two major subretinal signals of these cross-sections (arrows) are seen to be close together at the upper and lower extremities of the circle, and further apart in the centre. The inter-spike distances are provided. Evaluation of the structures immediately left of the circle show a similar contribution of subretinal structures to smaller loop-like structures.

FIG. 13B shows volumetric reconstructions of segmental stacks of serial Z-sections through the inner, mid, and outer ONL confirm the different en face appearance of signal under the deformed outer retina. OCT sections through the same tissue plane. (Upper Row) Volumetrically reconstructed images formed within the three planes bounded by the parallel green lines shown in upper row. Such segmental reconstruction through the inner, mid and outer-ONL demonstrates three distinct patterns. (C. lower row) Regular array of punctate spots in the inner ONL. (C, lower left) More curvilinear pattern in the mid-ONL. (C, middle) Outer-most ONL, largely within the expanded subretinal space, shows multiple complex curvilinear, looping, complex structures with significant bridging between them. These images correlate to the 3D reconstructed confocal microscopy findings. (C, lower right)

FIG. 14A shows how, compared to untreated (bottom panel), GAD treated lesion have less well-demarcated borders at Day 3 (top, left) and far less well demarcated patterns of FAF within the representative island of damage at Day (top, right).

FIG. 14B shows how macrophage depletion leads to smaller areas of damage. Left: F AF image shows small crescent of reticular pattern 7 days after NaIO$_3$ and simultaneous GAD depletion of the macrophages. Right: Relative to the whole excised retina, the area of damage is clearly smaller that typically seen.

FIG. 15A shows clinical images from a patient with early AMD showing reticular pseudodrusen and so-called "target" lesions in the NIR channel (top) Immediately below are two schematic overlays that show the hypofluorescent spots (those typically defined as drusenoid deposits) first in black for emphasis, and then with a bright background to emphasis the intervening bright signal. The bottom two images highlight multiple small target lesions of RPD (within the circles), while the bottom-most schematic, illustrates the presence of a potential halo and target lesion formed by concentric folds of tissue.

FIG. 15B shows schematic renderings suggest a direct relationship between three-dimensional whole mount ONL histology and two-dimensional en face clinical FAF images. By day 14 after NaIO$_3$ administration, the outer retina shows complex folds of the mid-ONL (shown at relative low magnification [original 40×] and digitally enlarged). Digital magnification shows concentric rings of tissue folds. This same area illustrated in black and white showed how this might appear on FAF to be a circular or oval region with a central void. Reversed white & black rendering (i.e., a "negative" image), showed that this arrangement of ONL distortion would appear to have a central bright target.

FIG. 15C shows OCT imaging of the rat retina 14 days after NaIO$_3$ administration clearly shows bright "spikes" through the outer retina. These are described clinically. Similar histological sections through the outer retina demonstrate ONL folds with underlying inflammatory cells in the enlarged subretinal space that form narrow columns of cells. For comparison with in vivo images, these are rendered in black and white. In reversed black and white (i.e., a pseudo-negative image to match OCT images), it is seen that the ONL disappears while the subretinal densities appear bright.

DETAILED DESCRIPTION OF THE INVENTION

Figure 1A:
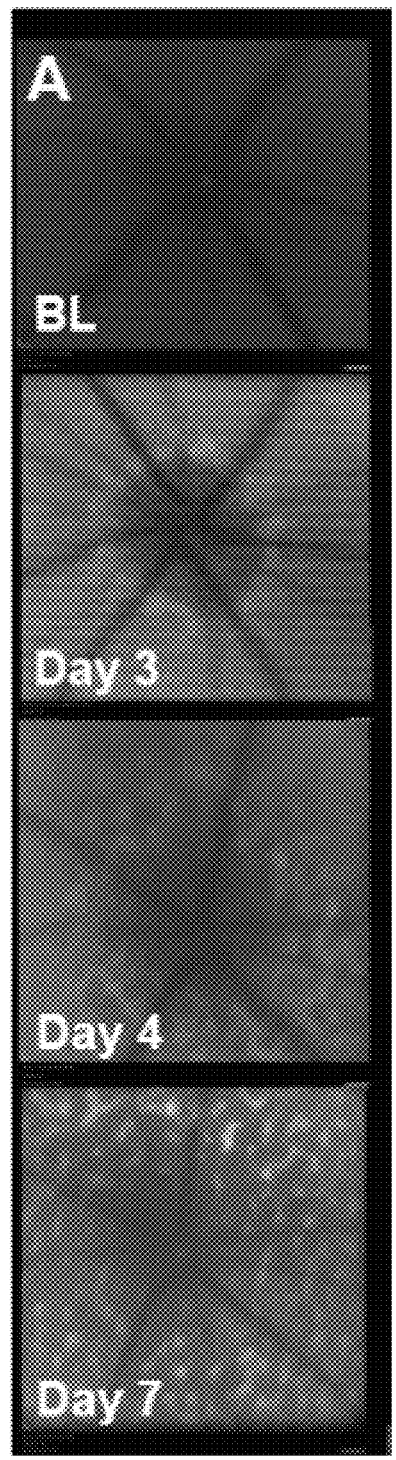
FIGS. 1A-D show that in vivo fundus autofluorescence (FAF) imaging following NaIO$_3$ injection identifies geographic areas of damage that develop a reticular pattern. ICG angiography identifies transient chorioretinal permeability.
Figure 1B:
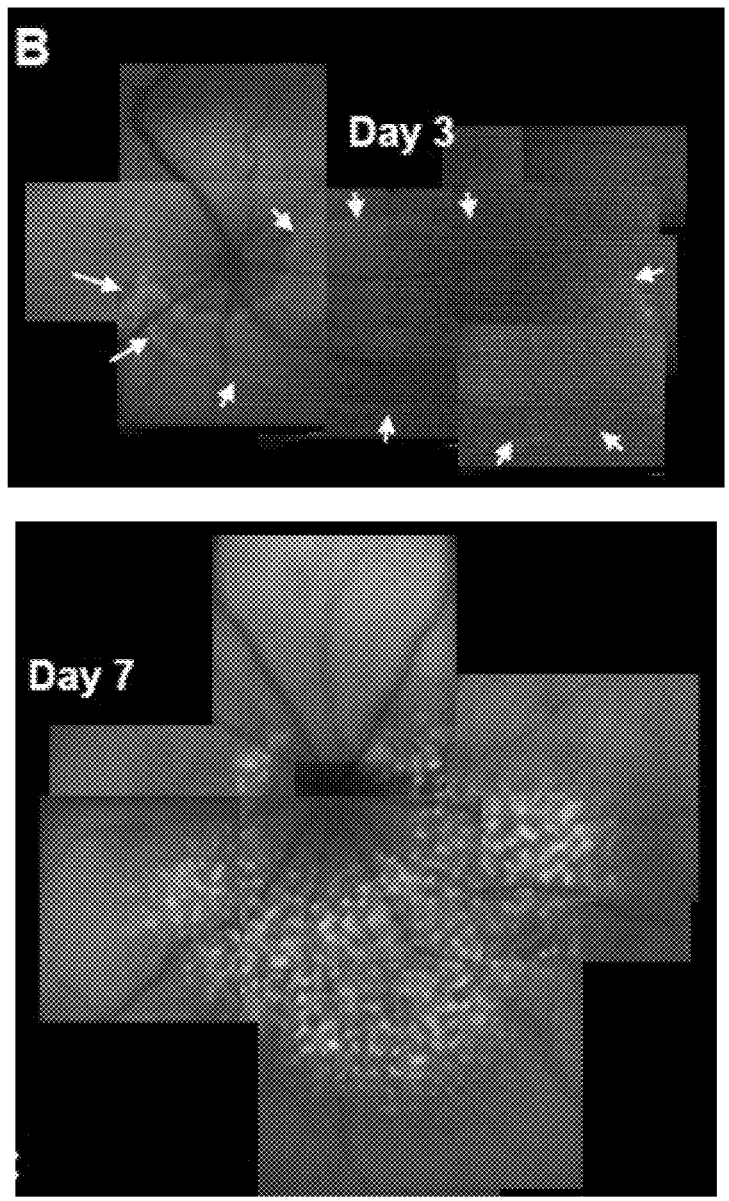
Figure 1C:
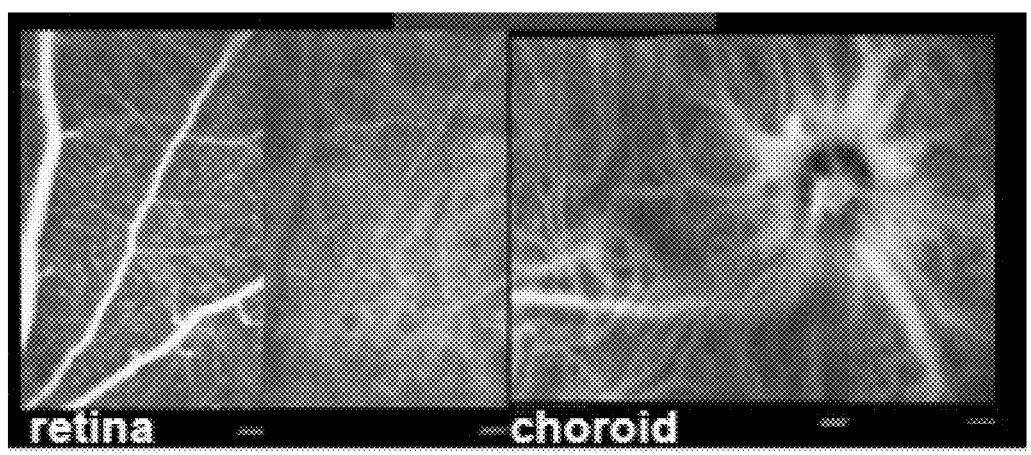
Figure 1D:
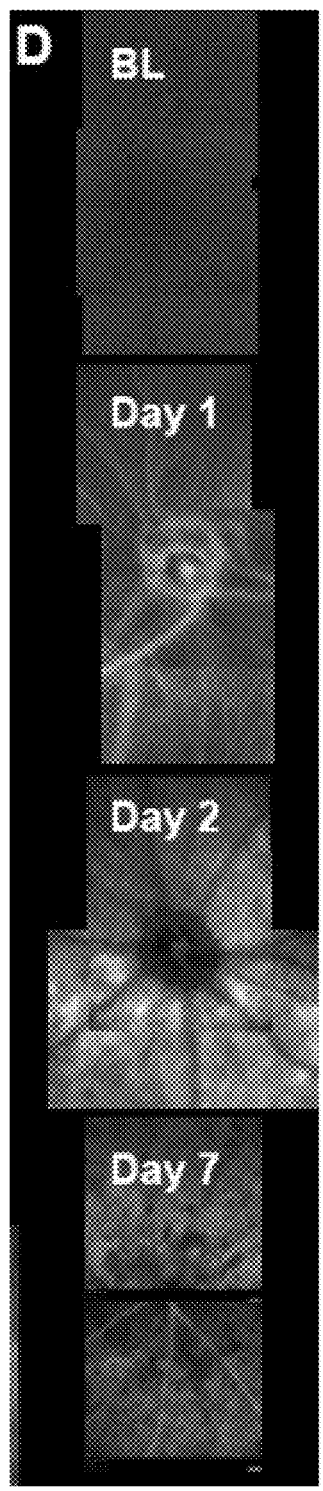
Figure 2A:
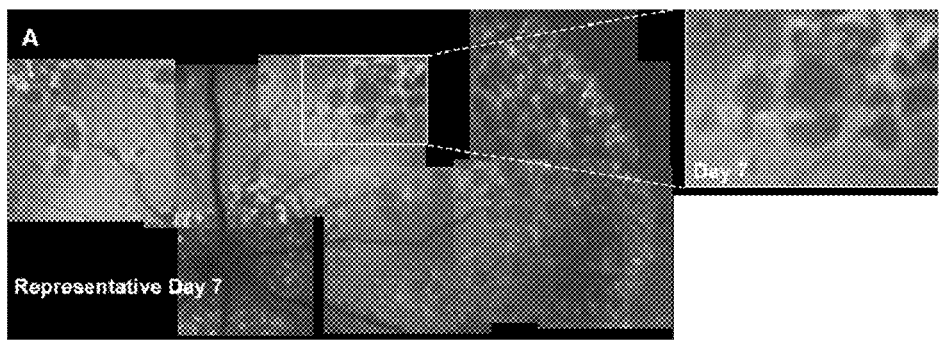
FIGS. 2A-D show maturation of FAF change after NaIO$_3$ injection in large 360° rings.
Figure 2B:
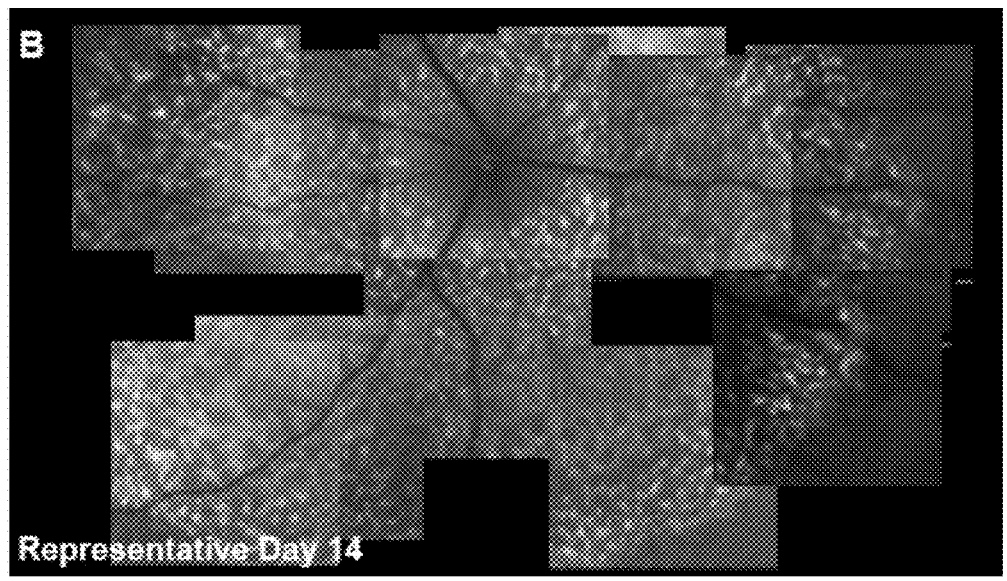
Figures 2C, 2D:
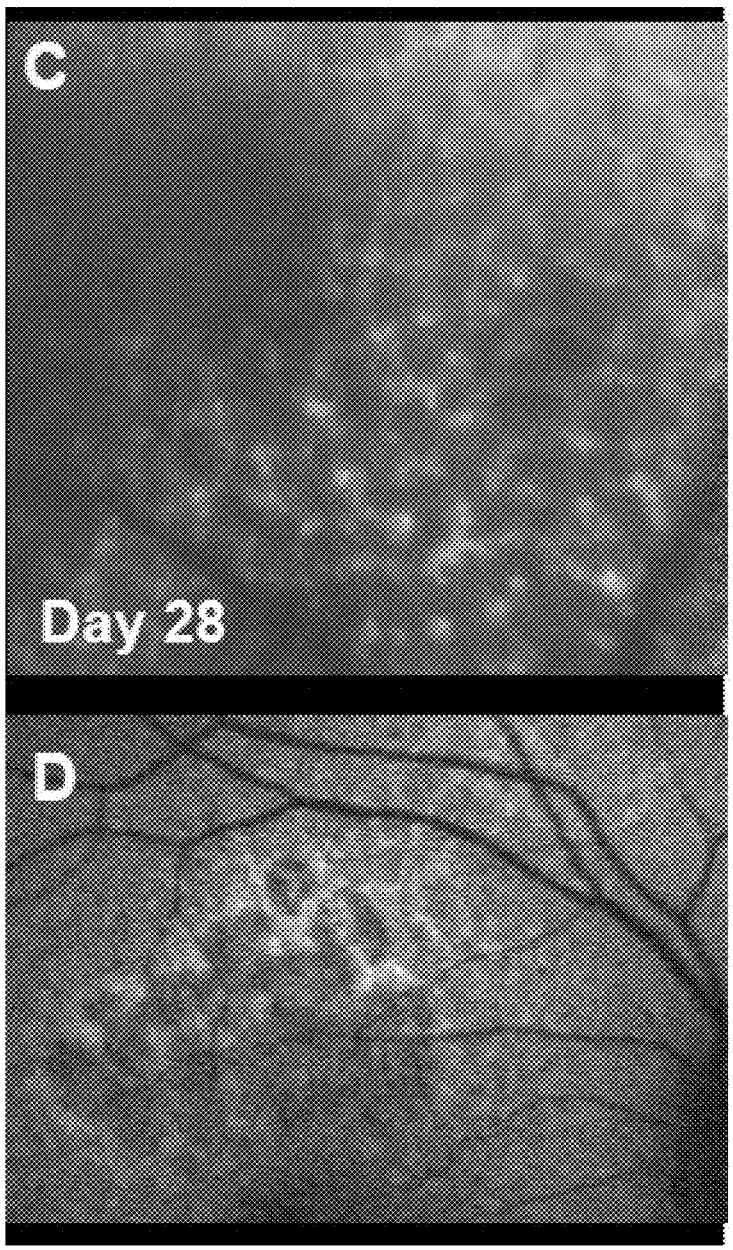

The present invention is based, in part, of the discovery of a modality for detecting and/or measuring and/or evaluating a blinding eye disease in a subject and/or an animal and the use of this method in the discovery and/or evaluation of candidate compounds for improved treatments of the blinding eye diseases. Specifically, inter alia, the present invention provides for an analytical method entitled delayed near infra-red analysis (DNIRA), and the use of this method in the generation of models for a blinding eye disease such as, for example, AMD and/or RPD. Additionally, the present invention pertains to methods of diagnosing specific forms of blinding eye disease, such as, for example, AMD and/or RPD and methods for treating AMD and/or RPD.

In one aspect, the invention provides a method for identifying whether a candidate compound is useful for the treatment of a blinding eye disease, comprising (a) administering an effective amount of a test compound to an animal whose eye comprises (i) a fluorescent compound in an amount effective to indicate the presence of a blinding eye disease in the animal and (ii) a toxin in an amount effective to induce atrophy of ocular tissue; (b) exposing the eye to light having a wavelength and intensity effective to cause the fluorescent compound to fluoresce; (c) comparing the eye's fluorescence pattern to a fluorescence pattern of an animal's eye that comprises the fluorescent compound and the toxin but not the test compound; and (d) selecting the test compound as a candidate compound if the result of the comparison of step (c) indicates that the test compound is useful for the treatment of a blinding eye disease.

In some embodiments, the blinding eye disease is AMD or RPD disease.

In some embodiments, the animal is a mouse, rat, or zebrafish.

In other embodiments, the fluorescent compound absorbs light at a wavelength of about 600 nm to about 900 nm and/or emits light at a wavelength of about 750 nm to about 950 nm. In a specific embodiment, the fluorescent compound is ICG. In still other embodiments, the fluorescence occurs in RPE cells.

In some embodiments, the toxin is sodium iodate. In other embodiments, the atrophy comprises necrosis of RPE cells. In other embodiments, the necrosis presents as patches.

In still other embodiments, the comparing occurs at least about 24 hours, or at least about 7 days, or at least about 30 days, or at least 60 days, or at least 90 days after administering the test compound.

In various embodiments, the exposing the eye to light comprises performing cSLO, FAF, DNIRA, or OCT. In various embodiments, the exposing the eye to light comprises white light, blue light, red-free light, near infra-red, or infra-red.

In various embodiments, the presence of a blinding eye disease is indicated by patterns of FAF within patches of RPE damage or loss or outer retinal loss. In various embodiments, the presence of a blinding eye disease is indicated by patterns of FAF that occur within, or adjacent to, or in proximity to, or distant from, or in the absence of patches of RPE damage or loss or outer retinal loss. In some embodiments, the patterns are one or more of curvilinear, ribbon-like, reticular, oval, circular, scalloped, halo, and target-like lesions. In various embodiments, the presence of a blinding eye disease is indicated by patterns of FAF within a border of patches of RPE damage or loss or outer retinal loss. In some embodiments, the patterns are one or more of curvilinear, ribbon-like, reticular, oval, circular, scalloped, halo, and target-like lesions. In various embodiments, the presence of a blinding eye disease is indicated by patterns of FAF that occur distant from, or in the absence of patches of RPE damage or loss or outer retinal loss. In some embodiments, the patterns are one or more of curvilinear, ribbon-like, reticular, oval, circular, scalloped, halo, and target-like lesions.

In various other embodiments, the presence of a blinding eye disease is indicated by cross-sectional patterns or transverse patterns. In some embodiments, the patterns are observed with OCT. In some embodiments, the patterns are RPE and/or outer retinal loss or mounds, triangles, peaks or spikes found in the sub-retinal space.

In still other embodiments, the methods further comprise the step of observing the eye prior to administering the test compound. In some embodiments, this observing establishes one or more pre-administration characteristics of the eye.

In yet another embodiment, the methods described herein comprise administering the fluorescent compound prior to administering the test compound. In still another embodiment, the methods described herein do not comprise administering (i) an additional amount of a fluorescent compound to the animal or (ii) a second fluorescent compound to the animal. In other embodiments, the methods described herein comprise administering the toxin prior to administering the test compound and/or administering the toxin prior to administering the fluorescent compound.

In still another embodiment, the methods described herein comprise administering (i) an additional amount of the toxin to the animal or (ii) a second toxin to the animal. In still another embodiment, the methods described herein comprise administering (i) an additional amount of the toxin to the animal, (ii) a second toxin to the animal, or (iii) a compound believed to influence the mechanism of action of the toxin. In some embodiments, the methods described herein comprise further comprise observing a reduction in the rate of formation, growth or expansion of patches of ocular tissue atrophy or patches of tissue loss.

In some embodiments, the candidate compound is useful for treating, preventing, or reducing the rate of pathogenesis of a blinding eye disease. In other embodiments, a plurality of candidate compounds is identified. In some embodiments, the methods described herein further comprise comparing the usefulness of the plurality of candidate compounds in the treatment of a blinding eye disease and selecting a lead compound based on the comparison.

In another aspect, the invention provides a method for treating or preventing dry AMD, comprising administering to a subject in need thereof an effective amount of a compound of Formula I:

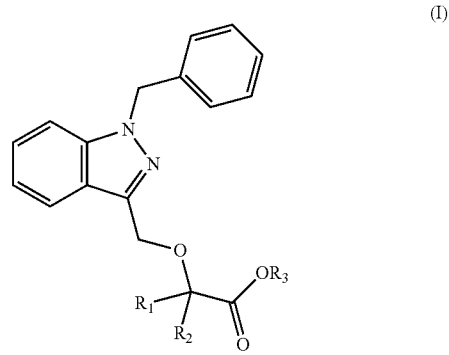

(I)

or a pharmaceutically acceptable salt thereof, wherein each of $R_1$ and $R_2$ is independently H or a $C_1$-$C_6$ alkyl and $R_3$ is H or a $C_1$-$C_6$ alkyl. In one embodiment, the compound of Formula I is bindarit.

In a further aspect, the invention provides a method for treating or preventing dry AMD, comprising administering to a subject in need thereof an effective amount of methotrexate or a pharmaceutically acceptable salt thereof.

In some embodiments, the methods further comprise administering an additional therapeutic agent. In various embodiments, the additional therapeutic agent is one or more of an anti-vascular endothelial growth factor (VEGF) agent, an angiotensin-converting enzyme (ACE) inhibitor, a peroxisome proliferator-activated receptor (PPAR)-gamma agonist or partial agonist, or combined PPAR-alpha/gamma agonist, a renin inhibitor, a steroid, and an agent that modulates autophagy.

In some embodiments, the dry AMD is identifiable by the presence of areas of hyper-fluorescent FAF in an eye of the subject and/or the presence of one or more areas of abnormally fluorescent FAF in an eye of the subject and/or by changes in one or more of blue spectrum fundus imaging, white-light fundus imaging, red-free fundus imaging, and OCT in an eye of the subject and/or by an increase (including a transient increase) in permeability across the subject's epithelial barrier between a choroid and a retina relative to an undiseased state and/or by a deformation of the outer retina, and/or deformation of the mid-retinal vasculature across the subject's epithelial barrier between a choroid and a retina relative to an undiseased state and/or by the presence of phagocytic immune cells across the subject's RPE relative to an undiseased state.

In some embodiments, the dry AMD is early stage AMD, or atrophic dry AMD.

In other embodiments, the subject is a human. In still other embodiments, the administering is effected orally or intra-vascularly, or intraocularly, or periocularly, or to the ocular surface.

In another aspect, the invention provides a method of treating RPD disease, comprising administering to a subject in need thereof an effective amount of a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl. In one embodiment, the compound of Formula I is bindarit.

In still another aspect, the invention provides a method of treating RPD disease, comprising administering to a subject in need thereof an effective amount of methotrexate or a pharmaceutically acceptable salt thereof.

In some embodiments, the methods described herein comprise reducing the amount of pseudodrusen in the subject and/or reducing the amount of pseudodrusen in any one of the foveal area, perifoveal area, juxtafoveal area, and extrafoveal area of the subject's eye. In other embodiments, the methods described herein comprise reducing the rates of progression to late disease, wherein the late disease is any one of choroidal neovascularization or geographic atrophy. In some embodiments, the methods described herein comprise reducing the rates of expansion of geographic atrophy.

In some embodiments, the methods described herein comprise administering an additional therapeutic agent. In various embodiments, the additional therapeutic is one or more of an anti-VEGF agent, an ACE inhibitor, a PPAR-gamma agonist or partial agonist, or combined PPAR-alpha/gamma agonist, a renin inhibitor, a steroid, and an agent that modulates autophagy.

In still other embodiments, the RPD disease is identifiable by the presence of one or more areas of distinct patterns of retinal imaging in the eye of a subject, wherein the retinal imaging is one or more of white light, red-free light, blue light, FAF, near infra-red (NIR), infra-red (IR), angiography, and DNIRA and/or the presence of one or more areas of abnormally-fluorescent FAF in the eye of a subject and/or an increase (including a transient increase) in permeability across the subject's epithelial barrier between a choroid and a retina relative to an undiseased state and/or a presence of phagocytic immune cells across the subject's RPE relative to an undiseased state.

In other embodiments, the subject is a human. In still other embodiments, the administering is effected orally or intra-vascularly, or intraocularly, or periocularly, or to the ocular surface.

In other embodiments, the invention provides for the use of compounds of Formula I, methotrexate, or their pharmaceutically acceptable salts, alone or in combination with an additional therapeutic, in the manufacture of a medicament useful for the treatment or prevention of one or more blinding eye diseases.

In yet another aspect, the invention provides a method for identifying a subject who has a blinding eye disease and is more likely than not to respond to treatment with an agent comprising determining whether the subject's eye has, or previously had, an increase (including a transient increase) in permeability across the epithelial barrier between a choroid and a retina of the eye relative to an undiseased state; wherein the increase in permeability indicates that the subject is more likely than not to respond to treatment with the agent; and wherein the agent is selected from methotrexate or a pharmaceutically acceptable salt thereof, or and a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl.

In one embodiment, the compound of Formula I is bindarit. In some embodiments, the blinding eye disease is one or more of dry AMD and RPD disease.

In still another aspect, the present invention provides a method for identifying a blinding eye disease subject who is more likely than not to respond to treatment with an agent comprising determining whether the subject's eye has a presence of phagocytic immune cells (optionally derived from within the retina or from the RPE) across the RPE relative to an undiseased state, wherein the presence of phagocytic immune cells indicates that the subject is more likely than not to respond to treatment with the agent; and wherein the agent is selected from methotrexate or a pharmaceutically acceptable salt thereof, or and a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl.

In one embodiment, the compound of Formula I is bindarit. In some embodiments, the blinding eye disease is one or more of dry AMD and RPD disease. In other embodiments, the presence of phagocytic immune cells is measured by DNIRA.

In another aspect, the invention provides a method for determining whether a blinding eye disease in a subject is responsive to treatment with an agent that inhibits the function of a subject's immune cells, comprising detecting a presence, detecting an absence, or measuring an amount of immune cells in the subject's eye, wherein the subject's eye fluoresces in response to light having a wavelength of about 600 nm to about 900 nm. In some embodiments, the light has a wavelength of about 400 nm to about 900 nm In some embodiments, the methods described herein further comprise administering to the subject an effective amount of a fluorescent compound, wherein the detecting or measuring occurs at least one day after the administration of the fluorescent compound. In some embodiments, the detecting or measuring occurs at least one day after administering to the subject an effective amount of a fluorescent compound.

In some embodiments, the methods described herein further comprise the step of detecting or measuring FAF in the eye of the subject. In some embodiments, the methods described herein further comprise the step of correlating an FAF pattern to the presence, absence, or amount of immune cells in the subject's eye.

In other embodiments, the blinding eye disease is AMD, central serous retinopathy (CSR) or RPD disease. In some embodiments, the subject is a human.

In various embodiments, the subject's eye fluoresces light having a wavelength of about 750 nm to about 950 nm. In some embodiments, the fluorescent compound is ICG.

In some embodiments, the detecting or measuring occurs at about one day, or about seven days, or at about thirty days after administration of the fluorescent compound.

In some embodiments, the methods described herein do not further comprise administering (a) an additional amount of the fluorescent compound or (b) a second fluorescent compound.

In other embodiments, the detecting or measuring comprises performing cSLO, FAF, DNIRA or OCT.

In some embodiments, the immune cells are cells of the subject's innate immune system and/or macrophage and/or microglial cells.

Definitions

The following definitions are used in connection with the invention disclosed herein. Unless defined otherwise, all technical and scientific terms used herein have the same meaning as commonly understood to one of skill in the art to which this invention belongs.

An "effective amount," when used in connection with a test compound and/or candidate compound is an amount that is effective for providing a measurable treatment, prevention, or reduction in the rate of pathogenesis of a blinding eye disease such as, for example, AMD and/or RPD.

An "effective amount," when used in connection with a fluorescent compound is an amount that allows optical detection.

An "effective amount," when used in connection with a compound of Formula I, methotrexate, or a pharmaceutically acceptable salt thereof, is an amount that is effective for treating or preventing dry AMD and/or RPD disease (e.g. providing a measurable treatment, prevention, or reduction in the rate of pathogenesis).

An "effective amount," when used in connection with another therapeutic agent is an amount that is effective for treating or preventing dry AMD and/or RPD disease (e.g. providing a measurable treatment, prevention, or reduction in the rate of pathogenesis) alone or in combination with a compound of Formula I, methotrexate, or a pharmaceutically acceptable salt thereof "In combination with" includes administration within the same composition and via separate compositions; in the latter instance, the other therapeutic agent is effective for treating or preventing a condition during a time when the agent a compound of Formula I, methotrexate, or a pharmaceutically acceptable salt thereof, exerts its prophylactic or therapeutic effect, or vice versa.

An "effective amount," when used in connection with a toxin, for example, sodium iodate, is an amount that is effective for inducing measurable atrophy of ocular tissue as described herein.

An agent is "useful for the treatment of a blinding eye disease" if the agent provides a measurable treatment, prevention, or reduction in the rate of pathogenesis of a blinding eye disease.

The term "blinding eye disease" refers to one of various ophthalmic diseases and includes diseases of the eye and the ocular adnexa. The term "blinding eye disease" includes, for example, disorders described herein (for instance, by way of non-limiting example, AMD and RPD).

The term "neovascularization" refers to new blood vessel formation in abnormal tissue or in abnormal positions.

The term "VEGF" refers to a vascular endothelial growth factor that induces angiogenesis or an angiogenic process, including, but not limited to, increased permeability. As used herein, the term "VEGF" includes the various subtypes of VEGF (also known as vascular permeability factor (VPF) and VEGF-A) that arise by, e.g., alternative splicing of the VEGF-A/VPF gene including $VEGF_{121}$, $VEGF_{165}$ and $VEGF_{189}$. Further, as used herein, the term "VEGF" includes VEGF-related angiogenic factors such as PlGF (placental growth factor), VEGF-B, VEGF-C, VEGF-D and VEGF-E, which act through a cognate VEFG receptor (i.e., VEGFR) to induce angiogenesis or an angiogenic process. The term "VEGF" includes any member of the class of growth factors that binds to a VEGF receptor such as VEGFR-1 (Flt-1), VEGFR-2 (KDR/Flk-1), or VEGFR-3 (FLT-4). The term "VEGF" can be used to refer to a "VEGF" polypeptide or a "VEGF" encoding gene or nucleic acid.

The term "anti-VEGF agent" refers to an agent that reduces, or inhibits, either partially or fully, the activity or production of a VEGF. An anti-VEGF agent can directly or indirectly reduce or inhibit the activity or production of a specific VEGF such as $VEGF_{165}$. Furthermore, "anti-VEGF agents" include agents that act on either a VEGF ligand or its cognate receptor so as to reduce or inhibit a VEGF-associated receptor signal. Non-limiting examples of "anti-VEGF agents" include antisense molecules, ribozymes or RNAi that target a VEGF nucleic acid; anti-VEGF aptamers, anti-VEGF antibodies to VEGF itself or its receptor, or soluble VEGF receptor decoys that prevent binding of a VEGF to its cognate receptor; antisense molecules, ribozymes, or RNAi that target a cognate VEGF receptor (VEGFR) nucleic acid; anti-VEGFR aptamers or anti-VEGFR antibodies that bind to a cognate VEGFR receptor; and VEGFR tyrosine kinase inhibitors.

The term "anti-RAS agent" or "anti-Renin Angiotensin System agent" refers to refers to an agent that reduces, or inhibits, either partially or fully, the activity or production of a molecule of the renin angiotensin system (RAS). Non-limiting examples of "anti-RAS" or "anti-Renin Angiotensin System" molecules are one or more of an angiotensin-converting enzyme (ACE) inhibitor, an angiotensin-receptor blocker, and a renin inhibitor.

The term "steroid" refers to compounds belonging to or related to the following illustrative families of compounds: corticosteroids, mineralicosteroids, and sex steroids (including, for example, potentially androgenic or estrogenic or anti-andogenic and anti-estrogenic molecules). Included among these are, for example, prednisone, prednisolone, methyl-prednisolone, triamcinolone, fluocinolone, aldosterone, spironolactone, danazol (otherwise known as OPTINA), and others.

The terms "peroxisome proliferator-activated receptor gamma agent," or "PPAR-γ agent," or "PPARG agent," or "PPAR-gamma agent" refers to agents which directly or indirectly act upon the peroxisome proliferator-activated receptor. This agent may also influence PPAR-alpha, "PPARA" activity.

The term "an agent that modulates autophagy" refers to a modulator of cell survival, cell death, survival, autophagy, proliferation, regeneration, and the like.

The term "monocyte chemotactic protein-1," or "MCP-1" refers to a member of the small inducible gene (SIG) family that plays a role in the recruitment of monocytes to sites of injury and infection.

The term "alkyl," as used herein unless otherwise defined, refers to a straight or branched saturated group derived form the removal of a hydrogen atom from an alkane. Representative straight chain alkyl groups include, but are not limited to, -methyl, -ethyl, -n-propyl, -n-butyl, -n-pentyl, and n-hexyl. Representative branched alkyl groups include, but are not limited to, isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl.

As used herein, "a," "an," or "the" can mean one or more than one. Further, the term "about" when used in connection with a referenced numeric indication means the referenced numeric indication plus or minus up to 10% of that referenced numeric indication. For example, the language "about 50" covers the range of 45 to 55.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

DNIRA

In various embodiments, the present invention involves optical imaging, using various techniques that are known in the art. For example, such techniques include, but are not limited to cSLO, FAF, angiography, OCT, including three dimensional reconstructions of such. In various embodiments of the invention, exposing an eye to light comprises performing cSLO, FAF, DNIRA, angiography or OCT. In various embodiments, the imaging is DNIRA. In various embodiments, combinations of any of the above techniques may be used.

For DNIRA, a compound suitable for fluorescence detection including a near-infrared (NIR) dye, such as, ICG when given at non-toxic doses, can label the RPE and therefore make it visible when viewed using the ICG excitation/emission filters in the days or weeks thereafter. Importantly, this visualization in the days and weeks thereafter may be without re-administration of dye. Accordingly, in some aspects, a central component of the DNIRA technique lies in its timing. This is distinct from the present usage of ICG or other angiographic dyes that are viewed immediately after injection, during the transit phase, or in the immediate minutes to hours following injection, to determine the intravascular localization of dye and its immediate extravasation.

In one embodiment, DNIRA may involve administration of a compound suitable for fluorescence detection, by way of non-limiting example, ICG (and, optionally, angiography) at about one or more days prior to administration with a toxin or other agent that causes geographic atrophy expansion (e.g. NaIO$_3$) and optionally followed by, at about 1 or more days (or about one week, or about one month, or about three months), an additional amount of NaIO$_3$ or another agent that causes geographic atrophy expansion. For example, the other challenge that causes geographic atrophy expansion (e.g. as an initial, or second, or third, or fourth administration) may be a modulator of cell survival, cell death, survival, autophagy, proliferation, regeneration, and the like.

Expansion of geographic atrophy is a U.S. Food and Drug Administration (FDA) approved primary outcome for clinical trial design, and, accordingly, this invention makes possible observation of geographic atrophy, in particularly the expansion of geographic atrophy, in an animal model, thus permitting correlation between pre-clinical disease models and clinical trial design. The inability to clearly identify the geographic atrophy, or expansion of geographic atrophy, in an eye of an animal prior to the present invention has precluded direct correlation between pre-clinical studies and clinical observation.

In some embodiments, the compound suitable for fluorescence detection is suitable for imaging with various wavelengths of fluorescence. In some embodiments, these wavelengths range from visible light to infrared, e.g., 390 nm to 1 mm, including, for example, blue light, white light, and near-infrared. In some embodiments, the dye is a near-infrared dye. In some embodiments, the dye is ICG.

In some embodiments, DNIRA is performed (and/or delayed near infrared fluorescence (DNIRF) is observed) at about 1 day, or about 2 days, or about 3 days, or about 4 days, or about 5 days, or about 6 days, or about 7 days, or about 10 days, or about 14 days, or about 21 day after the administration. In some embodiments, the DNIRA is performed at least 1 day after the administration, or at least 2 days, or at least 3 days, or at least 4 days, or at least 5 days, or at least 6 days, or at least 7 days, or at least 10 days, or at least 14 days, or at least 21 days after the administration. n other embodiments, the DNIRA is performed at least about 24 hours, or at least about 7 days, or at least about 30 days, or at least 60 days, or at least 90 days after administering. In other embodiments, the DNIRA is performed at least about 2 months, or about 3 months, or about 4 months, or about 5 months, or at a maximum about 6 months after administering. In some embodiments, the DNIRA is not performed during the transit stage (i.e. the first passage of dye as it flows through the ocular blood vessels and into the ocular tissue) or minutes thereafter.

In some embodiments, the visualization is effected using a cSLO. In some embodiments, the visualization is effected using white light and appropriate filters. In some embodiments, the ICG excitation/emission filters are 795 nm (excitation)/810 nm (emission) filters. In some embodiments, the ICG excitation/emission filters are about 795 nm (excitation)/about 810 nm (emission) filters.

The RPE is a critical epithelial monolayer that serves a "nurse-cell" function for an eye's specialized photoreceptors, the rods and cones. Blinding eye diseases, such as, for example, AMD and RPD, are, without wishing to be bound by theory, causally linked in part to abnormalities of the RPE.

DNIRA makes it possible to clearly identify the RPE layer in vivo in an eye of an animal. Further, the leading technique used to detect the RPE in the human eye, FAF, is ineffective or poorly effective, possibly owing to a relative paucity of fluorophores such as lipofuscin. FAF imaging in the human eye is performed using the blue spectrum of non-coherent light in the presence of stimulation/emission filters, or coherent blue light, and can identify areas of absent RPE (e.g. hypo-fluorescent signal) or abnormal RPE (e.g. hyperfluorescent signal). The inability to clearly identify the RPE in an eye of an animal, in the absence, has precluded direct correlation between pre-clinical studies and clinical observation.

Accordingly, in various aspects of the present invention, methods to make visible the RPE layer, such as, for example, DNIRA, in an eye of an animal for pre-clinical investigation of blinding eye diseases are provided.

Further, as described herein, DNIRA, or variations thereof, allow for visualization of fluorescent immune cells in the eyes of an animal. In some embodiments DNIRA may optionally not comprise toxin administration.

Further, as described herein, DNIRA, or variations thereof, allow for visualization of fluorescent immune cells in the eyes of human subject. In some embodiments with a human subject DNIRA may not comprise toxin administration.

Blinding Eye Diseases

A blinding eye disease refers to one of various ophthalmic diseases and includes diseases of the eye and the ocular adnexa.

In various embodiments, a blinding eye disease is evaluated and/or identifiable using DNIRA or a technique known in the art. Illustrative techniques include: cSLO, FAF, OCT (including with cross-sectional, three-dimensional and en face viewing), SD-OCT (with cross-sectional, three-dimensional and en face viewing), angiography, or other imaging modalities including other wavelengths of fluorescence. In some embodiments, these wavelengths range from blue to infrared, e.g., 390 nm to 1 mm, including, for example, blue light, white light, red-free, near infra-red, infrared.

In various embodiments, a blinding eye disease is evaluated and/or identifiable by patterns of FAF within patches of RPE damage or loss or outer retinal loss. In some embodiments, the patterns are one or more of curvilinear, ribbon-like, reticular, oval, circular, scalloped, halo, and target-like lesions.

In various embodiments, a blinding eye disease evaluated and/or identifiable by patterns of FAF within a border of patches of RPE damage or loss or outer retinal loss. In some embodiments, the patterns are one or more of curvilinear, ribbon-like, reticular, oval, circular, scalloped, halo, and target-like lesions.

In various other embodiments, a blinding eye disease is evaluated and/or identifiable by cross-sectional patterns or transverse patterns. In some embodiments, the patterns are observed with OCT. In some embodiments, the patterns are RPE and/or outer retinal loss or mounds, triangles, peaks or spikes found in the sub-retinal space.

In other embodiments, a blinding eye disease is evaluated and/or identifiable by the presence of areas of hyper-fluorescent FAF in an eye of the subject and/or the presence of one or more areas of abnormally fluorescent FAF in an eye of the subject and/or by changes in one or more of blue spectrum fundus imaging, white-light fundus imaging, red-free fundus imaging, and OCT in an eye of the subject and/or by an increase (e.g. a transient increase) in permeability across the subject's epithelial barrier between a choroid and a retina relative to an undiseased state and/or by a deformation of the outer retina, and/or deformation of the mid-retinal vasculature across the subject's epithelial barrier between a choroid and a retina relative to an undiseased state and/or by the presence of phagocytic immune cells across the subject's RPE relative to an undiseased state. Illustrative changes include differences in an imaging pattern in the same of different subject and/or animal at two different time points and/or experimental or clinical conditions. For example, changes can encompass changes in imaging data between two evaluations of the same subject and/or animal and/or changes in imaging data between a first subject and/or animal and the imaging data of a second subject and/or animal.

In still other embodiments, a blinding eye disease is evaluated and/or identifiable by the presence of one or more areas of distinct patterns of retinal imaging in the eye of a subject, wherein the retinal imaging is one or more of white light, red-free light, blue light, FAF, near infra-red (NIR), infra-red (IR), angiography, and DNIRA and/or the presence of one or more areas of abnormally-fluorescent FAF in the eye of a subject and/or an increase (e.g. a transient increase) in permeability across the subject's epithelial barrier between a choroid and a retina relative to an undiseased state and/or a presence of phagocytic immune cells across the subject's RPE relative to an undiseased state.

In various embodiments, the blinding eye disease is AMD. AMD is the leading cause of blindness in the developed world. Early AMD is characterized by the accumulation of drusen, the hallmark of disease, while geographic atrophy (GA) and choroidal neovascularization (CNVM) are the blinding complications of late non-exudative (so-called "dry" or atrophic) and exudative (so-called "wet" or neovascular) disease, respectively. Anti-VEGF therapy has revolutionized treatment of wet AMD, but represents just 12-15% of all AMD cases. Though vitamin supplementation can slow the rates of progression no treatments exist for dry AMD.

In various embodiments, the blinding eye disease is early non-exudative or "dry" AMD. Early non-exudative or "dry" AMD can be characterized by drusen accumulation and associated features such as pigmentation change, or RPE detachments. Late, or advanced dry AMD can be characterized by patchy atrophy of the RPE and overlying photoreceptors. These patches are visualized clinically as so-called "window defects" and are known as areas of "geographic atrophy."

In various embodiments, the blinding eye disease is wet AMD. Wet AMD is characterized by the growth of new blood vessels beneath the retina or RPE which can bleed and leak fluid, resulting in a rapid and often severe loss of central vision in the majority cases. This loss of central vision adversely affects one's everyday life by impairing the ability to read, drive and recognize faces. In some cases, the macular degeneration progresses from the dry form to the wet form.

In one embodiment, the blinding eye disease is exudative or wet AMD. In one embodiment, the blinding eye disease is associated with choroidal neovascularization (CNVM).

In some embodiments, AMD is detected or evaluated using FAF, an in vivo imaging method for the spatial mapping (e.g. two-dimensional, en face, and the like) of endogenous, naturally or pathologically occurring fluorophores of the ocular fundus. In some embodiments, without wishing to be bound by theory, FAF imaging allows visualization of the RPE in vivo and can help to better understand its metabolic alterations in the pathogenesis of chorioretinal disorders and retinal pigment epitheliopathies. FAF is well known in the art (see, e.g., Bellman et al. *Br J Ophthalmol* 2003 87: 1381-1386, the contents of which are hereby incorporated by reference).

In some embodiments, AMD and/or RPE damage or loss may also be visualized by other wavelengths of light, including white light, blue light, near infra-red, infra-red, and be visible as a "window defect" through which the choroid can be viewed. In some embodiments, AMD and/or RPE damage or loss may also be visualized by cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infrared, e.g., 390 nm to 1 mm, including, for example, blue light, white light, red-free, near infra-red, or infrared).

In some embodiments, in late dry AMD, areas of geographic atrophy are clearly visualized as areas of hypofluorescent, or dark, FAF. In some embodiments, these represent areas where RPE is lost.

In some embodiments, dry AMD is identifiable by the presence of areas of hyper-fluorescent FAF in an eye of the subject. In some embodiments, the dry AMD identifiable by the presence of areas of hyper-fluorescent FAF is progressing early or late dry AMD. In some embodiments, hyper-fluorescent FAF refers to an increased fluorescence that may be caused by an enhanced visualization of a normal density of lipofuscin or lipofuscin-like materials or an increase in the lipofuscin content of the tissues. Lipofuscin comprises a mix of proteins, with or without lipid, the components of which fluoresce under blue-light illumination of the appropriate wavelengths. Lipofuscin-like fluorescence may also occur in this spectrum, and could be due to molecules other than lipofuscin and its constituents.

Lipofuscin-like fluorescence may occur in RPE cells, and cells other than RPE cells such as, for example, cells of the immune system (e.g. phagocytic immune cells).

In other embodiments, the AMD is identifiable by the presence of abnormal patterns of FAF in an eye of the subject. In some embodiments, abnormal fluorescent FAF refers to deviation from the normal fluorescent FAF pattern observed in a subject's eye. In normal FAF, using the cSLO or modified fundus cameras, the optic nerve head is dark (black) due to the absence of RPE (and hence no lipofuscin) and the blood vessels are also dark because they block fluorescence from the underlying RPE monolayer. In the central macular area, the FAF signal is reduced by absorption of blue light by luteal pigment. These characteristics of normal blue-light FAF may be considered when evaluating for the presence of abnormal fluorescence.

In some embodiments, hyperfluorescent FAF associated with AMD and other blinding diseases, may show two-dimensional spatial patterns, which may be complex. In some studies, these patterns of hyperfluorescent FAF correlate with rates of disease progression from early to late (either neovascular or atrophic) disease. These patterns are understood in the art (see, e.g., Schmitz-Valckenberg et al. *Survey of Ophthalmology.* 2009 January-February; 54(1): 96-117; Bindewald et al. *British Journal of Ophthalmology.* 2005 July; 89(7):874-8; Holz et al. *Am. J Ophthalmology.* 2007 March; 143(3):463-72, the contents of which are hereby incorporated by reference in their entireties).

In some embodiments, the dry AMD is early stage AMD, or atrophic dry AMD.

In some embodiments, dry AMD is in its late stage and characterizable by the presence of areas of hyper-fluorescent or abnormally-fluorescent FAF in areas bordering and/or adjacent to (in the so-called junctional zone) pre-existent geographic atrophy.

In some embodiments, dry AMD is in its late stage and characterizable by the presence of areas of hyper-fluorescent or abnormally-fluorescent FAF in the absence of pre-existent geographic atrophy. In these embodiments, without wishing to be bound by theory, it may predict future loss of the RPE.

In some embodiments, dry AMD in both early and late stage is characterizable by the presence of immune cells (e.g. phagocytic immune cells). The presence of immune cells can be surmised from post-enucleation or post-mortem ocular samples. As described herein, in some embodiments, the presence of immune cells is assessed using DNIRA.

In some embodiments, patterns such as "diffuse trickling" may be evaluated, treated or prevented using methods disclosed herein. Diffuse trickling patterns are known in the art (see, e.g., Schmitz-Valckenberg et al. *Survey of Ophthalmology.* 2009 January-February; 54(1):96-117; Bindewald et al. *British Journal of Ophthalmology.* 2005 July; 89(7): 874-8; Holz et al. *Am. J Ophthalmology.* 2007 March; 143(3):463-72, the contents of which are hereby incorporated by reference in their entireties).

In some embodiments, the dry AMD is identifiable by an increase (e.g. a transient increase) in permeability across the subject's epithelial barrier between a choroid and a retina, relative to an undiseased state. This is distinct from vascular (endothelial) permeability. For example, this may be seen using angiography.

In some embodiment, RPE toxicity, RPE loss, and the dry AMD are identifiable using DNIRA, e.g. with sodium iodate ($NaIO_3$). Areas analogous to geographic atrophy can be detected by, for example, tissue analysis (for example, by observing the loss of an RPE cell marker such as RPE65 and/or the loss of binucleate cell staining), and/or in vivo, using DNIRA, of $NaIO_3$-treated-eyes. In some embodiments, RPE toxicity, RPE loss and the dry AMD are identifiable using FAF which shows a hyperfluorescent FAF signal, which may be complex, within the area of imminent tissue loss and/or at its margins. This complex hyperfluorescent FAF signal develops, in the days or weeks after $NaIO_3$ treatment, into a pattern of FAF, which can be complex and can include, but is not limited to ribbon-like, curvilinear, pisciform, scalloped, interlacing, branching, or reticular hyperfluorescence. Such patterns mimic those found in clinical dry AMD. Such FAF may also be hypofluorescent.

Further, using angiography alone, or as part of DNIRA, angiography performed immediately prior to, or coincident with, the emergence of the areas of altered FAF may demonstrate an increase (including a transient increase) in permeability across the epithelial barrier between choroid and retina (such as, for example, observed by leakage of dyes that may be injected prior to imaging; such dyes include ICG). This barrier normally includes the inner choroid, Bruch's Membrane, the RPE cells, and, possibly, the configuration of the outer photoreceptors in conjunction with the RPE and the outer limiting membrane. Without wishing to be bound by theory, a transient breakdown of this specialized epithelial barrier may underlie a sequence of events thereafter including folding, undulation, or deformation of the outer retina, photoreceptor layer, and/or movement/migration of inflammatory cells from the choroid to the subretinal space. However, in some embodiments, this phase may be transient and resolved, or subclinical in its extent.

In some embodiments, the dry AMD is identifiable by a presence (e.g. an influx) of immune (e.g. phagocytic immune cells or innate immune cells) cells across the subject's retinal pigment epithelium (RPE) relative to an undiseased state. When there is movement/migration of inflammatory cells from the choroid to the subretinal space, or inner retina to outer retina or subretinal space, such cells may be identified in enucleated eyes or excised tissue by staining methods known in the art. In the $NaIO_3$ model, Iba1 staining may be used to detect activated cells of the immune system. Further, the presence of these cells may be confirmed by comparison with, for example, $NaIO_3$ preparations in which monocyte/macrophage depletion has been undertaken. Such depletion is known in the art and may be achieved by treatment with, for example, gadolinium chloride (GAD) or clodronate. In some embodiments, the presence (e.g. an influx) of immune cells is measured and/or determined, in vivo, by use of DNIRA. Prior to the present invention, such in vivo visualization was not possibly in the clinical setting.

Further, macrophages, an example of an immune cell that may be identified in the cells of a subject, may be classified by subsets: classically (M1) or alternatively (M2) activated macrophages (see, e.g., Laskin, *Chem Res Toxicol.* 2009 August 17; 22(8): 1376-1385, the contents of which are hereby incorporated by reference in their entireties). Without wishing to be bound by theory, M1 macrophages are activated by standard mechanisms, such as IFNγ, LPS, and TNFα, while M2 macrophages are activated by alternative mechanisms, such as IL-4, IL-13, IL-10, and TGFβ. Without wishing to be bound by theory, M1 macrophages display a cytotoxic, proinflammatory phenotype, while M2 macrophages, suppress some aspects of immune and inflammatory responses and participate in wound repair and angiogenesis.

In some embodiments, the invention comprises the inhibition, modulation or polarization of one or more of M1 and M2 macrophages.

In some embodiments, the dry AMD is identifiable by the changes in one or more of blue spectrum fundus imaging, white-light fundus imaging, red-free fundus imaging, and OCT in an eye of the subject. In some embodiments, the dry AMD is identifiable by the changes in one or more of cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infrared, e.g., 390 nm to 1 mm, including, for example, blue light, white light, red-free, near infra-red, or infrared). Illustrative changes include differences in an imaging pattern in the same of different subject and/or animal at two different time points and/or experimental or clinical conditions. For example, changes can encompass changes in imaging data between two evaluations of the same subject and/or animal and/or changes in imaging data between a first subject and/or animal and the imaging data of a second subject and/or animal.

In some embodiments, the AMD is identifiable by OCT. In some embodiments, cross-sectional images show the presence of shallow mounds, or pyramidal or spike-like signals, in the subretinal space. Three-dimensional or en face OCT imaging reveals ribbon-like or curvilinear, oval, circular, halo or target-like signals. In some embodiments, cross-sectional patterns or transverse patterns are observed and the cross-sectional or transverse patterns comprise RPE and/or outer retinal loss (atrophy) or mounds, triangles, peaks or spikes found in the sub-retinal space. In various embodiments, these features are indicative of AMD.

The invention further provides methods for treatment or prevention of RPD disease, also known as, but not limited to, the following: "reticular drusenoid disease," "pseudoreticular drusen," and "drusenoid macular disease," or "disease characterized by the presence of subretinal drusenoid deposits."

In some embodiments, the RPD disease is that in which pseudodrusen material is reduced or eradicated or the accumulation and/or expansion of which is slowed upon treatment. In some embodiments, the invention provides a method for treating RPD disease in which the pseudodrusen are reduced or eradicated upon treatment in the foveal area and/or perifoveal area and/or juxtafoveal area of a subject's eye.

In some embodiments, the invention further provides methods for treatment or prevention of RPD disease in which the rates of progression from early to late disease are reduced. Late disease can include, for example, choroidal neovascularization or geographic atrophy In some embodiments, the invention further provides methods for treatment or prevention of RPD disease in which the rates of expansion of geographic atrophy are reduced.

In some embodiments, the RPD disease is identifiable by FAF or other imaging modalities including other wavelengths of fluorescence. In some embodiments, these wavelengths range from blue to infrared, e.g., 390 nm to 1 mm, including, for example, blue light, white light, near-infrared, and infra-red.

In some embodiments, the RPD disease is identifiable by the presence of areas of hyper- and/or abnormal-fluorescent FAF or other imaging modalities including other wavelengths of fluorescence. In some embodiments, these wavelengths range from blue to infrared e.g., 390 nm to 1 mm, including, for example, blue light, white light, near-infrared and infra-red. In some embodiments, the RPD disease is identifiable by using DNIRA.

In some embodiments, the RPD disease is identifiable using at least one of, or at least two of, or at least three of, or at least four of white light, blue light, FAF, and near infrared and infrared. In a specific embodiment, the RPD disease is identifiable by blue light.

In some embodiments, the RPD disease is identifiable by OCT. In some embodiments, cross-sectional images show the presence of shallow mounds, or pyramidal or spike-like signals, in the subretinal space. Three-dimensional or en face OCT imaging reveals ribbon-like or curvilinear, oval, circular, halo or target-like signals.

In some embodiments, the RPD is identifiable by an increase (e.g. a transient increase) in permeability across the subject's epithelial barrier between a choroid and a retina, relative to an undiseased state. This is distinct from vascular (endothelial) permeability. For example, using DNIRA, which comprises, for example, a sodium iodate ($NaIO_3$) model of RPE toxicity, geographic areas of RPE damage or loss can be formed that can be detected by, for example, tissue analysis (for example, by observing the loss of an RPE cell marker such as RPE65 and/or the loss of binucleate cell staining). Further FAF imaging of $NaIO_3$-treated RPE shows a hyperfluorescent FAF signal, which may be complex, within the area of imminent tissue loss and/or at its margins. This hyperfluorescent FAF signal develops, in the days or weeks after $NaIO_3$ treatment, into a pattern, which can be complex, of FAF that includes, but is not limited to ribbon-like, curvilinear, pisciform, scalloped, interlacing, branching, or reticular hyperfluorescence. Such patterns mimic those found in clinical RPD.

Further, in DNIRA, angiography performed immediately prior to, or coincident with, the emergence of the areas of altered FAF demonstrates an increase (including a transient increase) in permeability across the epithelial barrier between choroid and retina (such as observed by leakage of dyes that may be injected prior to imaging; such dyes include ICG). This barrier normally includes the inner choroid, Bruch's Membrane, the RPE cells, and, possibly, the configuration of the outer photoreceptors in conjunction with the RPE and the outer limiting membrane. Without wishing to be bound by theory, a transient breakdown of this specialized epithelial barrier may be permissive for the sequence of events thereafter including folding, undulation, or deformation of the photoreceptor layer. However, in some embodiments, this phase may be transient and resolved, or subclinical in its extent.

In some embodiments, the RPD is identifiable by a presence (e.g. an influx) of immune cells (e.g. phagocytic immune cells) across the subject's retinal pigment epithelium (RPE) relative to an undiseased state. In some embodiments, presence (e.g. an influx) of immune cells is detected and/or measured with DNIRA. When there is movement/migration of inflammatory cells from the choroid to the subretinal space, or inner retina to outer retina or subretinal space, such cells may be identified by staining, as is known in the art. For example, using a $NaIO_3$ model, Iba1 staining may be used to detect activated phagocytic cells of the immune system. Further, the presence of these cells may be confirmed by comparison with $NaIO_3$ preparations in which monocyte/macrophage depletion has been undertaken. Such depletion is known in the art and may be achieved by treatment with, for example, gadolinium chloride (GAD) or clodronate. Further, macrophages, an example of a phagocytic immune cell, that are identified in the cells of a subject, may be classified by subsets: classically (M1) or alternatively (M2) activated macrophages (see, e.g., Laskin, *Chem Res Toxicol.* 2009 August 17; 22(8): 1376-1385, the contents of which are hereby incorporated by reference in their entireties). Without wishing to be bound by theory, M1 macrophages are activated by standard mechanisms, such as IFNγ, LPS, and TNFα, while M2 macrophages are activated by alternative mechanisms, such as IL-4, IL-13, IL-10, and TGFβ. Without wishing to be bound by theory, M1 macrophages display a cytotoxic, proinflammatory phenotype, while M2 macrophages, suppress some aspects of immune and inflammatory responses and participate in wound repair and angiogenesis. For example, the present invention, in some embodiments, comprises the inhibition, modulation or polarization of one or more of M1 and M2 macrophages.

In some embodiments, the RPD disease is identifiable by the changes in one or more of blue spectrum fundus imaging, white-light fundus imaging, red-free fundus imaging, and OCT in an eye of the subject. In some embodiments, the RPD disease is identifiable by the changes in one or more of cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infrared, e.g., 390 nm to 1 mm, including, for example, blue light, white light, red-free, near infra-red, or infrared). Illustrative changes include differences in an imaging pattern in the same of different subject and/or animal at two different time points and/or experimental or clinical conditions. For example, changes can encompass changes in imaging data between two evaluations of the same subject and/or animal and/or changes in imaging data between a first subject and/or animal and the imaging data of a second subject and/or animal.

In another embodiment, the blinding eye disease is LORDs (late onset retinal degeneration) or retinal degeneration associated with c1qTNF5 deficiency or its corresponding gene mutation, or another maculopathy, including, but not limited to, Stargart disease, pattern dystrophy, as well as retinitis pigmentosa (RP) and related diseases. In one embodiment, the maculopathy is inherited.

In other embodiments, the blinding eye disease is an idiopathic disorder that may, without wishing to be bound by theory, be characterized by retinal inflammation, with or without accompanying macular degeneration, including, but not limited to, white-dot syndromes (e.g. serpiginous chorioretinopathy, serpiginous retinopathy, acute posterior multifocal placoid pigment epitheliopathy (APMPPE), multiple evanescent white dot syndrome (MEWDS), acute zonal occult outer retinopathy (AZOOR), punctate inner choroidopathy (PIC), and diffuse subretinal fibrosis (DSF)).

In other embodiments, the blinding eye disease is central serous retinopathy (CSR). CSR is a fluid detachment of macula layers from their supporting tissue. CSR is often characterizable by the leak and accumulation of fluid into the subretinal or sub-RPE space. Without wishing to be bound by theory, the leak and accumulation of fluid may occur because of small breaks in the RPE.

In some embodiments, one or more of the blinding eye diseases are identifiable by the presence of areas of hyper- and/or abnormal-fluorescent FAF, or other wavelengths of light from 350 nm to 1,000 nm. In some embodiments, one or more of the blinding eye diseases are identifiable using DNIRA.

In some embodiments, one or more of the blinding eye diseases are identifiable by, for example, cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infrared, e.g., 390 nm to 1 mm, including, for example, blue light, white light, red-free, near infra-red, or infrared).

In some embodiments, the blinding eye disease may be of a certain stage or progression. In some embodiments, the blinding eye disease may be incipient, emerging, quiescent, advancing or active.

In addition to treating pre-existing blinding eye diseases, the present invention comprises prophylactic methods in order to prevent or slow the onset of these disorders. In prophylactic applications, an agent can be administered to a subject susceptible to or otherwise at risk of a particular blinding eye disease. Such susceptibility may be determined by, for example, familial predisposition, genetic testing, risk factor analysis, blood or other cytokine or biomarker levels, and ocular examination, which can include multi-modal analysis such as FAF, blue light, white light, red-free, near infra-red, infrared, DNIRA, etc. Such susceptibility may also be determined by, for example, detection by OCT, with cross-sectional, three-dimensional and en face viewing.

In addition to treating defined, known blinding eye diseases, the present invention comprises particular patterns of in vivo imaging using light at wavelengths ranging from 300 to 1,000 nm, including white light, blue light, FAF, infra-red, near infra-red, DNIRA or by OCT, with cross-sectional, three-dimensional and en face viewing. In applications against particular patterns of in vivo imaging, an agent can be administered to a subject with, susceptible to, or otherwise at risk of a particular blinding disease. Such diagnosis or susceptibility may be determined by, for example, ophthalmic examination, familial predisposition, genetic testing, risk factor analysis, and blood or other cytokine or biomarker levels, which can include multi-modal analysis such as FAF, blue light, white light, red-free, near infra-red, infrared, DNIRA, etc. Such susceptibility may also be determined by, for example, detection by OCT, with cross-sectional, three-dimensional and en face viewing.

Agents of the Invention

In various aspects, the present invention provides for the identification and use of a candidate compound and/or test compound. In embodiments providing for identification and use of a candidate compound and/or test compound, the candidate compound and/or test compound may be chemical, molecule, compound, biologic (e.g. an antibody or peptide), drug, pro-drug, cellular therapy, low molecular weight synthetic compound, or a small molecule drug. In some embodiments, the candidate compound and/or test compound is selected from a library of compounds known in the art. In some embodiments, the candidate compound is useful for treating a blinding eye disease, preventing a binding eye disease, or reducing the rate of pathogenesis of a blinding eye disease.

In various aspects, the present invention provides for a method for treating or preventing dry AMD and/or RPD. In some embodiments, a compound of Formula I, methotrexate, or a pharmaceutically acceptable salt thereof, is also administered with an additional therapeutic agent, including, for example, one or more of an anti-VEGF agent, an ACE inhibitor, a PPAR-gamma agonist or partial agonist, a renin inhibitor, a steroid, and an agent that modulates autophagy, as well as a semapimod, a MIF inhibitor, a CCR2 inhibitor, CKR-2B, a 2-thioimidazole, CAS 445479-97-0, CCX140, clodronate, a clodonate-liposome preparation or gadolinium chloride.

In various aspects, the present invention provides for identifying a blinding eye disease subject who is more likely than not to respond to treatment with an agent (an "agent of the invention") and/or determining whether a blinding eye disease in a subject is responsive to treatment with an agent.

In some embodiments, an agent of the invention is a compound of Formula I:

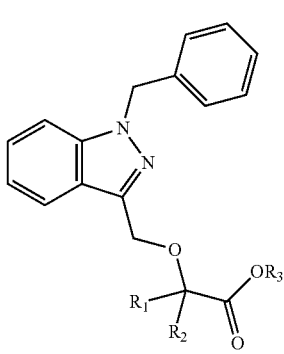

(I)

or a pharmaceutically acceptable salts thereof, wherein each of $R_1$ and $R_2$ is independently H or a $C_1$-$C_6$ alkyl and $R_3$ is H or a $C_1$-$C_6$ alkyl.

In various embodiments, $R_1$ and $R_2$ are independently hydrogen, methyl or ethyl.

In some embodiments $R_1$ and $R_2$ are independently methyl or ethyl.

In some embodiments $R_1$ and $R_2$ are methyl.

In some embodiments $R_3$ is hydrogen, methyl or ethyl.

In some embodiments $R_3$ is hydrogen.

In some embodiments, particularly where $R_3$ is hydrogen, the compounds of Formula I are in the form of a pharmaceutically acceptable salt.

In some embodiments $R_1$ and $R_2$ are methyl and $R_3$ is hydrogen. In such embodiments, the compound of Formula I is 2-((1-benzylindazol-3-yl) methoxy)-2-methyl propionic acid, also known as 2-methyl-2-[[1-(phenylmethyl)-1H-indazol-3yl]methoxy]propanoic acid. Such a compound is commonly known as bindarit and has the following structure:

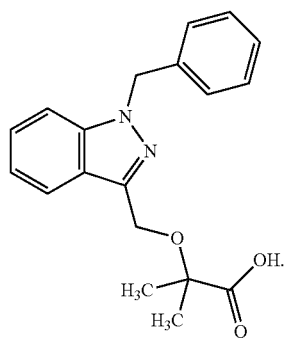 [SMILES: CC(C)(OCc1nn(Cc2ccccc2)c2ccccc12)C(=O)O]

Synthesis of bindarit is described in detail in U.S. Pat. No. 4,999,367, which is hereby incorporated by reference in its entirety.

Bindarit is an inhibitor of MCP-1 production in vitro and in vivo and, without wishing to be bound by theory, its beneficial effects in animal models of inflammation may be related to this anti-MCP-1 activity (see Mirolo, et al. *Eur Cytokine Netw* 2008; 19:119-122). Bindarit has also been shown to selectively inhibit the production of MCP-2 and MCP-3 (see Mirolo, et al. *Eur Cytokine Netw* 2008; 19:119-122).

In some embodiments, an agent of the invention is methotrexate or a pharmaceutically acceptable salt thereof. Methotrexate has the structure:

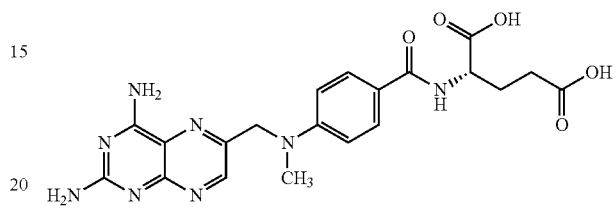

Methotrexate is also known by its IUPAC name, (2S)-2-[(4-{[(2,4-diaminopteridin-6-yl)methyl](methyl) amino}benzoyl)amino]pentanedioic acid; by "MTX" and by "amethopterin." Methotrexate sodium is available by prescription in the United States. Methotrexate's synthesis has been described in U.S. Pat. No. 4,080,325, which is hereby incorporated by reference in its entirety.

In still another embodiment, an agent of the invention is a modulator of macrophage polarization. Illustrative modulators of macrophage polarization include peroxisome proliferator activated receptor gamma (PPAR-g) modulators, including, for example, agonists, partial agonists, antagonists or combined PPAR-gamma/alpha agonists.

In some embodiments, the PPAR gamma modulator is a full agonist or a partial agonist. In some embodiments, the PPAR gamma modulator is a member of the drug class of thiazolidinediones (TZDs, or glitazones). By way of non-limiting example, the PPAR gamma modulator may be one or more of rosiglitazone (AVANDIA), pioglitazone (ACTOS), troglitazone (REZULIN), netoglitazone, rivoglitazone, ciglitazone, rhodanine. In some embodiments, the PPAR gamma modulator is one or more of irbesartan and telmesartan. In some embodiments, the PPAR gamma modulator is a nonsteroidal anti-inflammatory drugs (NSAID, such as, for example, ibuprofen) and indoles. Known inhibitors include the experimental agent GW-9662. Further examples of PPAR gamma modulators are described in WIPO Publication Nos. WO/1999/063983, WO/2001/000579, Nat Rev Immunol. 2011 Oct. 25; 11(11):750-61, or agents identified using the methods of WO/2002/068386, the contents of which are hereby incorporated by reference in their entireties.

In some embodiments, the PPAR gamma modulator is a "dual," or "balanced," or "pan" PPAR modulator. In some embodiments, the PPAR gamma modulator is a glitazar, which bind two or more PPAR isoforms, e.g., muraglitazar (Pargluva) and tesaglitazar (Galida) and aleglitazar.

In another embodiment, an agent of the invention is semapimod (CNI-1493) as described in Bianchi, et al. (March 1995). Molecular Medicine (Cambridge, Mass.) 1 (3): 254-266, the contents of which are hereby incorporated by reference in their entireties.

In still another embodiment, an agent of the invention is a migration inhibitory factor (MIF) inhibitor. Illustrative MIF inhibitors are described in WIPO Publication Nos. WO 2003/104203, WO 2007/070961, WO 2009/117706 and U.S. Pat. Nos. 7,732,146 and 7,632,505, and 7,294,753 7,294,753 the contents of which are hereby incorporated by reference in their entireties. In some embodiments, the MIF inhibitor is (S,R)-3-(4-hydroxyphenyl)-4,5-dihydro-5-isoxazole acetic acid methyl ester (ISO-1), isoxazoline, p425 (J. Biol. Chem., 287, 30653-30663), epoxyazadiradione, or vitamin E.

In still another embodiment, an agent of the invention is a chemokine receptor 2 (CCR2) inhibitor as described in, for example, U.S. Patent and Patent Publication Nos.: U.S. Pat. No. 7,799,824, U.S. Pat. No. 8,067,415, US 2007/0197590, US 2006/0069123, US 2006/0058289, and US 2007/0037794, the contents of which are hereby incorporated by reference in their entireties. In some embodiments, the CCR2) inhibitor is Maraviroc, cenicriviroc, CD192, CCX872, CCX140, 2-((Isopropylaminocarbonyl)amino)-N-(2-((cis-2-((4-(methylthio)benzoyl)amino)cyclohexyl) amino)-2-oxoethyl)-5-(trifluoromethyl)-benzamide, vicriviroc, SCH351125, TAK779, Teijin, RS-504393, compound 2, compound 14, or compound 19 (Plos ONE 7(3): e32864).

In various specific embodiments, an agent of the invention is one or more of CKR-2B, a 2-thioimidazole, CCR2 Antagonist (CAS 445479-97-0), and CCX140.

In yet another embodiment, an agent of the invention is a clodronate. In still another embodiment, the agent is a clodronate liposome preparation as described in Barrera et al. *Arthritis and Rheumatism*, 2000, 43, pp. 1951-1959, the contents of which are hereby incorporated by reference in their entireties.

In still another embodiment, an agent of the invention is a chelated or unchelated form of gadolinium, for example gadolinium chloride (GAD).

In various embodiments an agent of the invention is an anti-VEGF agent. Non limiting examples of anti-VEGF agents useful in the present methods include ranibizumab, bevacizumab, aflibercept, KH902 VEGF receptor-Fc, fusion protein, 2C3 antibody, ORA102, pegaptanib, bevasiranib, SIRNA-027, decursin, decursinol, picropodophyllin, guggulsterone, PLG101, eicosanoid LXA4, PTK787, pazopanib, axitinib, CDDO-Me, CDDO-Imm, shikonin, beta-, hydroxyisovalerylshikonin, ganglioside GM3, DC101 antibody, Mab25 antibody, Mab73 antibody, 4A5 antibody, 4E10 antibody, 5F12 antibody, VA01 antibody, BL2 antibody, VEGF-related protein, sFLT01, sFLT02, Peptide B3, TG100801, sorafenib, G6-31 antibody, a fusion antibody and an antibody that binds to an epitope of VEGF. Additional non-limiting examples of anti-VEGF agents useful in the present methods include a substance that specifically binds to one or more of a human vascular endothelial growth factor-A (VEGF-A), human vascular endothelial growth factor-B (VEGF-B), human vascular endothelial growth factor-C (VEGF-C), human vascular endothelial growth factor-D (VEGF-D) and human vascular endothelial growth, factor-E (VEGF-E), and an antibody that binds, to an epitope of VEGF.

In one embodiment, the anti-VEGF agent is the antibody ranibizumab or a pharmaceutically acceptable salt thereof. Ranibizumab is commercially available under the trademark LUCENTIS. In another embodiment, the anti-VEGF agent is the antibody bevacizumab or a pharmaceutically acceptable salt thereof. Bevacizumab is commercially available under the trademark AVASTIN. In another embodiment, the anti-VEGF agent is aflibercept or a pharmaceutically acceptable salt thereof. Aflibercept is commercially available under the trademark EYLEA. In one embodiment, the anti-VEGF agent is pegaptanib or a pharmaceutically acceptable salt thereof. Pegaptinib is commercially available under the trademark MACUGEN. In another embodiment, the anti-VEGF agent is an antibody or an antibody fragment that binds to an epitope of VEGF, such as an epitope of VEGF-A, VEGF-B, VEGF-C, VEGF-D, or VEGF-E. In some embodiments, the VEGF antagonist binds to an epitope of VEGF such that binding of VEGF and VEGFR are inhibited. In one embodiment, the epitope encompasses a component of the three dimensional structure of VEGF that is displayed, such that the epitope is exposed on the surface of the folded VEGF molecule. In one embodiment, the epitope is a linear amino acid sequence from VEGF.

In various embodiments, an agent of the invention is a renin angiotensin system (RAS) inhibitor. In some embodiments, the renin angiotensin system (RAS) inhibitor is one or more of an angiotensin-converting enzyme (ACE) inhibitor, an angiotensin-receptor blocker, and a renin inhibitor.

Non limiting examples of angiotensin-converting enzyme (ACE) inhibitors which are useful in the present invention include, but are not limited to: alacepril, alatriopril, altiopril calcium, ancovenin, benazepril, benazepril hydrochloride, benazeprilat, benzazepril, benzoylcaptopril, captopril, captoprilcysteine, captoprilglutathione, ceranapril, ceranopril, ceronapril, cilazapril, cilazaprilat, converstatin, delapril, delaprildiacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spirapril hydrochloride, temocapril, temocapril hydrochloride, teprotide, trandolapril, trandolaprilat, utibapril, zabicipril, zabiciprilat, zofenopril, zofenoprilat, pharmaceutically acceptable salts thereof, and mixtures thereof.

Non limiting examples of angiotensin-receptor blockers which are useful in the present invention include, but are not limited to: irbesartan (U.S. Pat. No. 5,270,317, hereby incorporated by reference in its entirety), candesartan (U.S. Pat. Nos. 5,196,444 and 5,705,517 hereby incorporated by reference in their entirety), valsartan (U.S. Pat. No. 5,399, 578, hereby incorporated by reference in its entirety), and losartan (U.S. Pat. No. 5,138,069, hereby incorporated by reference in its entirety).

Non limiting examples of renin inhibitors which are useful in the present invention include, but are not limited to: aliskiren, ditekiren, enalkiren, remikiren, terlakiren, ciprokiren and zankiren, pharmaceutically acceptable salts thereof, and mixtures thereof.

In various embodiments an agent of the invention is a steroid. In some embodiments, a steroid is a compound belonging to or related to the following illustrative families of compounds: corticosteroids, mineralicosteroids, and sex steroids (including, for example, potentially androgenic or estrogenic or anti-andogenic and anti-estrogenic molecules). Included amongst these are, by way of non-limiting example, prednisone, prednisolone, methyl-prednisolone, triamcinolone, fluocinolone, aldosterone, spironolactone, danazol (otherwise known as OPTINA), and others.

In various embodiments an agent of the invention is an agent that modulates autophagy, microautophagy, mitophagy or other forms of autophagy. In some embodiments, the candidate drug and/or compound is one or more of sirolimus, tacrolimis, rapamycin, everolimus, bafilomycin, chloroquine, hydroxychloroquine, spautin-1, metformin, perifosine, resveratrol, trichostatin, valproic acide, Z-VAD-FMK, or others known to those in the art. Without wishing to be bound by theory, agent that modulates autophagy, microautophagy, mitophagy or other forms of autophagy may alter the recycling of intra-cellular components, for example, but not limited to, cellular organelles, mitochondria, endoplasmic reticulum, lipid or others. Without further wishing to be bound by theory, this agent may or may not act through microtubule-associated protein 1A/1B-light chain 3 (LC3).

Fluorescent Compounds

In some embodiments, the fluorescent compound is suitable for imaging with various wavelengths of fluorescence. In some embodiments, these wavelengths range from visible light to infrared, e.g., 390 nm to 1 mm, including, for example, blue light, white light, and near-infrared. In some embodiments, the dye is a near-infrared dye. In some embodiments, the dye is ICG.

In some embodiments, the fluorescent compound is suitable for imaging with various wavelengths of fluorescence. In some embodiments, these wavelengths range from visible light to infrared, e.g., about 390 nm to about 1 mm, including, for example, blue light, white light, and near-infrared. In some embodiments, the absorption is from about 390 nm to about 1 mm. In some embodiments, the emission is from about 390 nm to about 1 mm.

In some embodiments, the fluorescent compound absorbs light at a wavelength of about 600 nm to about 900 nm and/or emits light at a wavelength of about 750 nm to about 950 nm.

In some embodiments, the dye is a near-infrared dye. In some embodiments, the dye is ICG. In some embodiments, the ICG excitation/emission filters are 795 nm (excitation)/810 nm (emission).

In some embodiments, the dose of the fluorescent compound, e.g. a dye (including ICG), is an effective amount of the fluorescent compound. In various embodiments, the dose of ICG is from about 0.1 to about 10 mg/kg of an animal. In some embodiments, the dose is about 0.1, or about 0.3, or about 0.5, or about 1.0, or about 2.0, or about 3.0, or about 4.0, or about 5.0, or about 6.0, or about 7.0, or about 8.0, or about 9.0, or about 10.0 mg/kg of an animal.

In various embodiments, the fluorescent compounds, or metabolites thereof, cause a fluorescence which occurs in RPE cells and/or immune cells.

In other embodiments, the methods described herein do not comprise administering (i) an additional amount of fluorescent compound to the animal or (ii) a second fluorescent compound to the animal.

Toxins

In some embodiments, a toxin known to affect ocular tissue, including but not limited to, the RPE or retina, is provided.

In some embodiments, the toxin is one or more of aluminium, aminophenoxyalkanes (a non-limiting example includes, but is not limited to, 1,4,-bis(4-aminophenoxy)-2-phenylbenzene to rats), cationic amphophilic drugs/tricyclic antidepressants (non-limiting examples include but are not limited to amiodarone, chloroamitriptyline, chlorphentermine, clomipramine, imipramine, iprindole, various aminoglycosides, and other cationic amphophilic compounds), desferrioxamine, dl-(p-trifluoromethylphenyl) isopropylamine hydrochloride, fluoride (e.g. sodium fluoride), iodate (non-limiting examples include but are not limited to, sodium or potassium iodate), iodoacetate, lead, methanol and formic acid, 4,4'-Methylenedianiline, N-methyl-N-nitrosurea, naphthalene, napthol, nitroaniline (N-3-pyridylmethyl-N'-p-nitrophenylurea/nitroanilin/pyriminil), organophosphates (non-limiting examples include but are not limited to ethylthiometon, fenthion, and fenitrothion), oxalate (a non-limiting example includes but are not limited to dibutyl oxalate), phenothiazines (non-limiting examples include but are not limited to piperidylchlorophenothiazine, thioridazine, and chlorpromazine), quinolines (a non-limiting example includes, but is not limited to, chloroquine and hydroxychloroquine), streptozotocin, taurine deficiency, urethane, zinc deficiency caused by metal chelators, and derivatives and variants thereof.

In some embodiments, the toxin is an iodate. In some embodiments, the toxin is sodium or potassium iodate.

In some embodiments, the toxin induces atrophy of ocular tissue. In various embodiments, the atrophy comprises necrosis and/or apoptosis. In various embodiments, the atrophy comprising necrosis and/or apoptosis is of RPE cells. In some embodiments, the toxin reduces or modifies autophagy. In some embodiments, the toxin induces geographic atrophy and/or the expansion of geographic atrophy. In some embodiments, the toxin induces one or more of the above-mentioned effects.

In some embodiments, the toxin is administered one time, or two times, or three times. In some embodiments, the toxin is administered one time, or two times, or three times, or four times, or five times. In some embodiments, a second, or third, or fourth, or fifth administration is within about a day, or 1 week, or 1 month of the first.

In some embodiments, the toxin administered may be may be one or more of the agents described herein. In various embodiments, the second, or third, or fourth, or fifth pulse is a modulator of autophagy, cell survival, cell death, proliferation, regeneration, and the like, as described herein and as known in the art.

In another embodiment, the methods described herein comprise administering (i) an additional amount of a first toxin to the animal and/or (ii) a second toxin to the animal. In some embodiments, the methods described herein comprise further comprise observing a reduction in the rate of formation, growth or expansion of patches of ocular tissue atrophy or patches of tissue loss.

In various embodiments, doses of the toxins are known to those in the art. For example, a suitable dosage may be in a range of about 0.1 mg/kg to about 100 mg/kg of body weight of the subject, for example, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg body weight, inclusive of all values and ranges therebetween.

In one embodiment, the toxin is $NaIO_3$ and the dose is about 50 mg/kg of body weight. In one embodiment, the toxin is $NaIO_3$ and the dose is about 45 mg/kg of body weight. In one embodiment, the toxin is $NaIO_3$ and the dose is about 30 mg/kg of body weight.

Pharmaceutically Acceptable Salts and Excipients

Any agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compounds of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, an agent of the invention is in the form or a pharmaceutically acceptable salt. In some embodiments, the pharmaceutically acceptable salt is a sodium salt. In some embodiments, particularly where $R_3$ of the compounds of Formula I is hydrogen, the compounds of Formula I are in the form of a pharmaceutically acceptable salt. In some embodiments, the compound of Formula I is a pharmaceutically acceptable salt of bindarit. In some embodiments, methotrexate is in the form or a pharmaceutically acceptable salt. In some embodiments, the pharmaceutically acceptable salt of methotrexate is methotrexate sodium.

Further, any agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

Formulations, Administration, and Dosing

Any agent described herein can take the form of solutions, suspensions, emulsion, intra-ocular injection, intra-vitreal injection, topical ophthalmic drops, sub-conjunctival injection, sub-Tenon's injection, trans-scleral formulations, tablets, pills, pellets, capsules, capsules containing liquids, powders, sustained-release formulations, suppositories, emulsions, aerosols, sprays, suspensions, or any other form suitable for use. In one embodiment, the composition is suitable for an intra-vitreal injection (see, e.g., ILUVIEN or similar forms) or implantation (see, e.g., RETISERT or similar forms). In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

In one embodiment, any agent described herein is formulated for ophthalmic administration, including, for example, intravitreal or intraocular administration, and/or intravenous administration. Typically, compositions for administration comprise sterile isotonic aqueous buffer. Where necessary, the compositions can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as lignocaine to lessen pain at the site of the injection.

In one embodiment, any agent described herein is formulated in accordance with routine procedures as a composition adapted for intra-ocular administration.

In one embodiment, any agent described herein is formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any agent described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

The ingredients may be supplied either separately or mixed together in unit dosage form, for example, as a pre-mixed solution, dry lyophilized-powder, or water-free concentrate in a hermetically sealed container such as an ampule, pre-filled syringe, or sachette indicating the quantity of active agent. Where any agent described herein is to be administered by intra-vitreal or intra-ocular delivery, it can be dispensed, for example, with a pre-filled syringe or injector, or in an ampule for withdrawal into a suitable syringe. Where any agent described herein is to be administered by infusion, it can be dispensed, for example, with an infusion bottle containing sterile pharmaceutical grade water or saline. Where any agent described herein is to be administered by injection, an ampule of sterile water for injection or saline can be provided so that the ingredients can be mixed prior to administration.

Any agent described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

Compositions can be prepared according to conventional mixing, granulating, coating or polymerization methods, respectively, and the present compositions can comprise, in one embodiment, from about 0.1% to about 99%; and in another embodiment from about 1% to about 70% of any agent described herein by weight or volume.

In another embodiment, any agent described herein acts synergistically when co-administered with another agent and is administered at doses that are lower than the doses commonly employed when such agents are used as monotherapy.

For example, the dosage any agent described herein as well as the dosing schedule can depend on various parameters, including, but not limited to, the blinding eye disease being treated, the subject's general health, and the administering physician's discretion. Any agent described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapeutic agent, to a subject in need thereof. In various embodiments any agent described herein is administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, an agent of the invention, including compounds of Formula I, methotrexate or their pharmaceutically acceptable salts, and one or more additional therapeutic agents are administered within 3 hours. In another embodiment, an agent of the invention, including compounds of Formula I, methotrexate or their pharmaceutically acceptable salts, and one or more additional therapeutic agents are administered at 1 minute to 24 hours apart.

The amount of any agent described herein that is admixed with the carrier materials to produce a single dosage can vary depending upon the subject being treated and the particular mode of administration. In vitro or in vivo assays can be employed to help identify optimal dosage ranges.

In general, the doses that are useful are known to those in the art. For example, doses may be determined with reference *Physicians' Desk Reference,* 66th Edition, PDR Network; 2012 Edition (Dec. 27, 2011), the contents of which are incorporated by reference in its entirety.

The dosage of any agent described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular blinding eye disease being treated, the severity of the disorder, and the anatomical location of the disorder. Some variations in the dosage can be expected.

In some embodiments, the administering is effected orally or intra-vascularly, or intraocularly, or periocularly, or to the ocular surface.

When ophthalmically administered to a human, for example, intravitreally, the dosage of an agent of the invention, including, for example, Formula I, methotrexate or a pharmaceutically acceptable salt thereof and/or additional therapeutic agent is normally 0.003 mg to 5.0 mg per eye per administration, or 0.03 mg to 3.0 mg per eye per administration, or 0.1 mg to 1.0 mg per eye per administration. In one embodiment, the dosage is 0.03 mg, 0.3 mg, 1.5 mg or 3.0 mg per eye. In another embodiment, the dosage is 0.5 mg per eye. The dosage can range from 0.01 mL to 0.2 mL administered per eye, or 0.03 mL to 0.15 mL administered per eye, or 0.05 mL to 0.10 mL administered per eye. In one embodiment, the administration is 400 µg of compound, monthly for at least three months.

Generally, when orally administered to a mammal, the dosage of any agent described herein may be 0.001 mg/kg/day to 100 mg/kg/day, 0.01 mg/kg/day to 50 mg/kg/day, or 0.1 mg/kg/day to 10 mg/kg/day. When orally administered to a human, the dosage of any agent described herein is normally 0.001 mg to 1000 mg per day, 1 mg to 600 mg per day, or 5 mg to 30 mg per day. In one embodiment, oral dosage is 600 mg per day. In one embodiment, the oral dosage is two 300 mg doses per day. In another embodiment, oral dosage is 7.5 mg per week to 15 mg per week.

For administration of any agent described herein by parenteral injection, the dosage is normally 0.1 mg to 250 mg per day, 1 mg to 20 mg per day, or 3 mg to 5 mg per day. Injections may be given up to four times daily. Generally, when orally or parenterally administered, the dosage of any agent described herein is normally 0.1 mg to 1500 mg per day, or 0.5 mg to 10 mg per day, or 0.5 mg to 5 mg per day. A dosage of up to 3000 mg per day can be administered.

In some embodiments, it may be desirable to administer one or more any agent described herein to the eye. Administration may be, by way of non-limiting example, intra-ocular, intra-vitreal, topical (including, but not limited to, drops and ointment), sub-conjunctival, sub-Tenon's, trans-scleral, suprachoroidal, subretinal, and via iontophoresis.

Other routes of administration may also be used, such as, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

The mode of administration can be left to the discretion of the practitioner, and depends in-part upon the site of the medical condition. In most instances, administration results in the release of any agent described herein into the bloodstream.

Any agent described herein can be administered orally. Such agents can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

Further methods of administration include but are not limited to intra-ocular, intra-vitreal, topical ocular (including but not limited to drops, ointments and inserts), sub-conjunctival, sub-Tenon's, suprachoroidal, trans-scleral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, more than one of any agent described herein is administered to the eye. Administration may be, by way of non-limiting example, intra-ocular, intra-vitreal, topical (including, but not limited to, drops and ointment), sub-conjunctival, sub-Tenon's, trans-scleral, and iontophoresis. The mode of administration can be left to the discretion of the practitioner, and depends in-part upon the site of the medical condition. In most instances, administration results in the release into the bloodstream.

In specific embodiments, it may be desirable to administer locally to the area in need of treatment.

In another embodiment, delivery can be in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989). In yet another embodiment, delivery can be in a controlled release system. In one embodiment, a slow release intra-ocular device may be used. In some embodiments, this device consists of a locally delivered erodible or non-erodable liquid, gel, polymer, etc.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In another embodiment, a controlled-release system can be placed in proximity of the target area to be treated, e.g., the retina, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any agent described herein can, independently, be one to four times daily or one to four times per month or one to six times per year or once every two, three, four or five years. Administration can be for the duration of one day or one month, two months, three months, six months, one year, two years, three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

The dosage regimen utilizing any agent described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any agent described herein can be administered in a single daily dose, or the total daily dosage can be administered in divided doses of two, three or four times daily. Furthermore, any agent described herein can be administered continuously rather than intermittently throughout the dosage regimen.

Methods of Treatment

In various aspects, the present invention provides for a method for treating or preventing dry AMD and/or RPD. In these aspects, the "agent of the invention" comprise compounds useful for both monotherapy and combination therapy (e.g. as an additional therapeutic agent). In general, monotherapy comprises the use of compounds of Formula I, methotrexate, or their pharmaceutically acceptable salts, while combination therapy comprises compounds of Formula I, methotrexate, or their pharmaceutically acceptable salts in combination with an additional therapeutic agent, including, one or more of an anti-VEGF agent, an ACE inhibitor, a PPAR-gamma agonist, a renin inhibitor, a steroid, an agent that modulates autophagy PPAR gamma modulator, semapimod, a MIF inhibitor, a CCR2 inhibitor, CKR-2B, a 2-thioimidazole, CAS 445479-97-0, CCX140, clodronate, a clodonate-liposome preparation or gadolinium chloride.

An evaluation of any of the treatments disclosed herein can comprise optical imaging, including, by way of non-limiting example, cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infrared, e.g., 390 nm to 1 mm, including, for example, blue light, white light, red-free, near infra-red, or infrared).

In some embodiments, the methods described herein comprise reducing the amount of pseudodrusen in the subject and/or reducing the amount of pseudodrusen in any one of the foveal area, perifoveal area, juxtafoveal area, and extrafoveal area of the subject's eye. In other embodiments, the methods described herein comprise reducing the rates of progression to late disease, wherein the late disease is any one of choroidal neovascularization or geographic atrophy. In some embodiments, the methods described herein comprise reducing the rates of expansion of geographic atrophy.

In some embodiments, the methods of treatment described herein comprise treatment, prevention, or reduction in the rate of pathogenesis of dry AMD and/or RPD.

Compound Evaluation Methods

In some aspects, the invention provides a method for identifying whether a candidate compound is useful for the treatment of a blinding eye disease, comprising (a) administering an effective amount of a test compound to an animal whose eye comprises (i) a fluorescent compound in an amount effective to indicate the presence of a blinding eye disease in the animal and (ii) a toxin in an amount effective to induce atrophy of ocular tissue; (b) exposing the eye to light having a wavelength and intensity effective to cause the fluorescent compound to fluoresce; (c) comparing the eye's fluorescence pattern to a fluorescence pattern of an animal's eye that comprises the fluorescent compound and the toxin but not the test compound; and (d) selecting the test compound as a candidate compound if the result of the comparison of step (c) indicates that the test compound is useful for the treatment of a blinding eye disease. In some embodiments, step (b) comprises exposing the eye to light having a wavelength and intensity effective to cause the fluorescent compound to fluoresce, whether performed coincidentally with administration of the fluorescent compound, or later administration of the fluorescent compound.

In other embodiments, the comparing occurs at least about 24 hours, or at least about 7 days, or at least about 30 days, or at least 60 days, or at least 90 days after administering the test compound. In other embodiments, the comparing occurs at least about 2 months, or about 3 months, or about 4 months, or about 5 months, or at a maximum about 6 months. In some embodiments, the comparing comprises observation of the eye of the same animal pre- and post-administering an effective amount of a test compound. In some embodiments, the comparing comprises observation of the eye of different animals under different conditions (e.g. with or without administering an effective amount of a test compound).

In still other embodiments, the methods further comprise the step of observing the eye prior to administering the test compound. In some embodiments, this observing establishes one or more pre-administration characteristics of the eye.

In some embodiments, the comparison and/or observation comprises evaluating optical imaging, including, by way of non-limiting example, cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infrared, e.g., 390 nm to 1 mm, including, for example, blue light, white light, red-free, near infra-red, or infrared), between two different conditions (e.g. with or without administering an effective amount of a test compound).

In some embodiments, a compound is useful for the treatment of a blinding eye disease if it provides treatment, prevention, or reduction in the rate of pathogenesis of a blinding eye disease.

In yet another embodiment, the methods described herein comprise administering the fluorescent compound prior to administering the test compound. In still another embodiment, the methods described herein do not comprise administering (i) an additional amount of fluorescent compound to the animal or (ii) a second fluorescent compound to the animal.

In other embodiments, the methods described herein comprise administering the toxin prior to administering the test compound and/or administering the toxin prior to administering the fluorescent compound.

In other embodiments, a plurality of candidate compounds is identified. In some embodiments, the methods described herein further comprise comparing the usefulness of the plurality of candidate compounds in the treatment of a blinding eye disease and selecting a lead compound based on the comparison. In some embodiments, a lead compound is a preferred compound among a plurality of candidate compounds.

In some embodiments, the comparison comprises evaluating optical imaging, including, by way of non-limiting example, cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infra-red, e.g., 390 nm to 1 mm, including, for example, blue light, white light, red-free, near infra-red, or infrared), between two different conditions (e.g. with a first candidate compound versus with a second candidate compound). More than two candidate compounds can be compared.

Diagnostic and Predictive Methods

In some aspects, the invention provides a method for identifying a subject who has a blinding eye disease and is more likely than not to respond to treatment with an agent comprising determining whether the subject's eye has, or previously had, an increase (including a transient increase) in permeability across the epithelial barrier between a choroid and a retina of the eye relative to an undiseased state; wherein the increase in permeability indicates that the subject is more likely than not to respond to treatment with the agent; and wherein the agent is selected from methotrexate or a pharmaceutically acceptable salt thereof, or and a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl.

In another aspect, the present invention provides a method for identifying a blinding eye disease subject who is more likely than not to respond to treatment with an agent comprising determining whether the subject's eye has an presence (e.g. an influx) of phagocytic immune cells across a RPE (and/or from the inner retina), relative to an undiseased state, wherein the presence of phagocytic immune cells indicates that the subject is more likely than not to respond to treatment with the agent; and wherein the agent is selected from methotrexate or a pharmaceutically acceptable salt thereof, or and a compound of Formula I (as described herein) or a pharmaceutically acceptable salt thereof, wherein each of $R_1$ and $R_2$ is independently H or a $C_1$-$C_6$ alkyl and $R_3$ is H or a $C_1$-$C_6$ alkyl.

In another aspect, the invention provides a method for determining whether a blinding eye disease in a subject is responsive to treatment with an agent that inhibits the function of a subject's immune cells, comprising detecting a presence, detecting an absence, or measuring an amount of immune cells in the subject's eye, wherein the subject's eye fluoresces in response to light having a wavelength of about 600 nm to about 900 nm, or about 400 nm to about 900 nm, or about 400 to about 1600 nm.

In some embodiments, the methods described herein further comprise administering to the subject an effective amount of a fluorescent compound, wherein the detecting or measuring occurs at least one day after the administration of the fluorescent compound. In some embodiments, the detecting or measuring occurs at least one day after administering to the subject an effective amount of a fluorescent compound.

In some embodiments, the methods described herein comprise DNIRA for determining whether a blinding eye disease in a subject is responsive to treatment with an agent that inhibits the function of a subject's immune cells.

In some embodiments, the methods described herein further comprise the step of detecting or measuring FAF in the eye of the subject. In some embodiments, the methods described herein further comprise the step of correlating an FAF pattern to the presence, absence, or amount of immune cells in the subject's eye. In some embodiments, the methods described herein comprise a correlating between FAF and DNIRA data. In some embodiments, the correlating is of the spatial patterns observed in FAF and the subject's eye fluorescence in response to light having a wavelength of about 600 nm to about 900 nm, or about 400 nm to about 900 nm, or about 400 to about 1600 nm.

In some embodiments, areas of hyperfluorescent FAF or abnormal patterns of FAF may spatially coincide with areas of abnormal DNIRA, which may be hypofluorescent or hyperfluorescent. As abnormal FAF or hyperfluroescent FAF coincides with areas of disease activity and can predict areas of atrophy, without wishing to be bound by theory, in embodiments in which DNIRA labels the RPE and spatially coincides with hyperfluorescent FAF or abnormal FAF, phagocytic RPE cells that ingest s dye (for example, ICG) have abnormal amounts of lipofuscin or lipofuscin-like material. Further, without wishing to be bound by theory, in embodiments in which DNIRA labels immune cells (e.g. phagocytic immune cells, or cells of the innate immune system), and coincides spatially with hyperfluorescent FAF or abnormal FAF, phagocytic immune cells that ingest a dye (for example, ICG) have abnormal amounts of lipofuscin of lipofuscin-like material and/or coincide with cells that have abnormal amounts of lipofuscin or lipofuscin-like material. In some embodiments, the co-localization of abnormal FAF with abnormal DNIRA can therefore identify cellular targets for therapy. Such co-localization, provides, in some embodiments, both in animal models of disease, and in patients, the ability to target the immune system to reduce, slow, prevent disease progression.

In some embodiments, the detecting or measuring occurs at about one day, or about seven days, or at about thirty days after administration of the fluorescent compound. In other embodiments, the comparing occurs at least about 2 months, or about 3 months, or about 4 months, or about 5 months, or at a maximum about 6 months. In some embodiments, the comparing comprises observation of the eye of the same animal pre- and post-administering an effective amount of a test compound. In some embodiments, the comparing comprises observation of the eye of different animals under different conditions (e.g. with or without administering an effective amount of a test compound).

In some embodiments, the comparison comprises evaluating optical imaging, including, by way of non-limiting example, cSLO, FAF, OCT (including with cross-sectional, three-dimensional and en face viewing), SD-OCT (with cross-sectional, three-dimensional and en face viewing), or other imaging modalities including other wavelengths of fluorescence (e.g. wavelengths ranging from blue to infrared, e.g., 390 nm to 1 mm, including, for example, blue light, white light, red-free, near infra-red, or infrared), between two different conditions (e.g. with or without administering an effective amount of a test compound).

In some embodiments, the methods described herein do not further comprise administering (a) an additional amount of the fluorescent compound or (b) a second fluorescent compound.

Subjects and/or Animals

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell, such as, for example, an RPE cell and/or an immune cell. In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

In various embodiments, a subject's and/or an animal's eye comprises (i) a fluorescent compound in an amount effective to indicate the presence of a blinding eye disease in the subject and/or animal and (ii) a toxin in an amount effective to induce atrophy of ocular tissue. In some embodiments, such a subject and/or animal is administered an agent of the invention or is not administered an agent of the invention.

In various embodiments, RPE and immune cells are evaluated and/or effected. In some embodiments, immune cells include cells of a subject's and/or animal's innate immune system. In some embodiments, such cells include, but are not limited to, macrophage, monocyte, and microglial cells. In various embodiments, the invention provides for detecting a presence, detecting an absence, or measuring an amount of immune cells in a subject's and/or animal's eye.

Kits

The invention provides kits that can simplify the administration of any agent described herein. An exemplary kit of the invention comprises any agent described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the ocular surface. The kit can also further comprise one or more additional agent described herein.

In one embodiment, the kit comprises a container containing an effective amount of an agent of the invention, including, for example, compound of Formula I, methotrexate or a pharmaceutically acceptable salt thereof and an effective amount of another therapeutic agent, such those described herein.

This invention is further illustrated by the following non-limiting examples.

EXAMPLES

Example 1: Systemic Injection of the RPE Toxin, NaIO$_3$, Induces Complex Patterns of FAF Similar to Those of AMD and/or RPD The RPE toxin, sodium iodate (NaIO$_3$) generated patchy loss of the RPE and hypofluorescent DNIRA, in the rat eye similar to geographic atrophy (GA). This model not only developed RPE atrophy, it faithfully reproduced complex patterns of FAF associated with aggressive clinical disease, most closely resembling advanced dry AMD, RPD, and the diffuse trickling forms of dry AMD.

Materials: ICG (Cardiogreen), sodium iodate, Harris haematoxylin and eosin, were from Sigma-Aldrich (Oakville, ON, Canada). Tropicamide, 0.8%, in 5% phenylephrine hydrochloride solution (Diophenyl-T) was from Sandoz Canada Inc (Boucherville, QC, Canada), and GenTeal lubricating eye drops were from Novartis Pharmaceuticals Canada Inc (Dorval, QC, Canada). Paraformaldehyde, 32% in phosphate buffered saline (PBS), was from Electron Microscopy Sciences (Hatfield, Pa.). Mouse anti-rat CD68 antibody was from AbD Serotec (Oxford, UK), and mouse IgG was from Santa Cruz Biotechnology (Santa Cruz, Calif., USA). Rabbit anti-Iba-1 was from Wako Pure Chemical Industries Ltd (Osaka, Japan). Alexa-labeled fluorescent goat anti-mouse secondary antibody, Isolectin IB$_4$ Conjugates and TO-PRO-3 nucleic acid stain were from Invitrogen (Camarillo, Calif., USA). Dako fluorescent mounting medium was from Dako North America (Burlington, ON, Canada).

Animal procedures: all procedures were performed in accordance with the Canadian Council on Animal Care and with adherence to the *ARVO Statement for the Use of Animals in Ophthalmic and Vision Research*. For all experiments, Sprague Dawley (SD) rats aged 6-10 weeks were kept at a 12 hour dark/light cycle, with food and water ad libitum. For evaluation, rats were anesthetized with ketamine (100 mg/kg) and xylazine (10 mg/kg), and pupils dilated with Diophenyl-T. Eyes were conditioned using GenTeal lubricating eye drops. Animals were humanely sacrificed by intracardiac injection of T61 (Intervet Canada, Whitby, Canada), either after a single imaging session or after serial imaging.

Sodium iodate (45% solution), was prepared fresh for each set of experiments in 0.9% sodium chloride and injected to a final concentration of 45 mg/kg body weight. A total of 192 eyes were evaluated.

Fundus imaging was performed using a commercially available confocal scanning laser ophthalmoscope, (cSLO, Spectralis, Heidelberg Retinal Angiography, HRA-II; Heidelberg Engineering GmbH, Germany), and the Eye Explorer Image Capture system, version 1.1.10. Images were captured at a wavelength of 488 nm excitation with 500 nm barrier filter for fluorescein angiography without the barrier filter for red free (RF, green dominant) imaging, at 795/810 nm excitation/emission for ICG angiography, and with a 830 nm laser for infrared reflectance imaging.

To evaluate 488 nm FAF, cSLO imaging was performed in the absence of fluorescein dye. Fluorescein was not given at baseline or at any time during each study. In cases when it was necessary to simultaneously image the vasculature and provide landmarks for FAF image analysis, ICG was injected via tail vein, at 2 or 5 mg/kg, into a previously inserted 23 gauge tail vein catheter. In a small number of clearly indicated situations, such as initial characterization of the model, fluorescein dextran (200 kD) was provided intra-venously. Results from these latter studies using fluorescein angiography were performed in a subset of animals and not included in FAF analysis.

Fundus images were routinely obtained at baseline (day 0, i.e. prior to systemic NaIO$_3$ injection), and at days 3 or 4 (3/4), days 7 or 8 (7/8) and days 13 or 14 (13/14) after NaIO$_3$. In addition, for initial characterization of the model, images were acquired at 24 hours post-NaIO$_3$, at 21 to 28 days and out to 88 days (3 months). Where possible, composite images consisting of at least nine images were taken in the following order: optic nerve head, upper right, right, lower right, inferior, lower left, left, upper left, and the superior fields. In some cases, a second or third complete or partial ring of images was obtained more peripherally, typically by realigning the animal relative to the cSLO as needed. By contrast, in other cases, in which the full nine images could not be captured, and a partial composite image was generated.

High resolution spectral domain OCT images were obtained (Envisu R2200 VHR Animal SDOIS System, Bioptogen, USA). A scans were acquired at a rate of 36,000 per second, with a lateral resolution of approximately 2.8 µm at the level of the retina.

Tissue Analysis: hemotoxylin and eosin (H & E) histology of paraffin-embedded tissue was performed as known in the art after fixation with Davidson's fixative. Paraffin-embedded sections were viewed with a Nikon Upright E800 Microscope. Deparaffinization and rehydration procedure was followed as in H&E tissue processing.

For immunohistochemistry, sections were blocked in 5% BSA in TBS at room temperature and incubated overnight with anti-CD68 antibody at 4° C. with gentle shaking. After rinsing, samples incubated with secondary antibody for 2 hours at room temperature, and washed again. For negative control, same-species IgG was used at equivalent maximum molar concentrations as the primary antibody. Nuclei were counter-stained with TO-PRO-3.

Confocal and Fluorescent Microscopy: images were acquired using a TCS SL Confocal fluorescent microscope (Leica Microsystems, GmbH, Wetzlar, Germany), and images captured and analyzed using Leica Confocal Software. Upright epifluorescent microscope (Olympus BX50) was also used to view the autofluoresent signals of the cells under 488 nm wave length light. 3D reconstructions of confocal serial z-sections were performed using Imaris software version 7.4.2 (Bitplane).

FAF and angiographic imaging in vivo of the normal Sprague Dawley rat eye produced a faint, homogenous ground glass glow interrupted by radially-arranged retinal blood vessels that block RPE fluorescence and so appear dark, and by a central hypofluorescent circle at the optic nerve head (ONH), where RPE is absent (FIGS. 1A-D). Three days after systemic $NaIO_3$ injection, a single area of iso- or slightly hyperfluorescent FAF with hyperfluorescent borders appeared, and took the shape of a discrete island, sector, or 360° ring (FIGS. 1A-D). Islands or sectors are consistently located inferior to the ONH or in the inferior hemiretina (FIGS. 1A-D). When a 360° ring is present, it typically encompasses much of the fundus, with one border adjacent to, surrounding, the ONH and the other in the mid- to far-retinal periphery. Large 360° rings were the most commonly observed shape, occurring in 102/110 (93%) of eyes treated with sodium iodate (FIGS. 2A-D). In all cases, the islands, sectors or rings approached the ONH but were not contiguous with it (FIGS. 1A-D-3A-C). These and the following observations were confirmed in over 160 eyes.

Beginning approximately 4-5 days after $NaIO_3$ injection, a marked reticular or curvilinear pattern of alternating hyper/hypo-fluorescent FAF appeared within the islands, sectors or rings (FIGS. 1A-D). By day 7, this pattern was pronounced. In small lesions, it completely filled the island or sector and emerged rapidly. In large 360° rings, it was at first pronounced at the proximal and distal borders and continued to emerge over the next weeks, whereby its curvilinear components contributed to partial loops, ovals, circles, rosettes, and scalloped or "paw-print" patterns of FAF (FIGS. 2A-D). In some regions, curvilinear, round or oval shapes coalesce and appeared darker than the surrounding areas, appearing as homogenously dark grey patches of hypofluorescent FAF. With time, the hyperfluorescent reticular pattern matured in situ, becoming more granular and less smoothly curvilinear (FIGS. 2A-D). However, even as late as 20 weeks, the last time-point analyzed, the borders retained their hyperfluorescent reticular pattern and continued to creep slightly toward the retinal periphery.

Fluorescein angiography performed in a subset of animals confirmed that the reticular pattern does not correspond with the retinal or choroidal vasculature (note that fluorescein-dextran, a 488 nm dye, was not given to animals that underwent FAF imaging, unless indicated) (FIGS. 1A-D). However, ICG angiography revealed a permeability change that occurred at the chorio-retinal interface, across the RPE and BM, approximately two to three days after $NaIO_3$ that coincides with, both spatially and temporally, the emergence of the islands, sectors of rings of FAF (FIGS. 1A-D). This increase in permeability was transient and resolved by Day 7, the next timepoint routinely evaluated. The retinal vessels did not leak. In the $NaIO_3$ model, H&E staining confirms that fluid accumulates in the subretinal space. This was also observed by ultra-high resolution OCT in vivo.

Figure 3A:
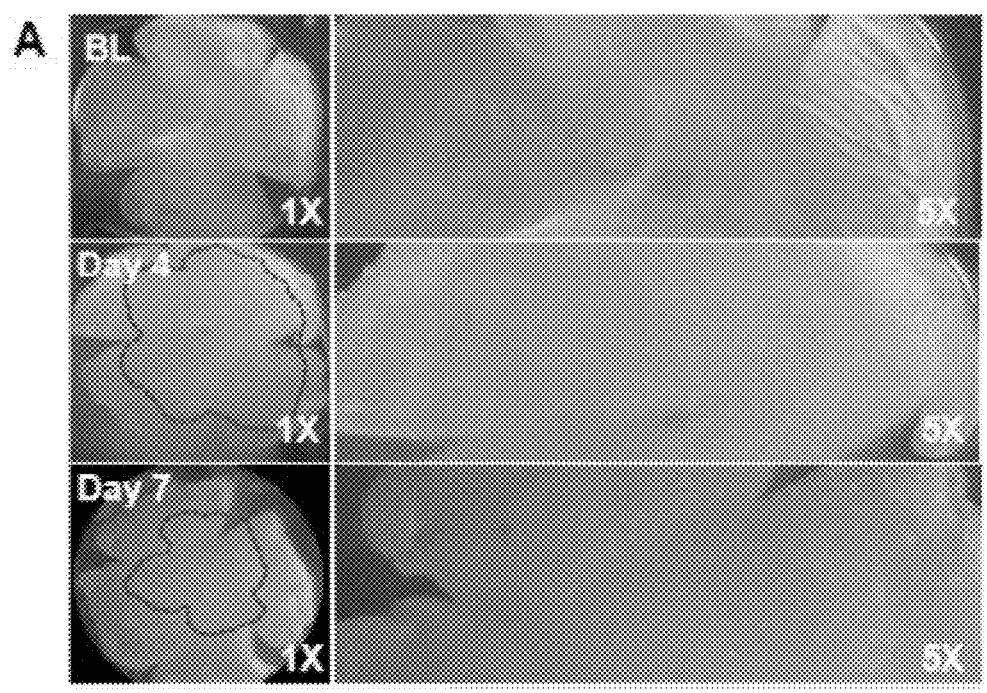
FIGS. 3A-C show that a curvilinear, reticular pattern of outer retinal deformation develops in the weeks after NaIO$_3$ injection.
Figure 3B:
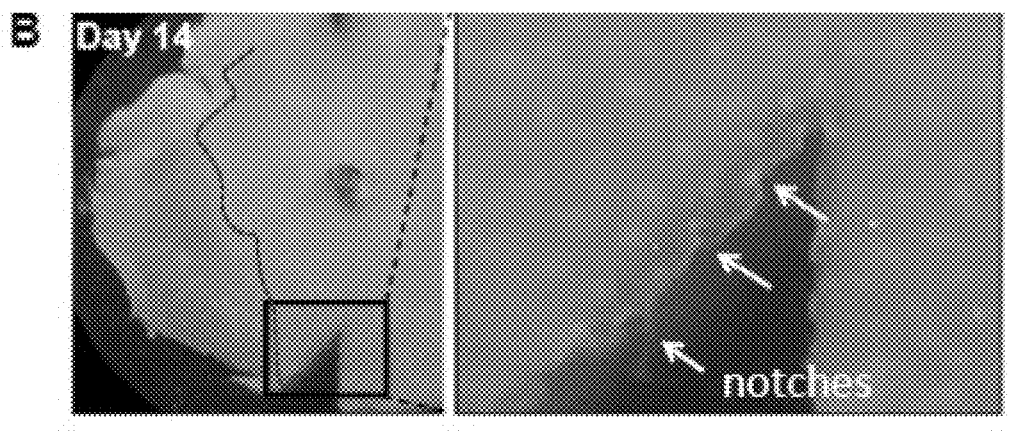
Figure 3C:
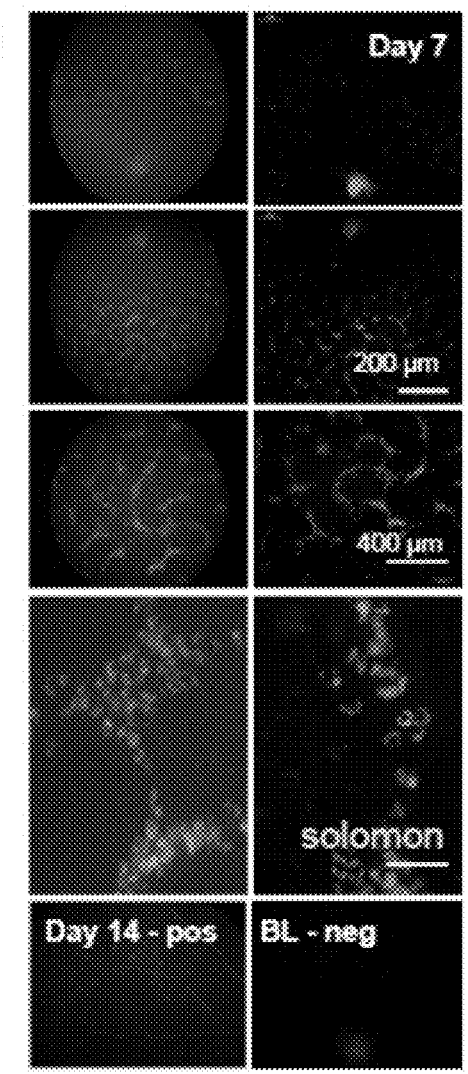

To determine the pathological correlate of the FAF pattern observed in vivo, excised retinal wholemounts were viewed at low magnification under white light and by epifluorescent microscopy at 488 nm—the same wavelength used for in vivo imaging, with no fluorescent IHC labeling. Depending on subsequent tissue analysis, two microscopes were used for this purpose: an epifluorescent device with a narrow excitation/emission window (488/520 nm), and the Inverted Leica DM IRE2 viewing system of a confocal microscope with a mercury arc lamp and long-pass (rather than band-pass) filter providing fluorescence from greater than 515 nm following excitation with a 450-490 nm band. Under white light, the normal rat retina appears fairly homogenous throughout, with some artifactuous deformation (FIG. 3A). By contrast, a subtle off-white, fine reticular pattern becomes apparent in samples obtained 7 days after $NaIO_3$ injection. By day 14, this pattern is more apparent and seen to correspond with small, outer retinal folds best illustrated at the cut edge of the retina (FIG. 3B). Viewed under 488 nm fluorescent light, this same curvilinear pattern is apparent. Though apparent by day 7 after injection, increasing autofluorescence makes this pattern more visible by Day 14 (FIG. 3C). Using higher magnification epifluorescent microscopy, it was demonstrated that this lacy, curvilinear pattern coincides with the spatial distribution of autofluorescent cells that appear to align with grooves or folds of the outer retina (FIGS. 3A-C).

Figure 4A:
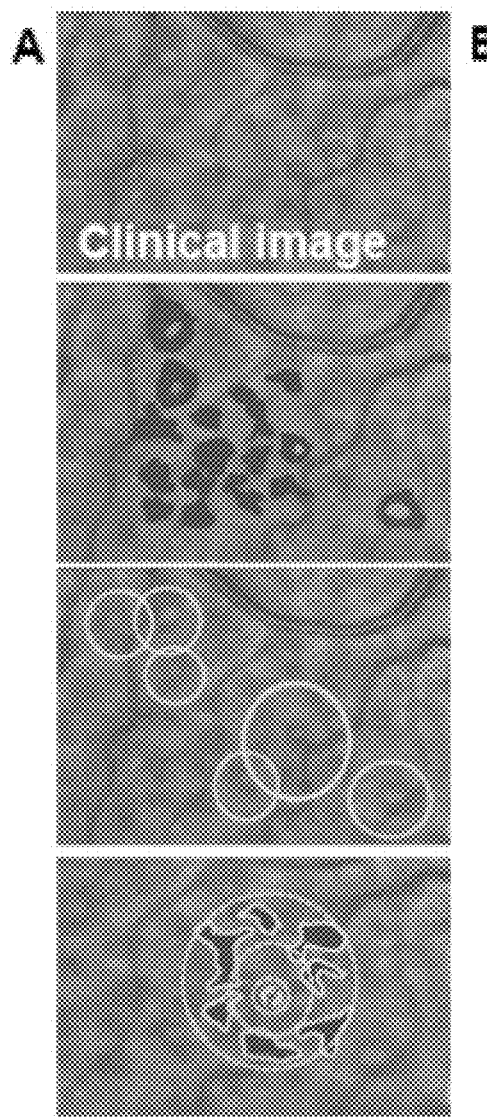
FIGS. 4A-C show interpretative illustrations which show how histologically-determined tissue findings can account for in vivo imaging following NaIO$_3$-induced RPE loss.
Figure 4B:
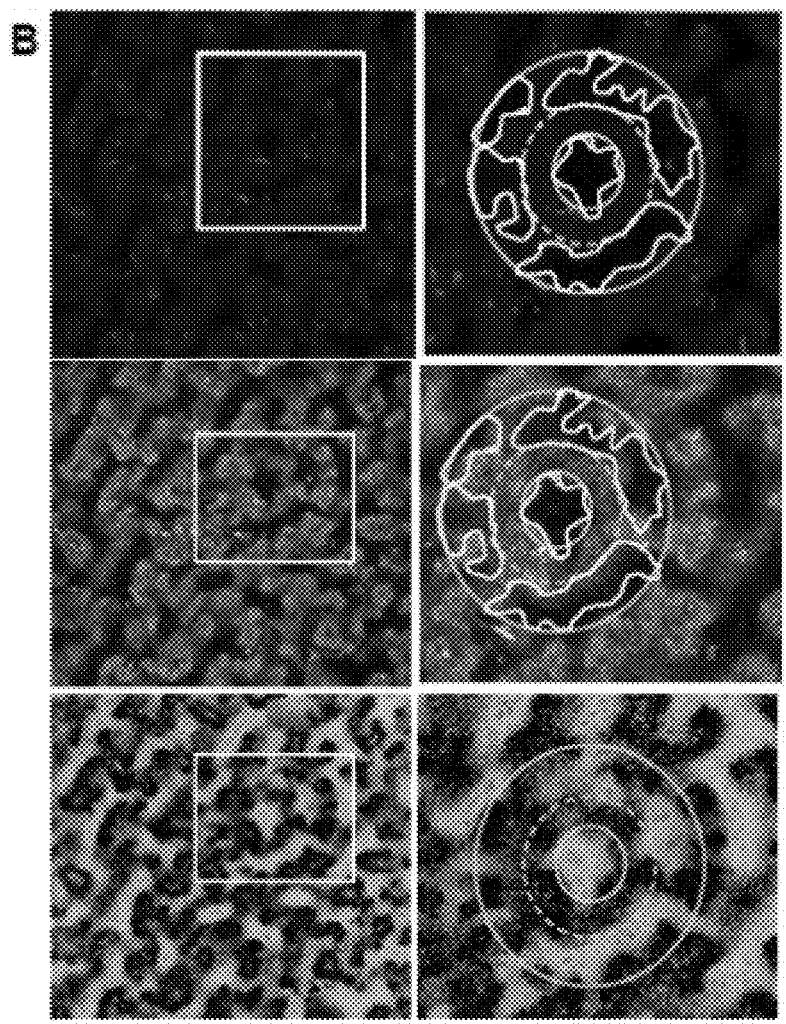
Figure 4C:
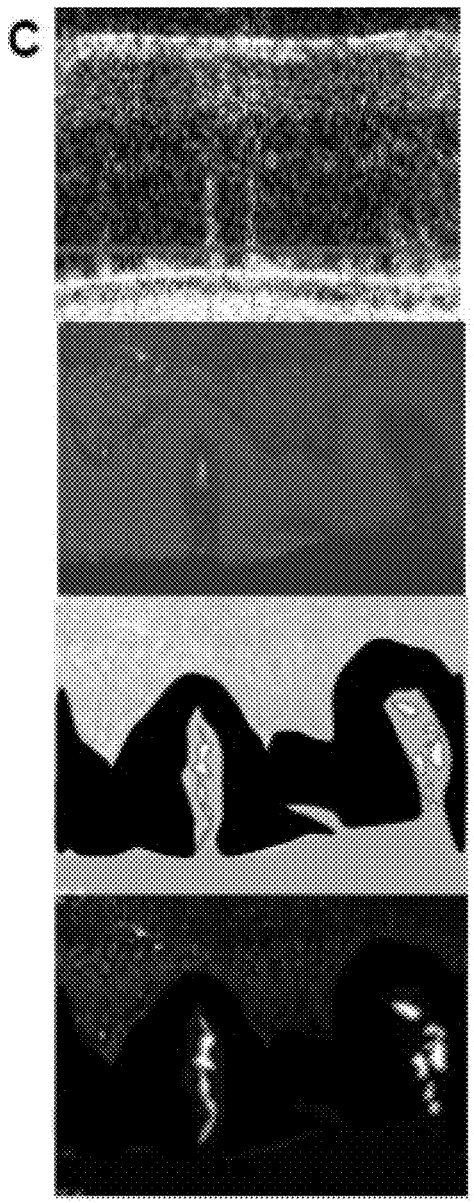

FIGS. 4A-C shows a comparison of the clinical features of RPD with tissue findings in the $NaIO_3$ model. In addition to clinical OCT imaging of the patient with RPD (that shows a base-down pyramidal structure in the subretinal space), color and red-free fundus images were obtained (FIGS. 4A-C). Red free images showed small dark spots that constitute individual pseudodrusen of RPD (FIG. 4A, top image). These are identified using dark grey overlay. We further highlight, circumscribed by circles, the presence of so-called "target lesions" that characterize RPD. These appear as dark spots with lighter centers. In parallel, a schematized illustration of folded outer rat retina, both en face and in cross-section that, when falsely colored and presented as black and white images—both "positive" and "negative"—appears to correlate directly with target-like lesions, and halos of RPD. Taken together, these data suggest that the 2D patterns of dark pseudodrusen within a lacy or reticular pattern of circles, halos and target lesion with dark centers viewed en face, in 2D, correspond with elevated rings and craters, considered volumetrically, in 3D. The inter-pseudodrusen matrix consists of ribbons of persistent subretinal inflammation that when cross-sectioned appear as pyramids or spikes by OCT. The lost outer retina between these structures appears dark. This places the OCT-defined pseudodrusen adjacent to the dark patches of RPD. Without wishing to be bound by theory, this correlation with structural deformity of the retina further explains why RPD can be visualized in several imaging modalities and are not limited to a particular wavelength, such as 488 nm, alone as would occur if the signal were fluorophore dependent.

Example 2: DNIRA of a Rat Eye After Systemic ICG Administration Identifies the Retinal Pigment Epithelial (RPE) Layer In Vivo It is demonstrated that a near infra-red dye, ICG, can label the RPE/outer retina following systemic injection and so enhance the detection of RPE and RPE atrophy. The observed change in DNIRA using the ICG excitation/emission filters is useful in lieu of FAF in models of disease to identify areas of RPE/outer retinal loss.

ICG dye, or PBS, was injected systemically in 46 Sprague Dawley rats at doses of 0.35 and 5.0 mg/kg, and the fundus was evaluated in vivo using confocal scanning laser ophthalmoscopy (cSLO), with 795/810 nm excitation/emission filters in place, prior to injection, and at days 2, 7, and 21 thereafter. Electroretinography (ERG) was performed to evaluate potential toxicity. In a subset of animals, an RPE toxin was injected to induce RPE damage or loss.

Specifically, for animal studies, animals were handled in accordance with the Association for Research in Vision & Ophthalmology (ARVO) guidelines for the humane use of animals in ophthalmic research, and according to the St. Michael's Hospital Animal Care Committee guidelines. 46 Sprague Dawley (SD) rats aged 6-10 weeks, weighing 200-300 g were kept on a 12 hour dark/light cycle, with food and water ad libitum. Animals were anesthetized with a combination of ketamine (100 mg/kg) and xylazine (10 mg/kg), and pupils dilated with a single drop of 0.8% tropicamide in 5% phenylephrine hydrochloride solution (Diophenyl-T, Sandoz Canada Inc). GenTeal lubricating eye drops (Novartis, Canada), were repeatedly applied to the corneal surface during all procedures.

CSLO: in vivo images were acquired using a commercially available cSLO (Heidelberg Retinal Angiography, HRA-2, Heidelberg Engineering, Germany). Images were obtained in the red-free, FAF (488/500 nm excitation/emission), NIR channel (830 nm) and ICG channel (795/810 nm excitation/emission).

ICG and Fluorescein Angiography: ICG dye (Cardiogreen, Sigma, Cat #12633) was freshly prepared prior to experimentation to a final stock concentration of 5.0 mg/ml. A 23-gauge catheter was inserted into the tail vein, and ICG dye infused at doses of 0.35, or 5.0 mg/kg. Images were taken prior to injection (baseline), during dye circulation, and at various intervals thereafter out to 20 minutes. In a subset of animals, fluorescein-dextran (200 kD) (Sigma, Cat # FD2000S) solution, at 5.0 mg/ml, was injected IV via tail vein catheter to yield a final dose of 5.0 mg/kg. ICG and fluorescein angiography was performed simultaneously in a subset of animals only, otherwise fluorescein was not injected. Angiographic images were obtained in the fluorescein and ICG channels with excitation and emission filters of 488/500 nm and 795/810 nm respectively. Control animals received PBS.

DNIRA: DNIRA images were obtained in the days and weeks after ICG injection using the ICG angiography settings, i.e. with excitation/emission filters, but without re-injection of dye at 24 hours, 48 hours, 3 days, 7 days, 21 days and 28 days after angiography. Angiography was not performed again during the time-course of the study.

Toxin administration: in a subset of animals (n=7), the RPE toxin NaIO$_3$ (Sigma, cat #424064) was injected systemically via a 23G catheter inserted into the tail vein at a dosage of 45 mg/kg body weight. In these animals, ICG angiography at 0.35 mg/kg was performed immediately prior to NaIO$_3$ injection. DNIRA was performed 7 days after ICG and NaIO$_3$ injection Electroretinography (ERG):animals receiving ICG or PBS were evaluated using the Espion (DiagnosysLLC, USA) mini-Ganzfeld ERG system. Following anesthesia, animals were placed on an electrically silent heating pad and gold coil electrodes placed on the corneal surface after application of GenTeal lubricating drops. Following a short train of dim flashes (0.01 candela s/m$^2$, 1.0 Hz), a scotopic b-wave amplitude was evaluated using a single bright flash (3 candela s/m$^2$) that we previously determined consistently produces a response close to the maximum b-wave amplitude. Student t-test was used to compare post-injection amplitudes against baseline (prior to injection).

Statistical analysis used the ANCOVA analysis of regression.

Figure 5A:
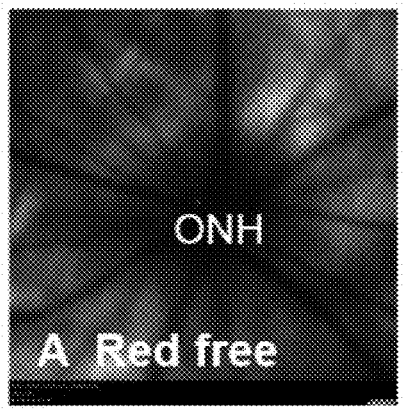
FIGS. 5A-H show that speckled NIR fluorescence is detected by 795/810 nm cSLO imaging, but cannot be detected without previous ICG injection, i.e., this fluorescence can only be detected with the excitation/emission filters in place, but is not coincident with or in the transit period following dye injection (that is, using the DNIRA method).
Figure 5B:
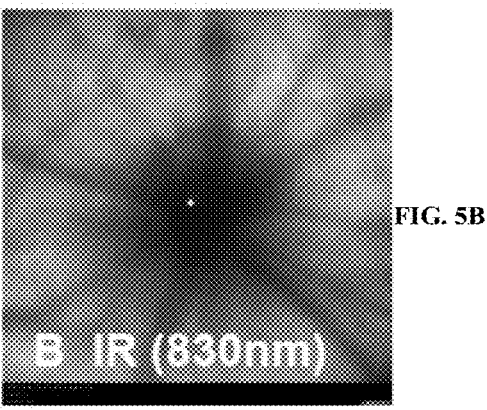
Figure 5C:
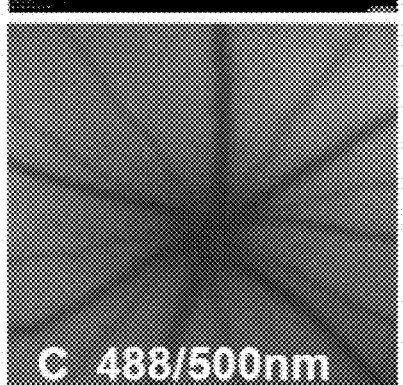

Representative baseline (pre-ICG) cSLO findings in the normal Sprague Dawley rat eye are shown (FIGS. 5A-H), and served along with PBS-treated animals (FIG. 6A), as normal controls for all experimentation. Red-free (i.e., green dominant) imaging identified the optic nerve head (ONH) and radial blood vessel of the retina (FIG. 5A). Low levels of endogenous signal were also seen at longer wavelengths, in the NIR channel (830 nm), and provided a similar image of the ONH and vasculature with some potential imaging of the deeper choroidal vessels that arises due to deeper light penetration (FIG. 5B). Consistent with human studies, FAF appeared as a faint ground-glass glow that is lacking in detail, and is obscured by the radial retinal blood vessels and is absent at the ONH (FIG. 5C). This diffuse glow however is very faint.

Figure 5D:
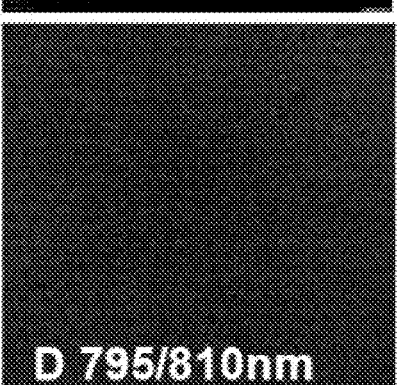
Figure 5E:
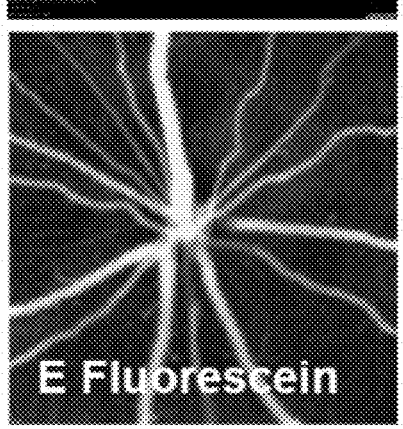
Figure 5F:
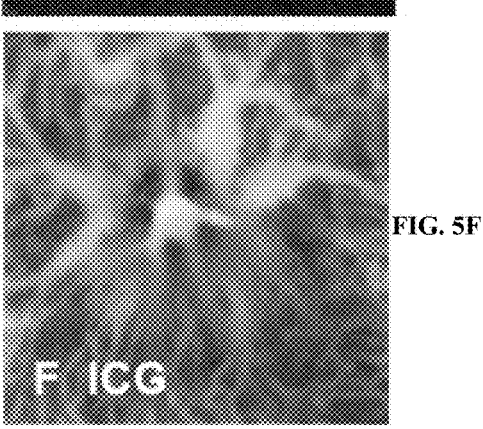

By contrast, with the NIR excitation/emission filters in place as for ICG angiography, no or negligible signal was observed in the eye prior to ICG injection (FIG. 5D). Scan lines were evident and the vasculature was barely detectable or not detectable. This was observed in over 60 eyes. Immediately following ICG injection, both the retinal and choroidal vessels (FIG. 5F, and FIG. 5G second panel) were identified during the transit phase and out to the experimental endpoint, 20 minutes later. Fluorescein angiography also confirmed the normal retinal vasculature (FIG. 5E). In wild-type SD animals, no leakage was seen from either vascular bed using either fluorophore.

Figure 5G:
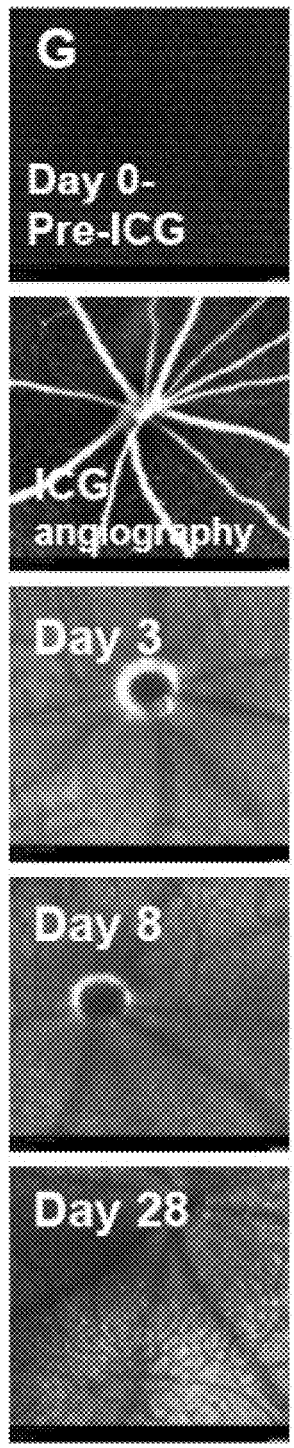
Figure 5H:
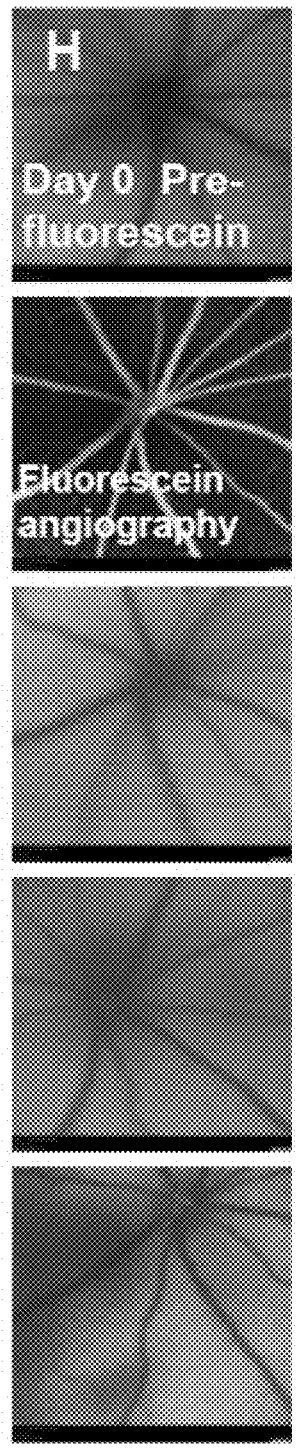

Though baseline images prior to ICG angiography exhibited no signal under NIR stimulation in the presence of the ICG excitation/emission filters, images obtained at 3, 8, 21 and 28 days after a single injection of ICG at day 0 (t=0), demonstrated a delayed and persistent fluorescence (FIG. 5G). This was not observed in similar experiments performed following angiography with fluorescein-dextran dye and analyzed with the fluorescein angiography filters in place (FIG. 5H), where the same level of low pre-injection fluorescence is visible throughout the time course of investigation. It also did not occur in the absence of previous ICG injection (FIG. 6A). Qualitative analysis of this delayed NIR fluorescence after ICG showed a "mosaic" pattern of small speckles in the posterior pole that, viewed en face, are deep (external) to the retinal vessels and obscure the view to the choroidal vasculature, suggesting its location between the retina and the choroid. The ONH and circumpapillary area did not fluoresce. These features are similar to those of FAF performed in the blue spectrum in patients. It was determined that the same plane of focus is optimal for both fluorescent techniques.

The observations made using DNIRA after ICG injection were dose-dependent (FIGS. 6A-D). The higher the initial ICG dosage used for angiography, the brighter the NIR signal. The high dose, 5 mg/kg, required that the gain (sensitivity) of the cSLO be reduced to obtain suitable quality images, while the low dose (0.35 mg/kg) was less bright, and required that the gain be increased to obtain suitable quality images. Comparative images (FIG. 6A, FIG. 6B and FIG. 6C), taken with the gain set at the same level, demonstrated a dose-responsive increase in brightness. In the same experiment, it was also determined that by day 28 the speckled pattern faded in animals receiving low-dose ICG (FIG. 6B). By contrast, in animals receiving high dose ICG, there was little appreciable difference between days 3 and 28 post-injection (FIG. 6C).

NIR reflectance imaging at 830 nm, without 795/810 nm excitation/emission filters necessary for ICG activation, did not yield the speckled, dose-dependent and time-dependent fluorescence findings observed with DNIRA.

Figure 7A:
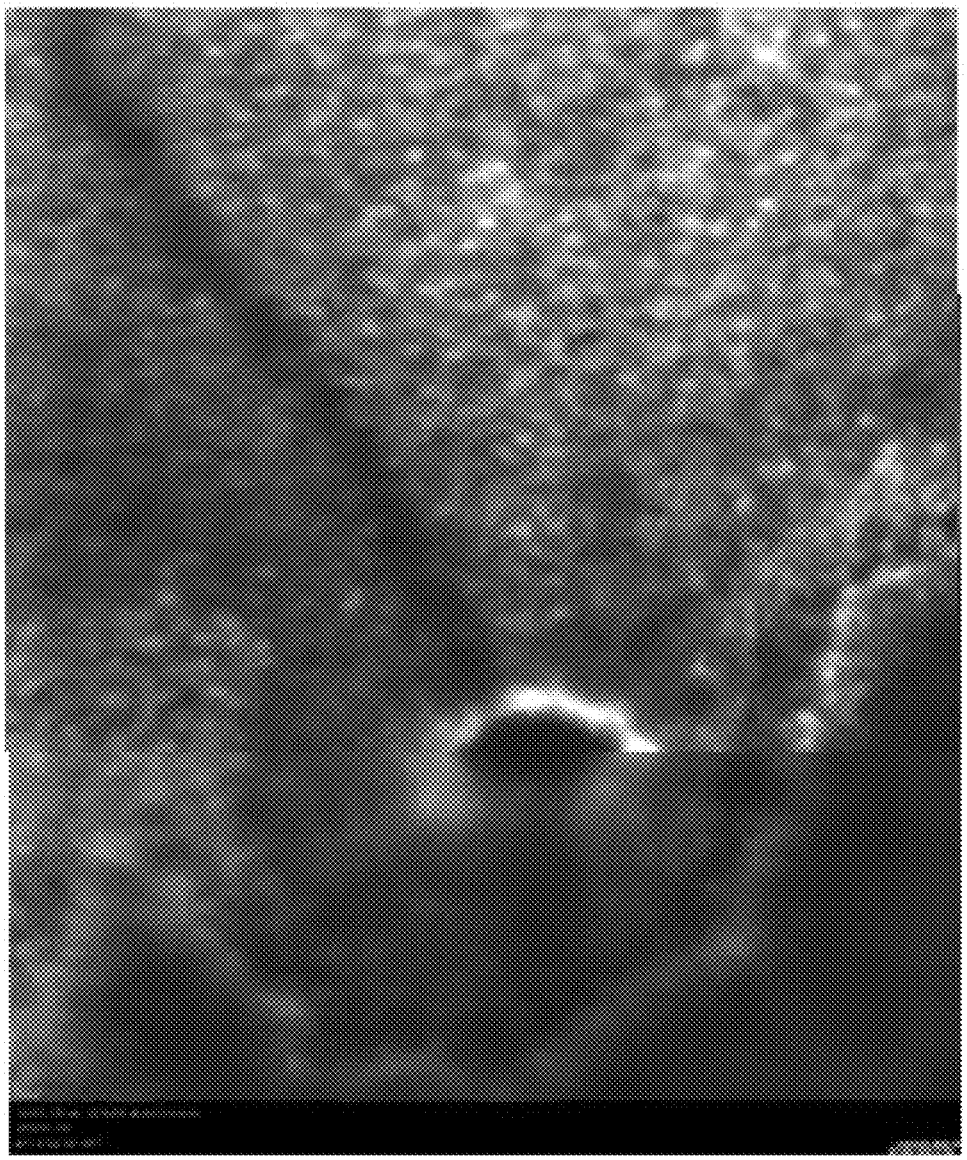
FIGS. 7A-B shows that sodium iodate causes patchy loss of delayed NIR fluorescence through which develops a clear view to the choroidal vasculature
Figure 7B:
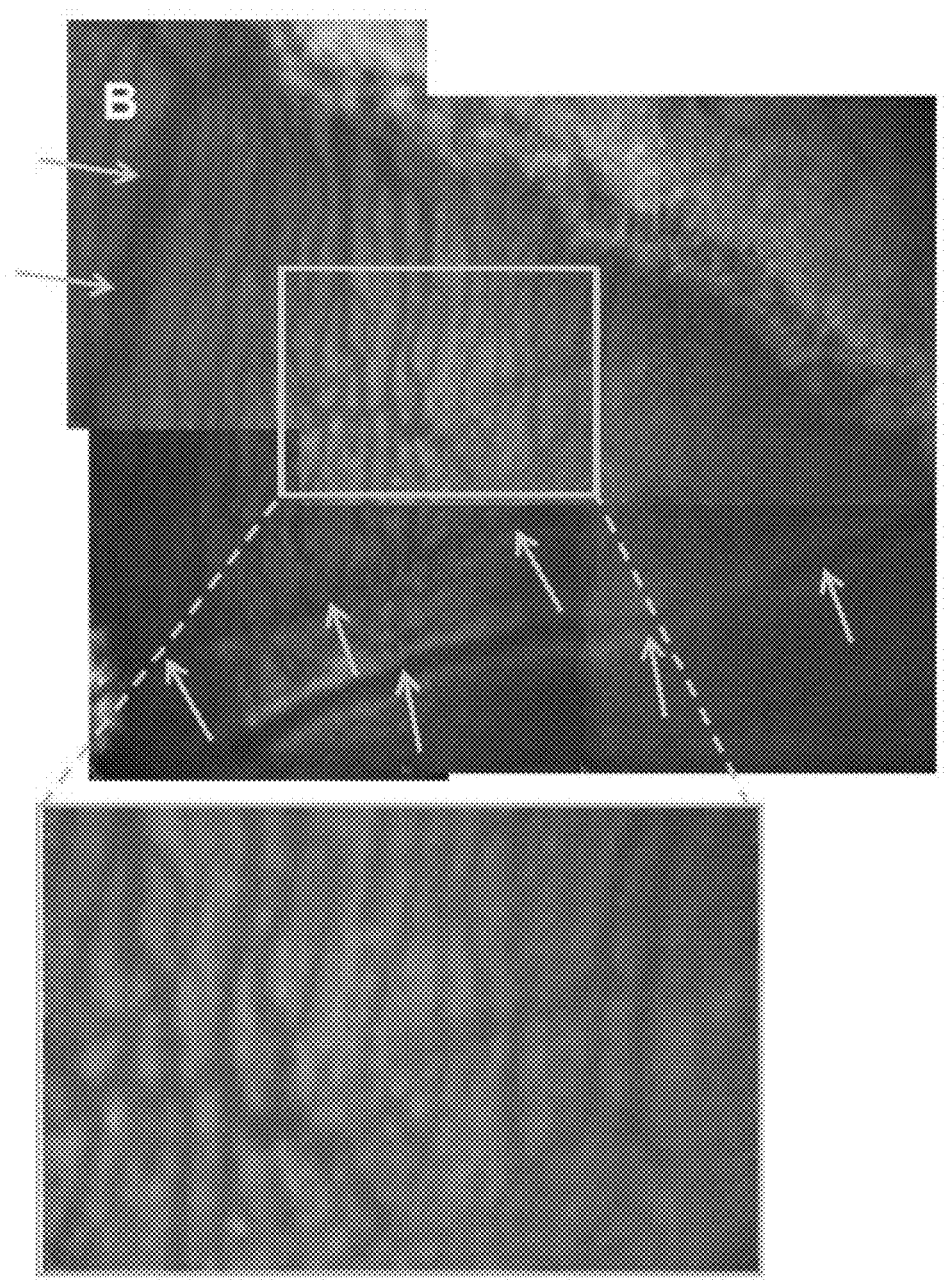

Having demonstrated that DNIRA identifies the RPE and/or outer retinal complex, it was determined that DNIRA could be used to identify structural abnormalities of the RPE. DNIRA was used in combination with systemic injection of the RPE toxin, $NaIO_3$. $NaIO_3$ is directly toxic to RPE cells and leads to their loss; apoptosis of the overlying photoreceptors occurs thereafter. DNIRA in the days and weeks after $NaIO_3$ injection identified geographic (spatial) patches of profound hypofluorescence, evident as large black patches within an otherwise continuous background of speckled fluorescence. These hypofluorescent patches were bounded by a defined border. Further, with the gain of the cSLO increased, brighter viewing through these patches permitted clear visualization of the choroidal detail (FIGS. 7A-B). Choroidal vessels were identified by their complexity, variable size, and non-radial pattern with respect to the ONH. By contrast, the speckled layer obscured this view but permitted ongoing visualization of the overlying retinal vessels. These data were consistent with the notion that DNIRA detects ICG-labeled RPE/outer retinal layer.

Further, the suitability of DNIRA for pre-clinical experimentation was demonstrated with toxicity studies. Electroretinography, comparing high and low dose systemic ICG concentrations against PBS, was undertaken. These data showed no statistically significant change in the b-wave amplitude in the three weeks following injection compared against changes noted in control animals, and demonstrate that DNIRA, over the dose range used, is safe in pre-clinical studies of chorioretinal disease. While the high dose is well above that used clinically, the low dose is consistent, in grams/body weight, with the dose used for clinical imaging with traditional fundus cameras.

Example 3: Discovery of Compounds for the Treatment of Blinding Eye Diseases

Having established an animal that models a blinding eye disease, a test compound is administered to such an animal.

The presentation of the blinding eye disease is determined using in vivo imaging including fluorescence detection. A candidate compound is identified by observing fluorescence in the eye at or after a time sufficient to present characteristics of a blinding eye disease. The candidate compound is evaluated for its ability to reduce or eliminate the characteristics of the blinding eye disease as described herein.

Example 4: Assessing the Activity of Compounds for Blinding Eye Diseases

Having developed an animal that models a blinding eye disease, a candidate compound is administered to such an animal.

The presentation of the blinding eye disease is determined using in vivo imaging including fluorescence detection. The activity of a candidate compound is assessed by observing fluorescence in the eye at or after a time sufficient to present characteristics of a blinding eye disease and the activity of a candidate compound. The candidate compound may be assessed for its ability to reduce or eliminate the characteristics of the blinding eye disease as described herein.

Example 5: Treatment of Dry AMD with Bindarit

Human subjects, 56 to 100 years of age or more, present with dry AMD, as diagnosed by one or more of the following clinical tests: clinical examination, FAF (at any wavelength), near infrared and/or red-free photography, fluorescein angiography, which allows for the identification and localization of abnormal vascular processes; OCT, which provides high-resolution, cross-sectional or en face images from within optical scattering media, such as the human retina and choroid; and structured illumination light microscopy, using a specially designed high resolution microscope setup to resolve the fluorescent distribution of small autofluorescent structures (lipofuscin granulae) in retinal pigment epithelium tissue sections.

The subjects are administered bindarit in two 300 mg oral doses once a day for 12 weeks. After an initial twelve-week treatment period, the subjects are evaluated for clinical outcomes. Alternatively, patients receive intravitreal injection of a vehicle containing bindarit, with or without a drug delivery vehicle.

A first clinical outcome is determined using a standard visual acuity test, as is well known in the art. The subjects are assessed for the ability to clearly see symbols and objects on a Snellen eye chart from a distance.

A second clinical outcome assesses the rate of progression of geographic atrophy. To do so, the subjects' pupils are dilated with 1.0% tropicamide and 2.5% phenylephrine before retinal imaging. Imaging is carried out with an instrument (e.g., Spectralis HRA+OCT; Heidelberg Engineering, Heidelberg, Germany) that allows for simultaneous recording of cSLO and spectral-domain optical coherence tomography (SD-OCT) with two independent scanning mirrors, as described in Helb, et al. *Acta Ophthalmol.* 2010 December; 88(8):842-9. Five modes of operation are employed: white light, red-free light, near infrared, FAF and OCT.

cSLO images are obtained according to a standardized operation protocol that includes the acquisition of near-infrared reflectance ($\lambda$=815 nm) and FAF (excitation at $\lambda$=488 nm, emission 500-700 nm) images. Simultaneous SD-OCT imaging is carried out with an illumination wavelength of 870 nm, an acquisition speed of 40,000 A-scans, and a scan depth of 1.8 mm. Two SD-OCT scans, one vertical and one horizontal, per eye are performed through the approximate foveal center, or in the case of RPD, in proximity to the vascular arcades of the macula. Fluorescein angiography ($\lambda$=488 nm, emission 500-700 nm, 10% fluorescein dye) is performed as needed. Color fundus photographs are obtained with a fundus camera (e.g. FF 450 Visupac ZK5; Carl Zeiss Meditec A G, Jena, Germany).

Interpretation of clinical outcome data informs a decision for further treatment, if any.

Example 6: Treatment of Dry AMD with a Combination Therapy

Human subjects, 56 to 100 years of age or more, present with dry AMD, as diagnosed by one or more of the following clinical tests: clinical examination, white-light fundus imaging, FAF at any wavelength, near infrared and/or red-free photography, blue-light illumination, and/or fluorescein or ICG angiography, which allows for the identification and localization of abnormal vascular processes; OCT, which provides high-resolution, cross-sectional, three-dimensional and en face images from within optical scattering media, such as the human retina and choroid; and structured illumination light microscopy, using a specially designed high resolution microscope or ophthalmoscope set up to resolve the distribution of small autofluorescent structures (lipofuscin, lipofuscin-like, or other granulae) in retinal pigment epithelium or other cells and cell layers.

The subjects are administered bindarit in two 300 mg oral doses once a day for 12 weeks. The subjects are also administered ranibizumab injection once per month (roughly 28 days) in a dose of 0.5 mg per affected eye. After an initial twelve-week treatment period, the subjects are evaluated for clinical outcomes.

A first clinical outcome is determined using a standard visual acuity test, as is well known in the art. The subjects are assessed for the ability to clearly see symbols and objects on a Snellen eye chart from a distance.

A second clinical outcome assesses the rate of progression of geographic atrophy. To do so, the subjects' pupils are dilated with 1.0% tropicamide and 2.5% phenylephrine or a comparable agent before retinal imaging. Imaging is carried out with an instrument (e.g., Spectralis HRA+OCT; Heidelberg Engineering, Heidelberg, Germany) that allows for simultaneous recording of cSLO and SD-OCT, as described in Helb, et al. *Acta Ophthalmol.* 2010 December; 88(8):842-9. Multiple modes of operation can be employed: white light, red-free light, blue light, near infrared, and OCT. Similar analysis can be performed with a modified fundus camera.

cSLO images are obtained according to protocols known in the art that may include the acquisition of near-infrared reflectance ($\lambda$=800-1000 nm) and FAF (excitation at $\lambda$=280-550 nm, emission 350-700 nm) images. Simultaneous SD-OCT imaging is carried out with an, for example, illumination wavelength of 870 nm, an acquisition speed of 40,000 A-scans, and a scan depth of 1.8 mm. Multiple SD-OCT scans per eye are performed through the macula and additionally or in the case of RPD, in proximity to the vascular arcades of the macula. Other OCT imaging, such as, for example, time domain and swept domain, can also be used. Fluorescein angiography ($\lambda$=488 nm, emission 500-700 nm, 10% fluorescein dye) is performed as needed. Color fundus photographs are obtained with a fundus camera (e.g. FF 450 Visupac ZK5; Carl Zeiss Meditec AG, Jena, Germany).

Interpretation of clinical outcome data informs a decision for further treatment, if any. Illustrative data analysis includes macular cube analysis and 5 line raster.

Example 7: Detection and/or Prediction of a Blinding Eye Disease Subject Response to an Agent Using multi-modal imaging in the rat eye, it was determined that systemic injection of the RPE toxin, $NaIO_3$, induces complex patterns of FAF similar to those in patients with aggressive forms of dry AMD and/or RPD. Tissue histology and fluorescent microscopy illustrated that the in vivo patterns of FAF correspond with the spatial distribution of autofluorescent cells of the innate immune system recruited to areas of RPE damage or loss.

Multi-Modal and Angiographic Imaging In Vivo:

Fundus imaging was performed using a commercially available confocal scanning laser ophthalmoscope, (cSLO, Spectralis, Heidelberg Retinal Angiography, HRA-II; Heidelberg Engineering GmbH, Germany), and the Eye Explorer Image Capture system, version 1.1.10. Images were captured at a wavelength of 488 nm excitation with 500 nm barrier filter for fluorescein angiography without the barrier filter for red free (RF, green dominant) imaging, at 795/810 nm excitation/emission for ICG angiography, and with a 830 nm laser for infrared reflectance imaging. To evaluate 488 nm FAF, cSLO imaging was performed in the absence of fluorescein dye. In cases in which it was necessary to simultaneously image the vasculature and provide landmarks for FAF image analysis, ICG was injected via tail vein, at 2 or 5 mg/kg, into a previously inserted 23 gauge tail vein catheter.

FAF imaging of normal Sprague Dawley rat eye produced a faint, homogenous ground glass glow interrupted by radially-arranged retinal blood vessels that block RPE fluorescence and therefore appear dark. Such imaging was also characterized by a central hypofluorescent circle at the optic nerve head (ONH), where RPE is absent. Systemic injections of $NaIO_3$ (45% solution, prepared fresh for each set of experiments in 0.9% sodium chloride and injected to a final concentration of 45 mg/kg body weight) were given to experimental rats. Three days after injection, a single area of iso- or slightly hyperfluorescent FAF with hyperfluorescent borders appeared and took the shape of a discrete island, sector, or 360° ring. In all cases, the islands, sectors or rings approached the ONH but were not contiguous with it. These and the following observations were confirmed in over 160 eyes.

Beginning approximately 4 to 5 days after $NaIO_3$ injection, a marked reticular or curvilinear pattern of alternating hyper/hypo-fluorescent FAF appeared within the islands, sectors, or rings. By day 7, this pattern was pronounced and it continued to emerge over weeks, whereby its curvilinear components contributed to partial loops, ovals, circles, rosettes, and scalloped or "paw-print" patterns of FAF. Even as late as 20 weeks, the last time-point analyzed, the borders retained their hyperfluorescent reticular pattern and continued to creep slightly toward the retinal periphery.

Fluorescein angiography performed in a subset of animals confirmed that the reticular pattern does not correspond with the retinal or choroidal vasculature while ICG angiography revealed a permeability change that occurred at the chorioretinal interface, across the RPE and BM, approximately two to three days after $NaIO_3$ that coincides with, both spatially and temporally, the emergence of the islands, sectors of rings of FAF. This increase in permeability is transient and resolved by day 7, the next time point routinely evaluated. The retinal vessels do not leak. Hemotoxylin and eosin (H & E) histology of paraffin-embedded tissue and immunohistochemistry (IHC) (known in the art; performed after fixation with, e.g., Davidson's fixative and paraffin-embedded sections, viewed with a Nikon Upright E800 Microscope) confirmed that fluid accumulated in the subretinal space. This was also observed by ultra-high resolution OCT in vivo (high resolution 160 nm spectral domain OCT images were obtained using the Envisu 82200 VHR Animal SDOIS System, Bioptogen, USA; scans were acquired at a rate of 36,000 per second, with a lateral resolution of approximately 2.8 μm at the level of the retina).

Autofluorescent and Immunofluorescent Analysis of Excised Retina and RPE:

To determine the pathological correlate of the FAF pattern observed in vivo, excised retinal whole mounts were viewed at low magnification under white light and by epifluorescent microscopy at 488 nm, the same wavelength used for in vivo imaging, with no fluorescent IHC labeling. Depending on subsequent tissue analysis, two microscopes were used for this purpose: an epifluorescent device with a narrow excitation/emission window (488/520 nm), and the Inverted Leica DM IRE2 viewing system of a confocal microscope with a mercury arc lamp and long-pass (rather than band-pass) filter providing fluorescence from greater than 515 nm following excitation with a 450-490 nm band. Under white light, the normal rat retina appeared fairly homogenous throughout, with some artifactuous deformation. By contrast, a subtle off-white, fine reticular pattern became apparent in samples obtained 7 days after NaIO$_3$ injection. By day 14, this pattern was more apparent and was observed to correspond with small, outer retinal folds best illustrated at the cut edge of the retina. Viewed under 488 nm fluorescent light, this same curvilinear pattern was apparent. Using higher magnification epifluorescent microscopy, it was demonstrated that this lacy, curvilinear pattern coincides with the spatial distribution of autofluorescent cells that appear to align with grooves or folds of the outer retina.

To determine the identity of the autofluorescent cells that coincide with the reticular pattern of FAF, excised retina were stained for with markers of the innate immune system, avoiding the 488 nm channel. Iba1 is a pan-microglial/macrophage marker and in the rat retina; antibodies against it identify the major phagocytic cell populations. Using this marker, it was found that Iba1 cells are arranged in a lacy, curvilinear pattern when viewed en face in whole mount retina, i.e. in the z-plane. Further, when compared against photoreceptor nuclear staining, this curvilinear pattern is seen to lie interposed between folds of the deformed ONL. This pattern of Iba1$^+$ cells corresponds with the pattern of hyperfluorescence observed in vivo by FAF imaging, and with the pattern of autofluorescent cells in excised retina. Corresponding patterns of in vivo FAF and Iba1 staining were observed at both 7 days and 12 weeks after NaIO$_3$ injection. Importantly, at 7 days after NaIO$_3$, all RPE cells are absent from the posterior eye cup, confirming that these cells cannot be responsible for the observed FAF. Also, identification of the autofluorescent cells as phagocytic was confirmed by comparison of imaging to preparations in which monocyte/macrophage depletion has been undertaken. Such depletion was achieved by treatment with gadolinium chloride (GAD). Upon treatment with GAD, far less well defined reticular patterns of FAF were observed, including a reduction in demarcation of the borders.

Such identification of phagocytic cells is indicative of dry AMD and/or RPD and predictive of a subject's response to an agent. Specifically, the observation of such phagocytic cells makes it more likely than not that a subject will respond to treatment with an agent.

Identification of a transient increase in permeability across a subject's epithelial barrier between a choroid and a retina relative to an undiseased state is indicative of dry AMD and/or RPD and predictive of a subject's response to an agent. Specifically, the observation of a transient increase in permeability across a subject's epithelial barrier between a choroid and a retina relative to an undiseased state makes it more likely than not that a subject will respond to treatment with an agent.

Delayed Near InfraRed Analysis (DNIRA) of Excised Retina and RPE:

Also, identification of abnormal features in comparison with the normal eye is undertaken with Delayed Near Infra Red Analysis (DNIRA). DNIRA images are obtained in the days and weeks after dye injection, such as ICG injection, using the ICG angiography settings, i.e. with excitation/emission filters, but without re-injection of dye at 24 hours, 48 hours, 3 days, 7 days, 21 days or 28 days after angiography. Angiography is not performed again during the time-course of the study.

For toxin administration, a toxin such as NaIO$_3$ (Sigma, cat #424064) is injected systemically via a 23G catheter at a dosage of 45 mg/kg body weight. ICG angiography at 0.35 mg/kg is performed immediately prior to NaIO$_3$ injection. DNIRA is performed 7 days after ICG and NaIO$_3$ injection.

Example 8: DNIRA of a Rat Eye after Systemic ICG Administration Labels Immune Cells in Vivo To determine the pathological correlate of the FAF pattern observed in vivo, excised retinal wholemounts were viewed at low magnification under white light and by epifluorescent microscopy at 488 nm—the same wavelength used for in vivo imaging, with no fluorescent IHC labeling. Depending on subsequent tissue analysis, two microscopes were used for this purpose: an epifluorescent device with a narrow excitation/emission window (488/520 nm), and the Inverted Leica DM IRE2 viewing system of a confocal microscope with a mercury arc lamp and long-pass (rather than band-pass) filter providing fluorescence from greater than 515 nm following excitation with a 450-490 nm band. Under white light, the normal rat retina appeared fairly homogenous throughout, with some artifactuous deformation (FIG. 3A). By contrast, a subtle off-white, fine reticular pattern became clear in samples obtained 7 days after NaIO$_3$ injection. By day 14, this pattern was more clear and seen to correspond with small, outer retinal folds best illustrated at the cut edge of the retina (FIG. 3B). Viewed under 488 nm fluorescent light, this same curvilinear pattern was apparent. Though clear by day 7 after injection, increasing autofluorescence made this pattern more visible by Day 14 (FIG. 3C). Using higher magnification epifluorescent microscopy, we demonstrated for the first time that this lacy, curvilinear pattern coincides with the spatial distribution of autofluorescent cells that appear to align with grooves or folds of the outer retina (FIG. 3D).

Without wishing to be bound by theory, this suggests that the in vivo pattern of FAF observed corresponds with distribution of autofluorescent cells in the outer retina. This contrasts with the prevailing theories that ascribe clinically-relevant patterns of FAF to abnormal RPE, noting that RPE are absent in the isolated retinal samples we used. Without wishing to be bound by theory, this also suggests that the 2-dimensional pattern of FAF observed in this model corresponds with distribution of autofluorescent cells confined within 3-dimensional curvilinear folds of the outer retina. Accordingly, the spatial and temporal changes of the outer retinal structure and the identity of the autofluorescent cell types was investigated.

Owing to the laminar nature of the neuroretina, we reasoned that outer retinal deformation could be readily evaluated by observing conformational changes of the normally flat outer nuclear layer (ONL), a layer of densely arrayed photoreceptor nuclei. Therefore, immediately after autofluorescent analysis of freshly excised wholemount retina, nuclear staining was performed and the tissue evaluated by epifluorescent or confocal microscopy in a non-488 channel. Cross-sections were also evaluated by H&E of whole eyes.

At baseline prior to NaIO$_3$ administration, confocal microscopy using the nuclear stain Topro3 confirms that the ONL was flat and devoid of vascular staining (FIG. 4C). Three days after NaIO$_3$ administration, slight curvilinear grooves of the ONL were noted, accompanied by occasional shallow, linear creases. By Day 7, ONL deformation was more pronounced, producing a distinctly interconnected series of grooves. By Day 14 these changes were more complex and of higher amplitude.

Cross-sectional H & E histology of retina at 90° to images obtained using confocal microscopy, showed that NaIO$_3$-induced RPE toxicity first leads to small undulations of the ONL that accompany increasing subretinal fluid, with little photoreceptor loss (FIG. 4B). Later, frank photoreceptor loss created higher amplitude folds in which the troughs of the ONL are juxtaposed against Bruch's membrane (BM), the basement membrane of the RPE. Eventually, lateral expansion of these troughs led to large contiguous regions of outer retinal degeneration such that much of the inner retina lies juxtaposed against BM.

To determine the identity of the autofluorescent cells that coincide with the reticular pattern of FAF, the excised retina with markers of the innate immune system was statined, avoiding the 488 nm channel. Iba1 is a pan-microglial/macrophage marker and in the rat retina; antibodies against it identify the major phagocytic cell populations. Using this marker, it was shown that Iba1$^+$ cells are arranged in a lacy, curvilinear pattern when viewed en face in wholemount retina, namely, in the z-plane (FIGS. 5A-H). Further, when compared against photoreceptor nuclear staining, this curvilinear pattern was seen to lie interposed between folds of the deformed ONL. As shown in FIGS. 5A-H, this pattern of Iba1$^+$ cells corresponded with the pattern of hyperfluorescence observed in vivo by FAF imaging (FIGS. 1A-D and 2A-D), and with the pattern of autofluorescent cells in excised retina (FIGS. 3A-C). Corresponding patterns of in vivo FAF and Iba1 staining are shown at both 7 days and 12 weeks after NaIO$_3$ injection (FIGS. 5A and 5B). By 7 days after NaIO$_3$ administration, all RPE cells were absent from the posterior eye cup, confirming that these cells were not responsible for the observed FAF (FIGS. 5C and 5D).

The 3-dimensional (3D) relationship between the Iba1$^+$ cells and the outer retina was next evaluated by en face serial confocal microscopy of wholemount retina (i.e., in the z-axis) moving step-wise from the inner plexiform layer (INL) through the outer plexiform layer (OPL), to the inner-, mid- and outer-ONL. Short stacks of confocal images (segments) were projected (flattened) at these three steps (FIGS. 6A-D). The co-distribution of activated CD68$^+$ macrophages of the monocyte lineage was also evaluated.

At baseline prior to NaIO$_3$ administration, Iba1 cells were seen in the IPL only. No CD68$^+$ cells were identified (FIG. 6A). Three to four days after NaIO$_3$ administration, Iba1$^+$ cells increased in number and were increased in the IPL and also throughout the outer retina, including the outer-ONL (FIG. 6B). Two weeks after NaIO$_3$ administration, a complex distribution of Iba1$^+$ and CD68$^+$ cells was seen interlaced between curvilinear folds of the ONL. Further, well-defined optically-sectioned ectopic circles or ovals of photoreceptor nuclei were observed as far internally as the OPL, the mid-retinal layer of blood vessels, thereby bringing the deformed photoreceptor nuclear layer and vascular layer, two normally separate tissue compartments, in contact. In the mid-ONL, ovoid cross-sections of the deformed nuclear layer appeared more curvilinear or pisciform, and large Iba1$^+$ and CD68$^+$ cells were found within their central void. In the outer-most third of the ONL, optical cross-sections remain curvilinear and were largely contiguous with many bridging segments. The subretinal space, normally a potential space only, was expanded by outer retinal deformation and shows Iba1$^+$ and/or CD68$^+$ inflammatory cells and photoreceptor nuclei together immediately internal to Bruch's membrane (in the space where the lost photoreceptor outer segments would normally reside).

Confocal scanning microscopy and three-dimensional reconstruction of the excised wholemount retina was undertaken (FIG. 7A). These data showed that Iba1$^+$ cells formed a reticular or lacy pattern that is interposed between photoreceptor nuclei. Further, projection of the z-stack, divided into the same three planes (FIG. 7B right) showed that the inner-ONL is characterized by circular or oval cross-sections of the ONL. By contrast, the mid-ONL is characterized by looping curved cross-sections of the nuclear layer, and the outer ONL is formed of larger curvilinear segments with multiple bridging elements. Oblique volumetric projections of these layers readily illustrate the resulting pseudo-eggcrate configuration of the ONL, with several conical peaks extending from single contiguous folds at its base (FIG. 7B middle and right). Without wishing to be bound by theory, these data demonstrate that the majority of inflammatory cells are not located within or between ONL troughs, but rather are found under (i.e. external to) the ONL peaks in the expanded subretinal space.

Without wishing to be bound by theory, these observations show that the 3-dimensional distribution of autofluorescent inflammatory cells under the deformed outer retina accounts for the 2D pattern of in vivo FAF imaging in these animals.

Figure 8A:
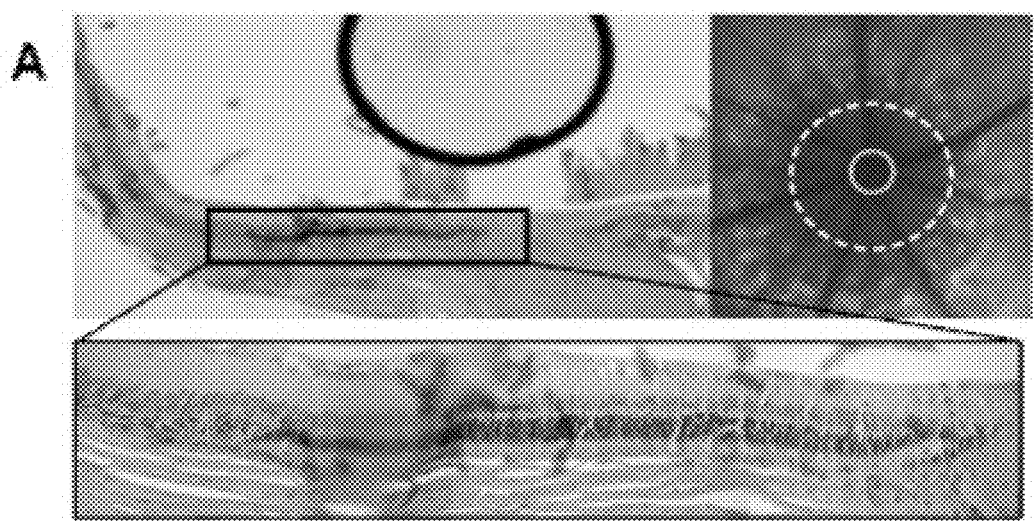
FIGS. 8A-C show that the reticular FAF pattern matures in vivo and in excised retina, and spares the area adjacent to the optic nerve.

To correlate these observations made in excised tissue to in vivo change and FAF findings, 3D volumetric analysis of the living retina using high-resolution OCT in vivo was performed. HR-OCT provides non-invasive, in vivo cross-sections of the retina previously observed only in post-enucleation histological specimens. OCT imaging is dependent on the signal generated at the interface between layers of differing optical density, and in the normal rat retina confirms its multi-laminar structure. The three major outer-most OCT boundaries of the retina are, from internal to external, the external limiting membrane (ELM), the junction of photoreceptor inner and outer segments (IS/OS), and the RPE/BM (FIG. 8A, left). Standard techniques both in the clinic and in these investigations arbitrarily set the nuclear layers, including the ONL, as dark (i.e. a signal void).

Figure 8B:
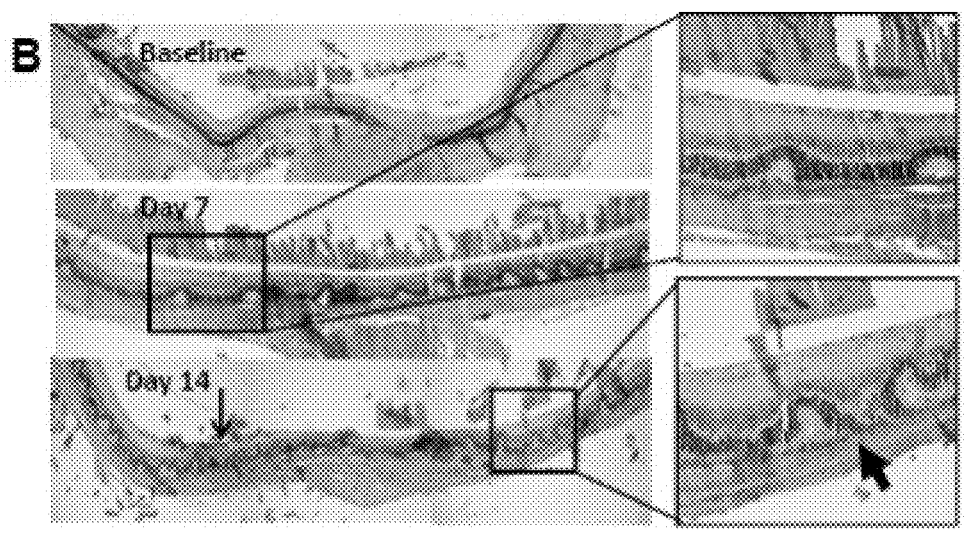
Figure 8C:
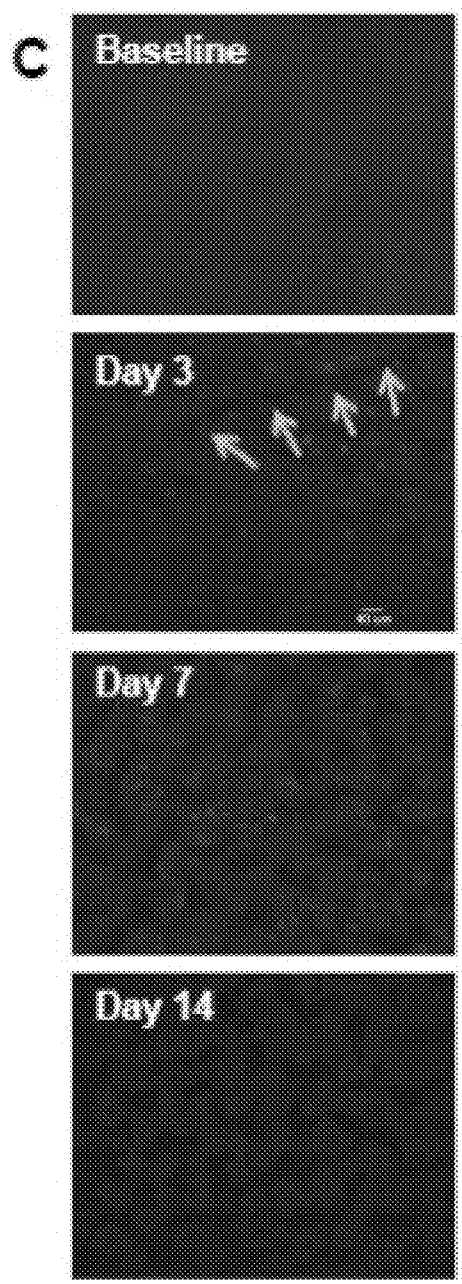

Three days after NaIO$_3$ administration, a reconstructed en face image of the living retina captured using OCT demonstrated a subtle change that is limited to the region inferior to the optic nerve (FIG. 8A, middle). Compared against baseline and the superior retina (which appears grossly normal three days after NaIO$_3$ administration) (FIG. 8A, middle), optical cross sections in the inferior retina showed slight deformation of the photoreceptor IS/OS junction and ELM such that bright (hyper-echoic) shallow mounds become visible (FIG. 8A, right). This signal was found external to the ONL and internal to BM. The fine dark line representing that the RPE was no longer present. By day 14, these mounds matured into pronounced peaks, a portion of which form bright, distinct triangles or pyramids whose bases appear to sit on BM (FIGS. 8B and 8C). Other mounds formed discrete narrow spikes that extended from the ELM, through the photoreceptor layer to reach the mid-retina. A clinical OCT image from a human patient with RPD shows a pyramidal subretinal deposit that is pathognomic of this disease (FIG. 8D).

To test if the bright mounds, triangles and spikes that characterize RPD and that seen in the present system, correspond with the distribution of autofluorescent phagocytic cells observed in the sub-retinal space volume-intensity projections (VIPs) were used. These were composed of OCT-generated optical sections to provide a means of evaluating 3-dimensional blocks of living tissue in vivo that can be reconstructed in the z- and y-axis.

Figure 9A:
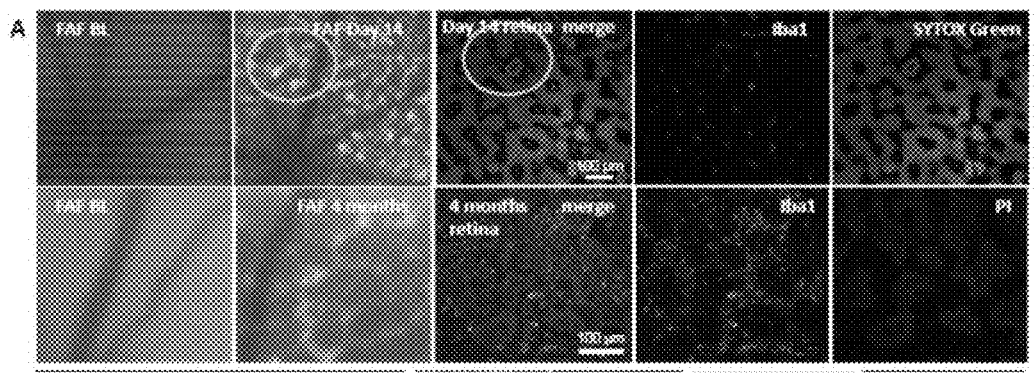
FIGS. 9A-C show that Iba1⁺ cells contribute to the reticular FAF pattern in the absence of RPE early and late in disease.

Reconstruction of adjacent OCT images in the y-axis showed that the mounds or triangles, arrayed side-by-side, contribute to complex structures such as circles, ovals, halos and target-like lesions. In the example shown in FIG. 9A, two subretinal mounds form the "sides" of a circle and lie close together at its superior and inferior aspect and maximally apart in the middle. Single mounds, pyramids and spikes contribute to simpler curvilinear structures.

Figure 9B:
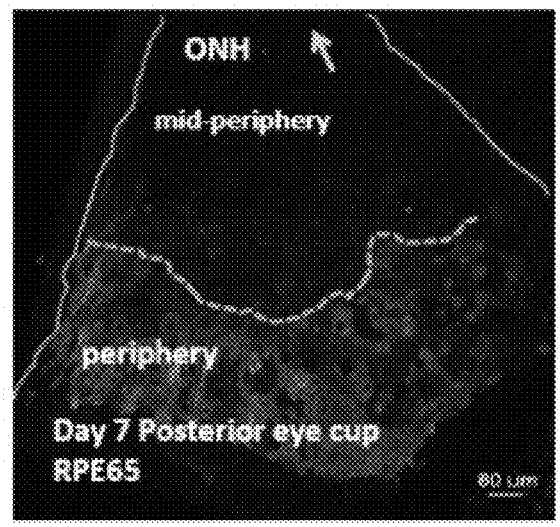
Figure 9C:
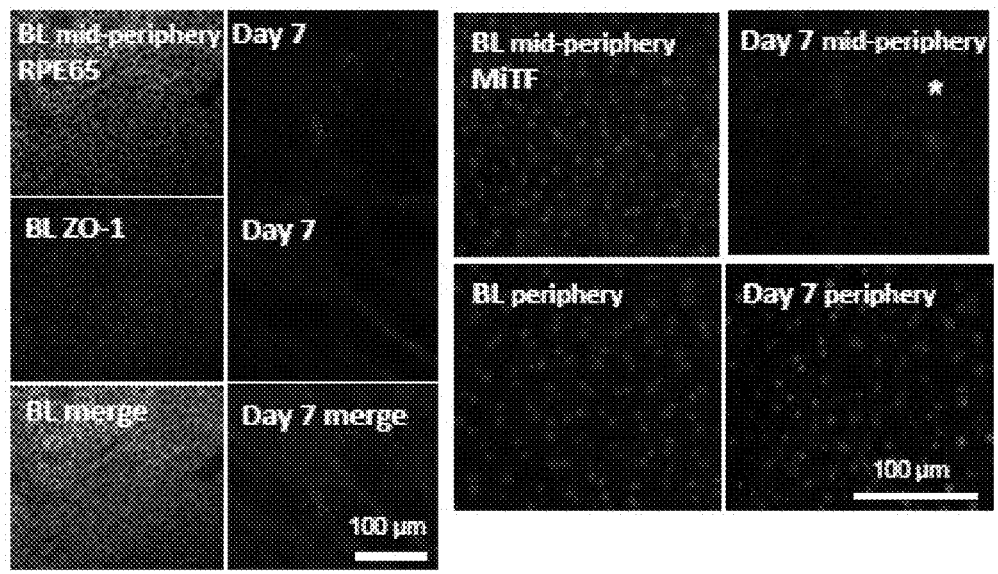

To further support this finding, VIPs in the z-axis, (that is, in step-wise short segments from the inner-ONL to outer-ONL), were then analyzed (FIG. 9B). VIPs through the inner-ONL showed a series of punctate spots, regularly spaced throughout the retina. VIPs from the mid-ONL showed less regularly spaced pisciform or curved short lines, some of which are bridging. VIPs from the outer-ONL showed contiguous curvilinear segments with many bridging elements. These findings directly correspond with the 3D data generated from excised wholemount retina (FIGS. 6A-D).

Further, to confirm that hyperfluorescent FAF or abnormal patterns of FAF and hyperfluorescent DNIRA correlated or co-localized with the distribution of phagocytic cells, the circulating macrophage/monocyte population was depleted using gadolinium chloride (GAD or $GdCl_3$), a rare earth metal salt which depresses macrophage activity. GAD depletion of immune cells led to profound alteration of the $NaIO_3$-induced pattern of FAF and DNIRA. GAD depletion of the monocyte/macrophage populations led to profound alteration of the $NaIO_3$-induced pattern of FAF. This was evident qualitatively both within the geographic areas of damage, and at its border (FIGS. 8A-C).

Example 9: Clinical In Vivo Imaging of RPD and Diffuse Trickling AMD

Figure 10C:
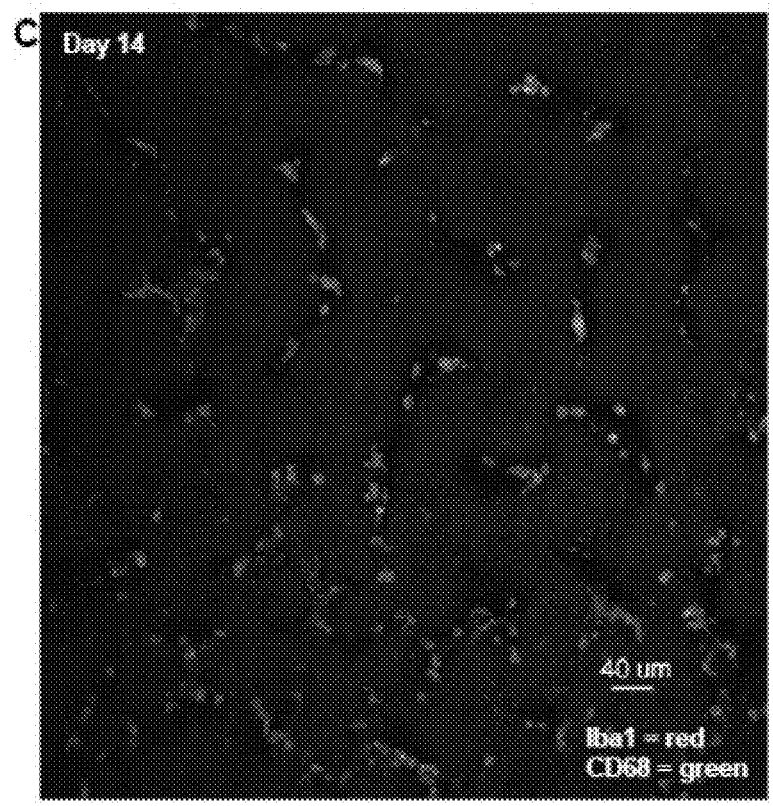
Figure 11A:
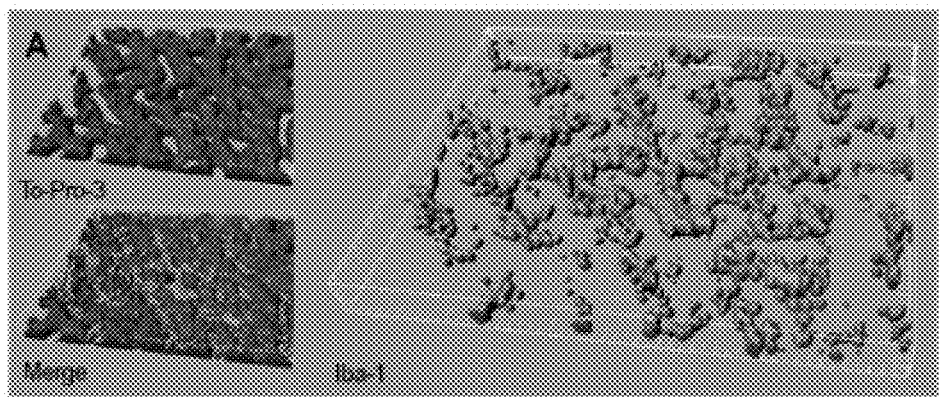
FIGS. 11A-B show three dimensional reconstruction of excised retinal whole mount tissue which confirmed that phagocytic cells lie within the deformed photoreceptor layer forming a reticular pattern
Figure 11B:
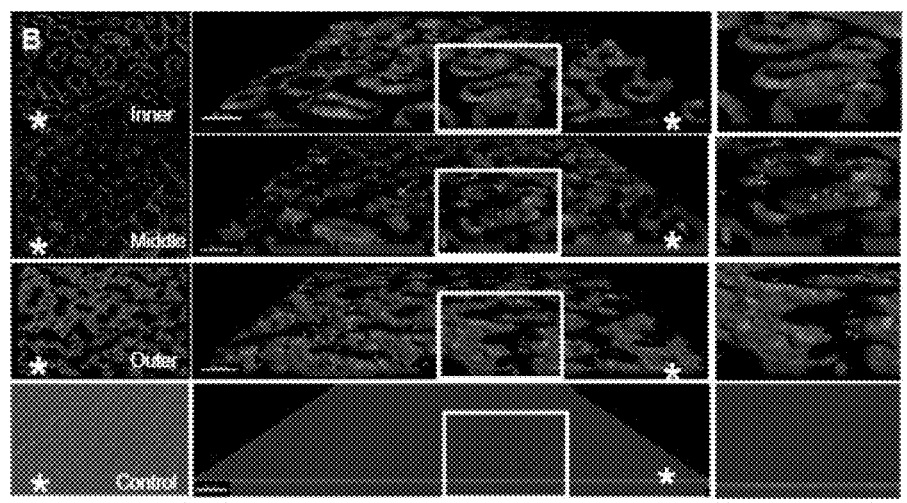
Figure 12A:
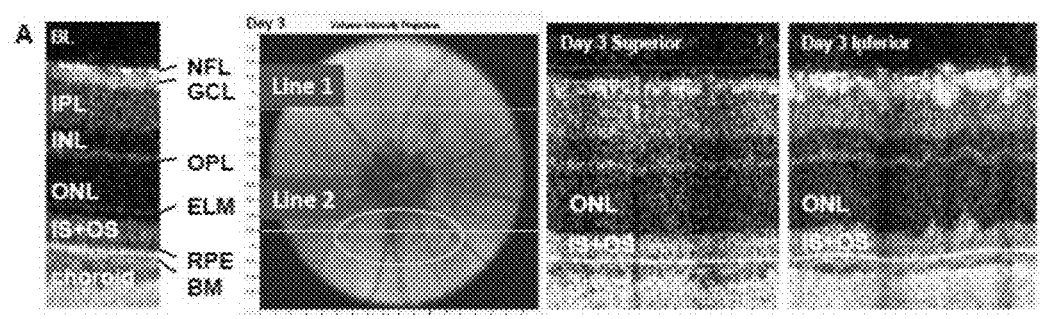
FIGS. 12A-D show that progressive NaIO₃-induced outer retinal deformation was identified by OCT imaging in vivo and compared to clinical findings (abbreviations: NFL=nerve fiber layer; GCL=ganglion cell layer; IPL=inner plexiform layer; INL=inner nuclear layer; OPL=outer plexiform layer; ONL=outer nuclear layer; IS+OS inner segment & outer segment layer; RPE=retinal pigment epithelium; BM=Bruch's membrane).
Figure 12B:
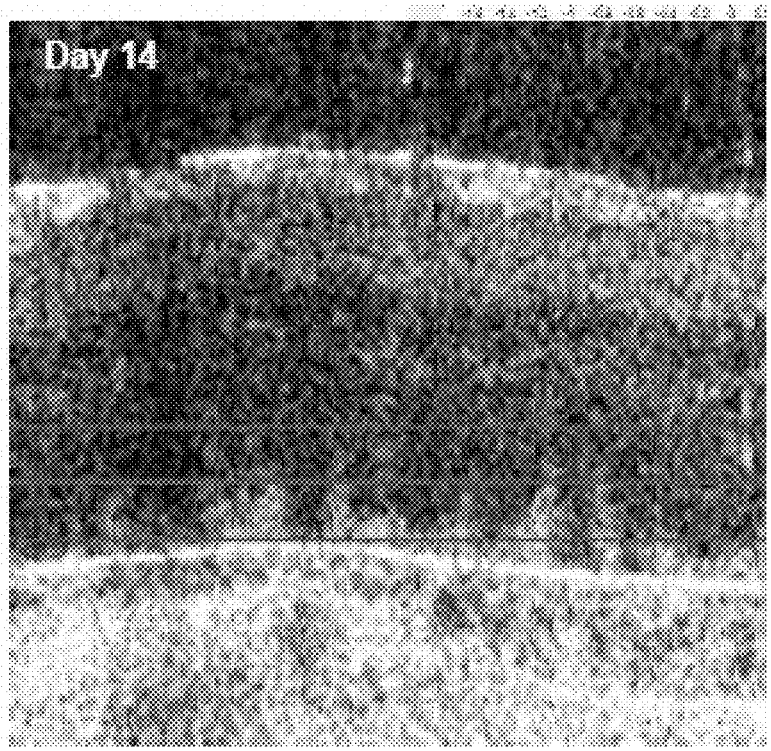
Figure 12C:
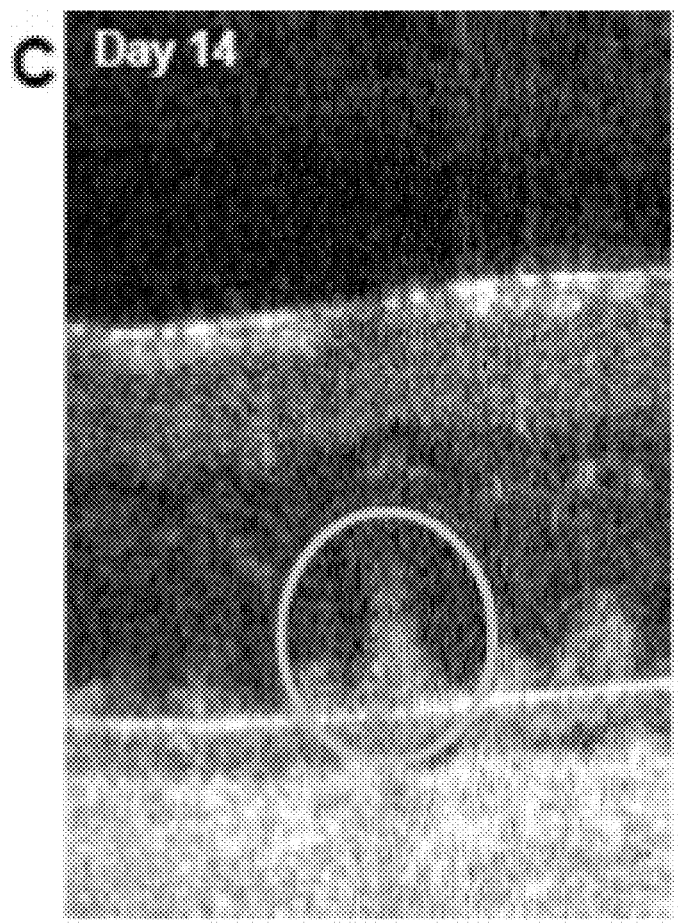
Figure 12D:
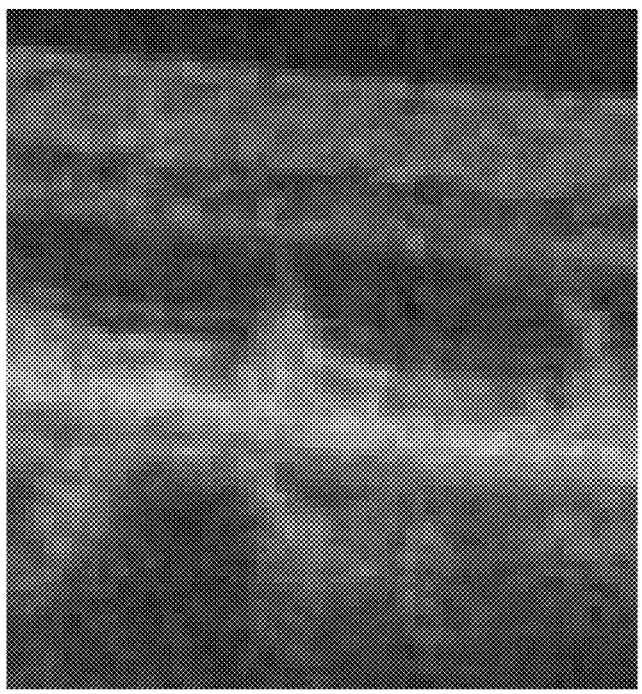
Figure 13A:
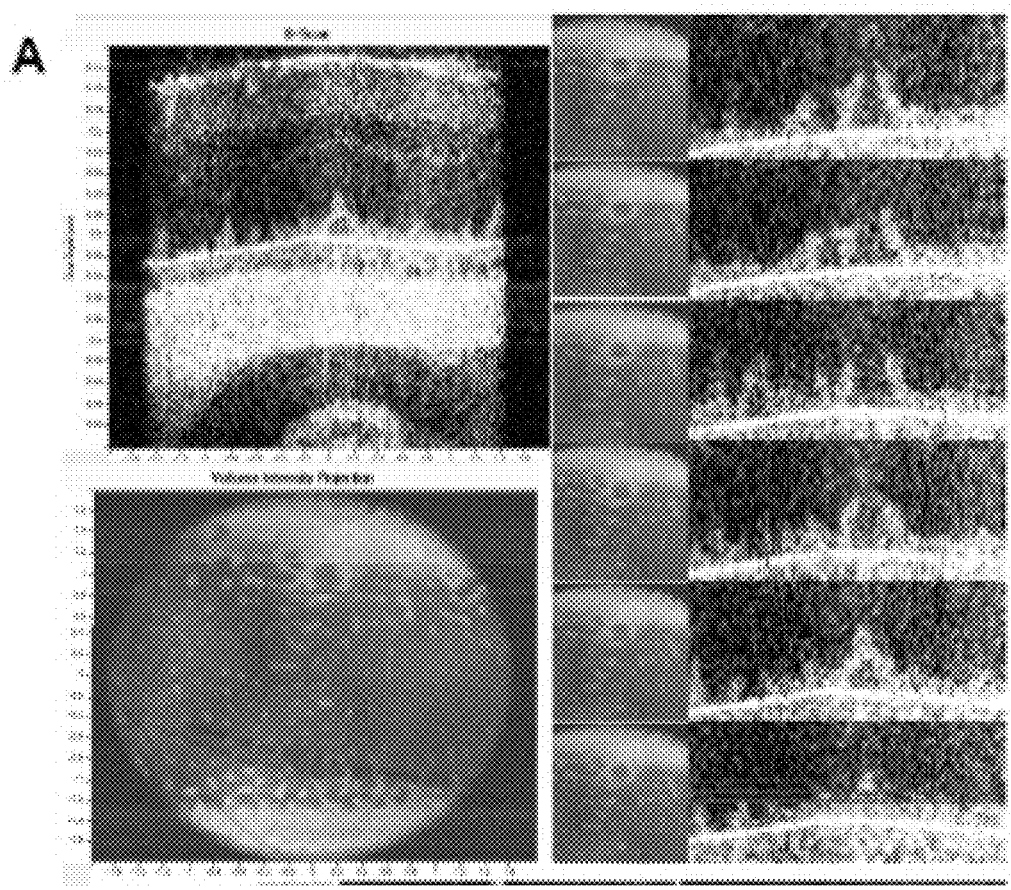
FIGS. 13A-B show that subretinal changes contributed to complex 3D structures in the Y-axis and Z-axis in vivo.
Figure 13B:
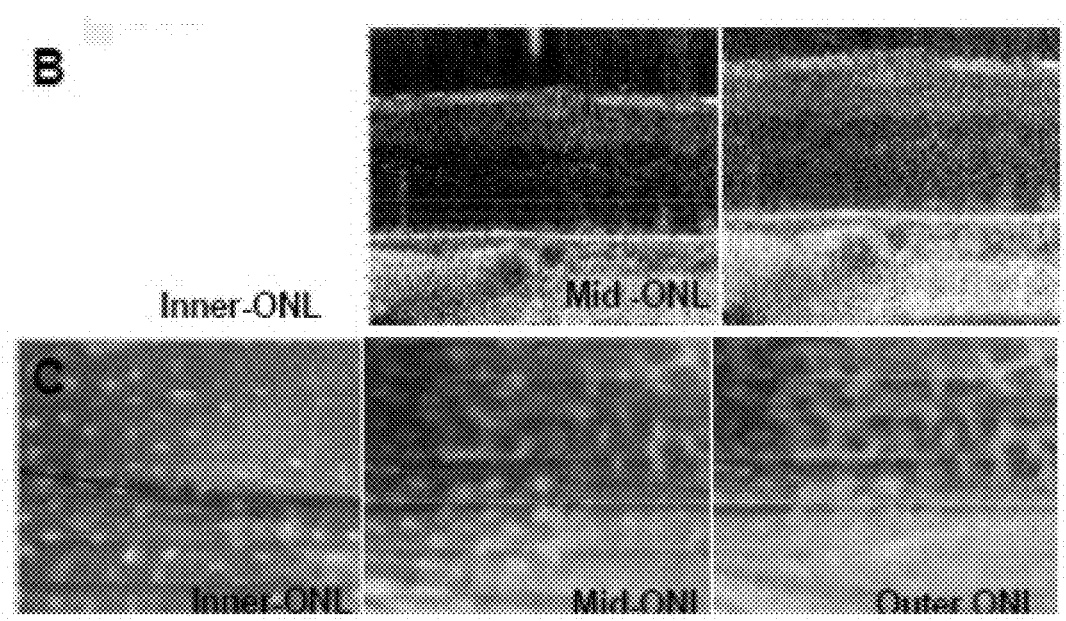
Figure 14A:
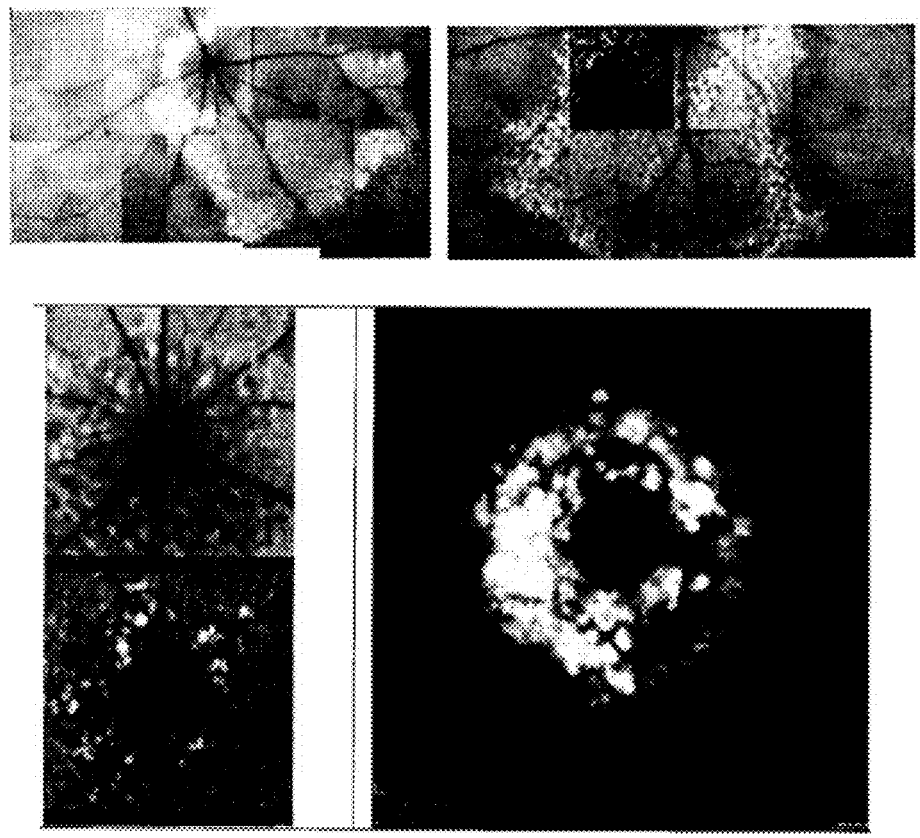
FIGS. 14A-B show that gadolinium, which depletes circulating monocytes and resident macrophages alters the FAF pattern of NaIO$_3$-induced outer retinal damage.
Figure 14B:
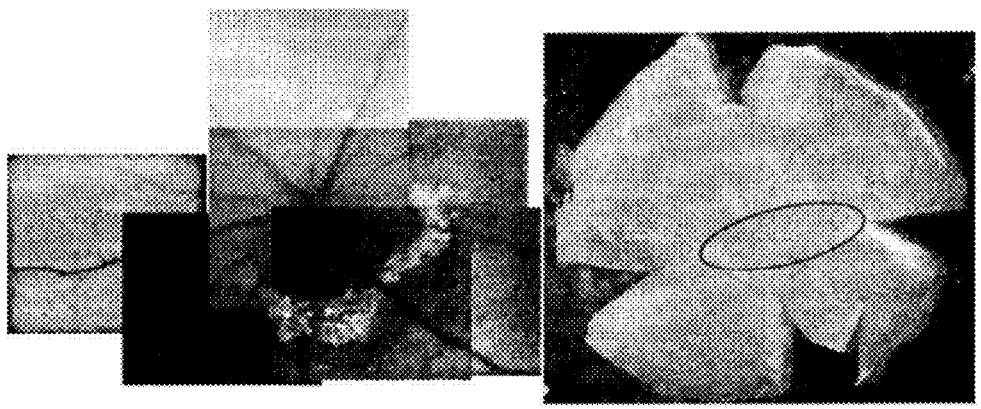
Figure 15A:
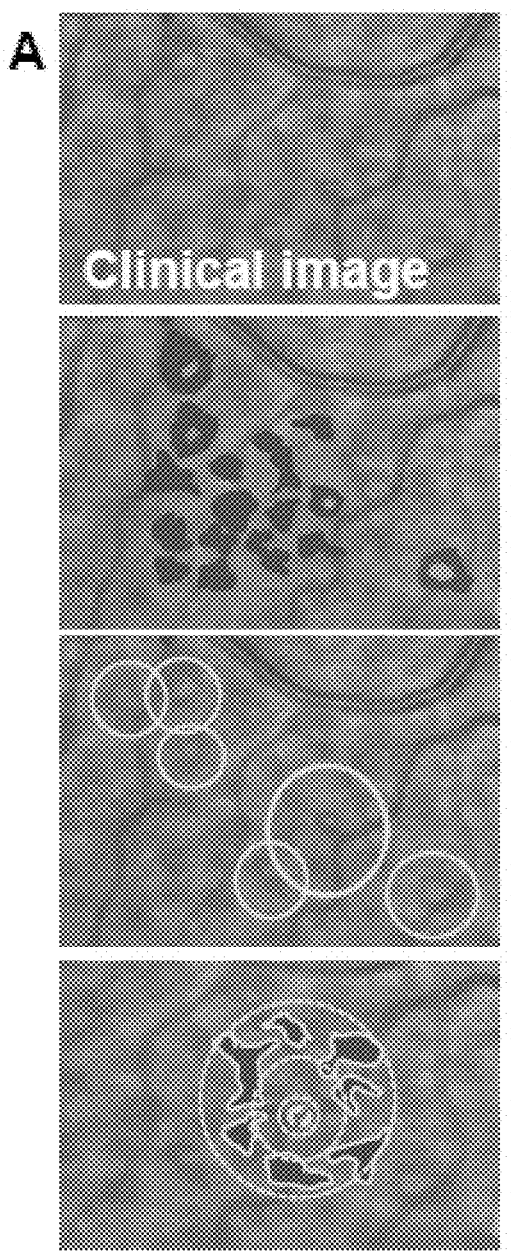
FIGS. 15A-C show interpretative illustrations of how, without wishing to be bound by histologically-determined tissue findings can account for in vivo imaging following NaIO3-induced RPE loss.
Figure 15B:
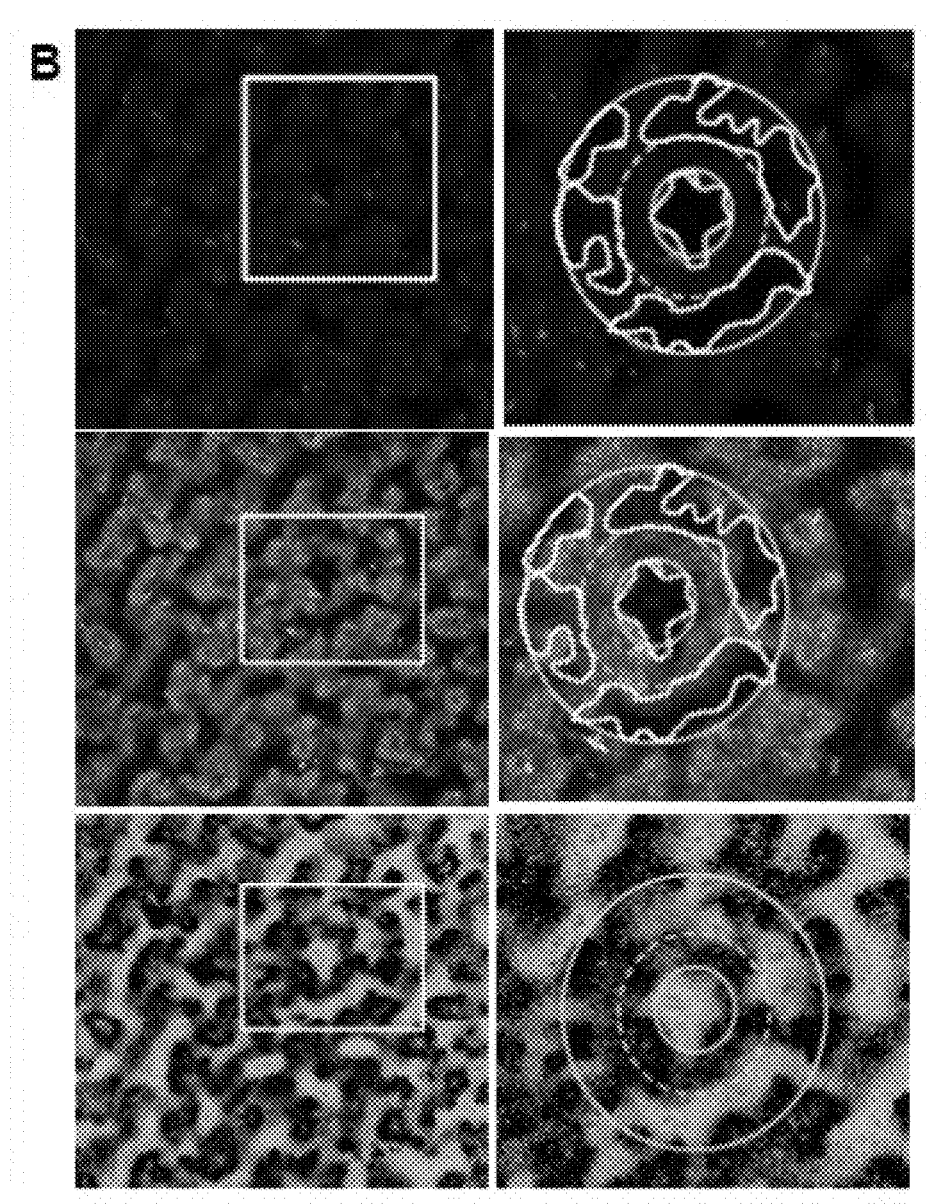
Figure 15C:
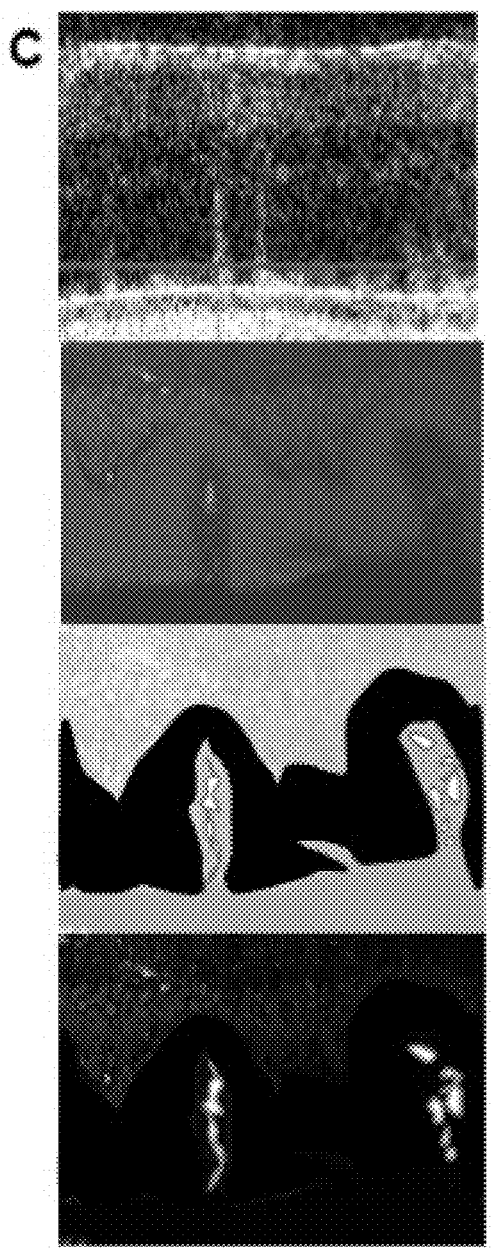

In FIGS. 10A-C, images and interpretive diagrams that directly compare the clinical features of RPD against tissue findings in the $NaIO_3$ model are provided. In addition to clinical OCT imaging of a human patient with RPD (that shows a base-down pyramidal structure in the subretinal space, FIG. 8D), color and red-free fundus images were also obtained (FIGS. 10A-C). Red free images showed small dark spots that constitute individual pseudodrusen of RPD (FIG. 10A, top image). These were identified using dark grey overlay. This further highlights, circumscribed by circles, the presence of so-called "target lesions" that characterize RPD. These appear as dark spots with lighter centers. In parallel, a schematized illustration of folded outer rat retina is presented, both en face and in cross-section that, when falsely colored and presented as black and white images—both "positive" and "negative"—correlates directly with targets and halos of RPD.

These data indicate that the 2D patterns of dark pseudodrusen within a lacy or reticular pattern of circles, halos and target lesion with dark centers viewed en face, in 2D, correspond with elevated rings and craters, considered volumetrically, in 3D.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A method for treating reticular pseudodrusen (RPD) disease, comprising ophthalmically administering to a subject in need thereof an effective amount of a compound of Formula I:

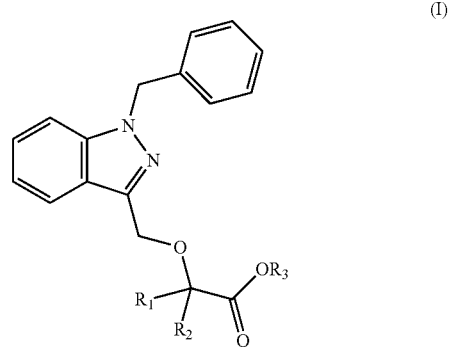

or a pharmaceutically acceptable salt thereof, wherein:
each of $R_1$ and $R_2$ is independently H or a $C_1$-$C_6$ alkyl and
$R_3$ is H or a $C_1$-$C_6$ alkyl.

2. The method of claim 1, wherein the compound of Formula I is bindarit.

3. The method of claim 1, wherein the method comprises reducing the amount of pseudodrusen in the subject.

4. The method of claim 3, wherein the method comprises reducing the amount of pseudodrusen in any one of the foveal area, perifoveal area, and juxtafoveal area of the subject's eye.

5. The method of claim 3, wherein the reduction in the amount of pseudodrusen in the subject is assessed using optical coherence tomography (OCT).

6. The method of claim 1, wherein the method comprises reducing expansion of pseudodrusen in the subject.

7. The method of claim 6, wherein the method comprises reducing expansion of pseudodrusen in any one of the foveal area, perifoveal area, and juxtafoveal area of the subject's eye.

8. The method of claim 1, wherein the method further comprises administering an additional therapeutic agent.

9. The method of claim 8, wherein the additional therapeutic agent is one or more of an anti-vascular endothelial growth factor (VEGF) agent, an angiotensin-converting enzyme (ACE) inhibitor, a peroxisome proliferator-activated receptor (PPAR)-gamma agonist, a renin inhibitor, a steroid, and an agent that modulates autophagy.

10. The method of claim 1, wherein the bindarit is formulated for ophthalmic administration.

11. The method of claim 10, wherein the ophthalmic administration is intravitreal or intraocular administration.

12. The method of 10, wherein the bindarit is formulated for sustained release.

13. The method of 1, wherein the bindarit is ophthalmically administered using sustained release.

* * * * *